US010760100B2

(12) United States Patent
Soucaille et al.

(10) Patent No.: US 10,760,100 B2
(45) Date of Patent: Sep. 1, 2020

(54) POLYPEPTIDE HAVING FERREDOXIN-NADP+ REDUCTASE ACTIVITY, POLYNUCLEOTIDE ENCODING THE SAME AND USES THEREOF

(71) Applicants: Institut National des Sciences Appliquees, Toulouse (FR); Centre National de la Recherche Scientifique (CNRS), Paris (FR); Institut National de la Recherche Agronomique, Paris (FR)

(72) Inventors: Philippe Soucaille, Deyme (FR); Isabelle Meynial-Salles, Fourquevaux (FR); Céline Foulquier, Escalquens (FR); Antoine Riviere, Rambouillet (FR)

(73) Assignees: Institut National des Sciences Appliquees (FR); Centre National de la Recherche Scientifique (CNRS) (FR); Institut National de la Recherche Agronomique (FR)

( * ) Notice: Subject to any disclaimer, the term of this patent is extended or adjusted under 35 U.S.C. 154(b) by 20 days.

(21) Appl. No.: 15/748,020

(22) PCT Filed: Jul. 22, 2016

(86) PCT No.: PCT/EP2016/067568
§ 371 (c)(1),
(2) Date: Jan. 26, 2018

(87) PCT Pub. No.: WO2017/017026
PCT Pub. Date: Feb. 2, 2017

(65) Prior Publication Data
US 2018/0216138 A1     Aug. 2, 2018

(30) Foreign Application Priority Data

Jul. 27, 2015   (EP) .................................. 15306225

(51) Int. Cl.
| C12N 9/02 | (2006.01) |
| C12N 1/21 | (2006.01) |
| C12P 7/06 | (2006.01) |
| C12P 7/16 | (2006.01) |
| C12N 15/52 | (2006.01) |
| C12P 7/18 | (2006.01) |

(52) U.S. Cl.
CPC .............. *C12P 7/06* (2013.01); *C12N 9/0095* (2013.01); *C12N 15/52* (2013.01); *C12P 7/065* (2013.01); *C12P 7/16* (2013.01); *C12P 7/18* (2013.01); *C12Y 118/01002* (2013.01); *Y02E 50/10* (2013.01); *Y02E 50/17* (2013.01)

(58) Field of Classification Search
None
See application file for complete search history.

(56) References Cited

U.S. PATENT DOCUMENTS

| 2003/0175916 A1 | 9/2003 | Sarcabal et al. |
| 2007/0072279 A1 | 3/2007 | Meynial-Salles et al. |
| 2012/0015849 A1 | 1/2012 | Soucaille et al. |
| 2012/0064587 A1* | 3/2012 | Papoutsakis ........... C12N 15/52 435/140 |
| 2014/0004597 A1* | 1/2014 | Chang .................... C12N 15/52 435/252.33 |

FOREIGN PATENT DOCUMENTS

| EP | 2084287 A2 | 8/2009 |
| WO | 9216615 A1 | 10/1992 |
| WO | 2001004324 A1 | 1/2001 |
| WO | 2005073364 A2 | 8/2005 |
| WO | 2008040387 A1 | 4/2008 |

OTHER PUBLICATIONS

Papoutsakis E.T. et al. (2012) Towards a Synthetic Biology of the Stress-Response and the Tolerance Phenotype: Systems Understanding and Engineering of the Clostridium acetobutylicum Stress-Response and Tolerance to Toxic Metabolites. In: Wittmann C., Lee S. (eds) Systems Metabolic Engineering, p. 193-219.*
Uniprot, Accession No. Q97L02, 2015, www.uniprot.org.*
Shen et al., Driving Forces Enable High-Titer Anaerobic 1-Butanol Synthesis in *Escherichia coli*, Appl. Environ. Microbiol., 2011, 77, 2905-15.*
Guo et al., Protein tolerance to random amino acid change, Proc. Natl. Acad. Sci. USA, 2004, 101, 9205-10.*
Stutz et al., GltX from Clostridium saccharobutylicum NCP262: glutamate synthase or oxidoreductase, Biochim. Biophys. Acta., 2004, 1676, 71-82.*
Datebase UNIPROT: "SubName: Full=NADPH-dependent glutamate synthase beta chain {ECO:0000313: EMBL: AAK78740.1};", XP00275983, retrieved from EBI accession No. UNIPROT:Q97L02 Database accession No. Q97L02, Oct. 1, 2001.

(Continued)

*Primary Examiner* — Robert B Mondesi
*Assistant Examiner* — Todd M Epstein
(74) *Attorney, Agent, or Firm* — Lerner, David, Littenberg, Krumholz & Mentlik, LLP

(57) ABSTRACT

The present invention relates to a novel polypeptide having the enzymatic activity of reduction of NADP+ using electrons from reduced ferredoxin (Ferredoxin-NADP+ reductase activity), a polynucleotide having a nucleotide sequence encoding such polypeptide and uses thereof. The invention relates to the modulation of the Ferredoxin NADP+ reductase activity in a microorganism by varying the expression level of the polynucleotide coding for such polypeptide. The invention also relates to the production of commodity chemicals, especially ethanol, n-butanol, 1,3-propanediol, 1,2-propanediol, isopropanol and acetone by fermenting microorganisms wherein their Ferredoxin NADP+ reductase activity is modulated.

5 Claims, 5 Drawing Sheets

Specification includes a Sequence Listing.

(56) References Cited

OTHER PUBLICATIONS

Noelling J. et al., "Genome Sequence and Comparative Analysis of the Solvent-Producing Bacterium Clostridium Acetobutylicum", Journal of Bacteriology, American Society for Microbiology, vol. 183, No. 16, Aug. 1, 2001, pp. 4823-4838.

Erin Garza et al., "Engineering a homobutanol fermentation pathway in Escherichia coli EGO3", Journal of Industrial Microbiology & Biotechnology; Official Journal of the Society for Industrial Microbiology, Springer, Berlin, DE., vol. 39, No. 8, Jul. 10, 2012, pp. 1101-1107.

Li, F. et al., "Coupled Ferredoxin and Crotonyl Coenzyme A (CoA) Reduction with NADH Catalyzed by the Butyryl-CoA Dehydrogenase/Etf Complex from Clostridium kluyveri", Journal of Bacteriology, vol. 190, No. 3, Nov. 9, 2007, pp. 843-850.

Herrmann, G., et al. "Energy Conservation via Electron-Transferring Flavoprotein in Anaerobic Bacteria", Journal of Bacteriology, vol. 190, No. 3, Feb. 1, 2008, pp. 784-791.

Brooks B Bond-Watts et al., "Enzyme mechanism as a kinetic control element for designing synthetic biofuel pathways", Nature Chemical Biology, vol. 7, No. 4, Feb. 27, 2011, pp. 222-227.

Dusséaux, Simon et al., "Metabolic engineering of Clostridium acetobutylicum ATCC 824 for the high-yield production of a biofuel composed of an isopropanol/butanol/ethanol mixture", Metabolic Engineering, vol. 18, Jul. 1, 2013, pp. 1-8.

International Search Report for PCT/EP2016/067568 dated Oct. 21, 2016.

Almeida, et al., "Biodiesel Biorefinery: Opportunities and Challenges for Microbial Production of Fuels and Chemicals from Glycerol Waste", Biotechnology for Biofuels, vol. 5, No. 1, Dec. 2012, 16 pages.

Altaras, et al., "Enhanced Production of (R)-1,2-Propanediol by Metabolically Engineered Escherichia coli", Biotechnology Progress, vol. 16, No. 6, 2000, pp. 940-946.

Anderson, "Growth Requirements of Virus-Resistant Mutants of Escherichia coli Strain "B"", Proceedings of the National Academy of Sciences, vol. 32, No. 5, May 1946, pp. 120-128.

Atsumi, et al., "Metabolic Engineering of Escherichia coli for 1-Butanol Production", Metabolic Engineering, vol. 10, No. 6, Nov. 2008, pp. 305-311.

Baldoma and Aguilar, "Metabolism of L-Fucose and L-Rhamnose in Escherichia coli: Aerobic-Anaerobic Regulation of L-Lactaldehyde Dissimilation", Journal of Bacteriology, vol. 170, No. 1, Jan. 1988, pp. 416-421.

Bennet and San, "Microbial Formation, Biotechnological Production and Applications of 1,2-Propanediol", Applied Microbiology and Biotechnology, vol. 55, No. 1, Jan. 2001, pp. 1-9.

Berezina, et al., "Reconstructing the Clostridial n-Butanol Metabolic Pathway in Lactobacillus Brevis", Applied Microbiology and Biotechnology, vol. 87, No. 2, Jun. 2010, pp. 635-646.

Bernardi and Bernardi, "Complete Sequence of pSC101", Nucleic Acids Research, vol. 12, No. 24, Dec. 1984, pp. 9415-9426.

Bradford, "A Rapid and Sensitive Method for the Quantitation of Microgram Quantities of Protein Utilizing the Principle of Protein-Dye Binding", Analytical Biochemistry, vol. 72, No. 1-2, May 1976, pp. 248-254.

Cherepanov and Wackernagel, "Gene Disruption in Escherichia coli: TcR and KmR Cassettes with the Option of Flp-Catalyzed Excision of the Antibiotic-Resistance Determinant", Gene, vol. 158, No. 1, Dec. 1995, pp. 9-14.

Cintolesi, et al., "Quantitative Analysis of the Fermentative Metabolism of Glycerol in Escherichia coli", Biotechnology and Bioengineering, vol. 109, No. 1, Jan. 2012, pp. 187-198.

Clomburg and Gonzolez, "Metabolic Engineering of Escherichia coli for the Production of 1,2-Propanediol From Glycerol", Biotechnology and Bioengineering, vol. 108, No. 4, Apr. 2011, pp. 867-879.

Cornillot, et al., "The Genes for Butanol and Acetone Formation in Clostridium Acetobutylicum ATCC 824 Reside on a Large Plasmid Whose Loss Leads to Degeneration of the Strain", Journal of Bacteriology, vol. 179, No. 17, Sep. 1997, pp. 5442-5447.

Datsenko and Wanner, "One-Step Inactivation of Chromosomal Genes in Escherichia coli K-12 Using PCR Products", Proceedings of the National Academy of Sciences, vol. 97, No. 12, Jun. 2000, pp. 6640-6645.

Dellomonaco, et al., "Engineered Reversal of the B-Oxidation Cycle for the Synthesis of Fuels and Chemicals", Nature, vol. 476, No. 7360, Aug. 2011, 7 pages.

Demuez, et al., "Complete Activity Profile of Clostridium Acetobutylicum [FeFe]-Hydrogenase and Kinetic Parameters for Endogenous Redox Partners", FEMS Microbiology Letters, vol. 275, No. 1, Jul. 2007, pp. 113-121.

Fontaine, et al., "Molecular Characterization and Transcriptional Analysis of ashE2, the Gene Encoding the NADH-Dependent Aldehyde/Alcohol Dehydrogenase Responsible for Butanol Production in Alcohologenic Cultures of Clostridium Acetobutylicum ATCC 824", Journal of Bateriology, vol. 184, No. 3, Feb. 2002, pp. 821-830.

Girbal, et al., "Homologous and Heterologous Overexpression in Clostridium Acetobutylicum and Characterization of Purified Clostridial and Algal Fe-Only Hydrogenases with High Specific Activities", Applied and Environmental Microbiology, vol. 71, No. 5, May 2005, pp. 2777-2781.

Girio, et al., "Hemicelluloses for Fuel Ethanol: A Review", Bioresource Technology, vol. 101, No. 13, Jul. 2010, pp. 4775-4800.

Heap, et al., "The ClosTron: A Universal Gene Knock-Out System for the Genus Clostridium", Journal of Microbiological Methods, vol. 70, No. 3, Sep. 2007, pp. 452-464.

Gonzalez-Pajuelo, et al., "Metabolic Engineering of Clostridium Acetobutylicum for the Industrial Production of 1,3-Propanediol from Glycerol", Metabolic Engineering, vol. 7, No. 5-6, Sep. 2005, pp. 329-336.

Harrington, et al., "Balanced Branching in Transcription Termination", Proceedings of the National Academy of Sciences, vol. 98, No. 9, Apr. 2001, pp. 5019-5024.

Inui, et al., "Expression of Clostridium Acetobutylicum Butanol Synthetic Genes in Escherichia coli", Applied Microbiology and Biotechnology, vol. 77, No. 6, Jan. 2008, pp. 1305-1316.

Jang, et al., "Enhanced Butanol Production Obtained by Reinforcing the Direct Butanol-Forming Route in Clostridium Acetobutylicum", MBio, vol. 3, No. 5, Nov. 2012, 9 pages.

Jarboe, et al., "Development of Ethanologenic Bacteria", InBioFuels 2007, 2007, 25 pages.

Jiang, et al., "Disruption of the Acetoacetate Decarboxylase Gene in Solvent-Producing Clostridium Acetobutylicum Increases the Butanol Ratio", Metabolic Engineering, vol. 11, No. 4-5, Jul. 2009, pp. 284-291.

Keseler, et al., "EcoCyc: A Comprehensive Database Resource Escherichia coli", Nucleic Acids Research, vol. 33, Jan. 2005, pp. D334-D337.

Kim, et al., "Construction of an Escherichia coli K-12 Mutant for Homoethanologenic Fermentation of Glucose or Xylose Without Foreign Genes", Applied and Environmental Microbiology, vol. 73, No. 6, Mar. 2007, pp. 1766-1771.

Lau, et al., "Comparing the Fermentation Performance of Escherichia coli KO11, Saccharomyces Cerevisiae 424A (LNH-ST) and Zymomonas Mobilis AX101 for Cellulosic Ethanol Production", Biotechnology for Biofuels, vol. 3, No. 1, Dec. 2010, 10 pages.

Matsuoka and Kimura, "Glutamate Synthase from Bacillus Subtilis PCI 219", The Journal of Biochemistry, vol. 99, No. 4, Apr. 1986, pp. 1087-1100.

Mermelstein, et al., "Expression of Cloned Homologous Fermentative Genes in Clostridium Acetobutylicum ATCC 824", Nature Biotechnology, vol. 10, No. 2, Feb. 1992, 6 pages.

Meynial-Salles, et al., "New Tool for Metabolic Pathway Engineering in Escherichia coli: One-Step Method to Modulate Expression of Chromosomal Genes", Applied and Environmental Microbiology, vol. 71, No. 4, Apr. 2005, pp. 2140-2144.

Nolling, et al., "Genome Sequence and Comparative Analysis of the Solvent-Producing Bacterium Clostridium Acetobutylicum", Journal of Bacteriology, vol. 183, No. 16, Aug. 2001, pp. 4823-4838.

(56) References Cited

OTHER PUBLICATIONS

Norrander, et al., "Construction of Improved M13 Vectors Using Oligodeoxynucleotide-Directed Mutagenesis", Gene, vol. 26, No. 1, Dec. 1983, pp. 101-106.
Nielsen, et al., "Engineering Alternative Butanol Production Platforms in Heterologous Bacteria", Metabolic Engineering, vol. 11, No. 4-5, Jul. 2009, pp. 262-273.
Papoutsakis, Eleftherios, "Engineering Solventogenic Clostridia", Current Opinion in Biotechnology, vol. 19, No. 5, Oct. 2008, pp. 420-429.
Perutka, et al., "Use of Computer-Designed Group II Introns to Disrupt *Escherichia coli* DExH/D-box Protein and DNA Helicase Genes", Journal of Molecular Biology, vol. 336, No. 2, Feb. 2004, pp. 421-439.
Saint-Amans, et al., "Regulation of Carbon and Electron Flow in Clostridium Butyricum VPI 3266 Grown on Glucose-Glycerol Mixtures", Journal of Bacteriology, vol. 183, No. 5, Mar. 2001, pp. 1748-1754.
Sanchez-Rivera, et al., "Influence of Environmental Factors in the Production of R(−)-1,2-Propanediol by Clostridium Thermosaccharolyticum", Biotechnology Letters, vol. 9, No. 7, Jul. 1987, pp. 449-454.
Saxena, et al., "Microbial Production of 1,3-Propanediol: Recent Developments and Emerging Opportunities", Biotechnology Advances, vol. 27, No. 6, Nov. 2009, pp. 895-913.
Saxena, et al., "Microbial Production and Applications of 1,2-Propanediol", Indian Journal of Microbiology, vol. 50, No. 1, Mar. 2010, pp. 2-11.
Schaefer, et al., "Automated Sampling Device for Monitoring Intracellular Metabolite Dynamics", Analytical Biochemistry, vol. 270, No. 1, May 1999, pp. 88-96.
Shen, et al., "Driving Forces Enable High-Titer Anaerobic 1-Butanol Synthesis in *Escherichia coli*", Applied and Environmental Microbiology, Mar. 2011, 11 pages.
Steen, et al., "Metabolic Engineering of *Saccharomyces cerevisiae* for the Production of N-Butanol", Microbial Cell Factories, vol. 7, No. 1, Dec. 2008, 8 pages.
Tang, et al., "Microbial Conversion of Glycerol to 1,3-Propanediol by an Engineered Strain of *Escherichia coli*", Applied and Environmental Microbiology, vol. 75, No. 6, Mar. 2009, pp. 1628-1634.
Tracy, Bryan, "Improving Butanol Fermentation to Enter the Advanced Biofuel Market", vol. 3, No. 6, Dec. 2012, 3 pages.
Tran-Din and Gottschalk, "Formation of D(−)-1,2-Propanediol and D(−)-Lactate from Glucose by Clostridium Sphenoides Under Phosphate Limitation", Archives of Microbiology, vol. 142, No. 1, Jun. 1985, pp. 87-92.
Trinh, et al., "Elucidating Mechanisms of Solvent Toxicity in Ethanologenic *Escherichia coli*", Biotechnology and Bioengineering, vol. 106, No. 5, Aug. 2010, pp. 721-730.
Vanoni and Curti, "Glutamate Synthase: A Complex Iron-Sulfur Flavoprotein", Cellular and Molecular Life Sciences CMLS, vol. 55, No. 4, Apr. 1999, pp. 617-638.
Vasconcelos, et al., "Regulation of Carbon and Electron Flow in Clostridium Acetobutylicum Grown in Chemostat Culture at Neutral pH on Mixtures of Glucose and Glycerol", Journal of Bacteriology, vol. 176, No. 5, Mar. 1994, pp. 1443-1450.
Xu, et al., "Metabolism in 1,3-Propanediol Fed-Batch Fermentation by a D-Lactate Deficient Mutant of Klebsiella Pneumoniae", Biotechnology and Bioengineering, vol. 104, No. 5, Dec. 2009, pp. 965-972.
Yu, et al., "Effects of Different Replicons in Conjugative Plasmids on Transformation Efficiency, Plasmid Stability, Gene Expression and N-Butanol Biosynthesis in Clostridium Tyrobutyricum", Applied Microbiology and Biotechnology, vol. 93, No. 2, Jan. 2012, pp. 881-889.
Angov, et al., "Heterologous Protein Expression is Enhanced by Harmonizing the Codon Usage Frequencies of the Target Gene with Those of the Expression Host", PLoS One, vol. 3, No. 5, May 2008, 10 pages.
Girbal and Soucaille, "Regulation of Solvent Production in Clostridium Acetobutylicum", Trends in Biotechnology, vol. 16, No. 1, Jan. 1998, pp. 11-16.
Singhal RK, Krishnan IS, Dua RD. Stabilization, purification, and characterization of glutamate synthase from Clostridium pasteurianum. Biochemistry. Sep. 1, 1989;28(19):7928-35.

* cited by examiner

US 10,760,100 B2

POLYPEPTIDE HAVING FERREDOXIN-NADP+ REDUCTASE ACTIVITY, POLYNUCLEOTIDE ENCODING THE SAME AND USES THEREOF

CROSS-REFERENCE TO RELATED APPLICATIONS

The present application is a national phase entry under 35 U.S.C. § 371 of International Application No. PCT/EP2016/067568, filed Jul. 22, 2016, published as International Publication No. WO 2017/017026 A1, which claims priority from European Patent Application No. 15306225.2, filed Jul. 27, 2015, all of which are incorporated herein by reference.

FIELD OF THE INVENTION

The present invention relates to a novel polypeptide having the enzymatic activity of reduction of NADP+ using electrons from reduced ferredoxin (Ferredoxin-NADP+ reductase activity), a polynucleotide having a nucleotide sequence encoding such polypeptide and uses thereof.

More particularly, the invention relates to the modulation of the Ferredoxin-NADP+ reductase activity in a microorganism by varying the expression level of the polynucleotide coding for such polypeptide.

The present invention also relates to the production of commodity chemicals, especially ethanol, n-butanol, isopropanol, acetone, 1, 3-propanediol, 1,2-propanediol, by fermenting microorganisms wherein the Ferredoxin-NADP+ reductase activity is modulated.

PRIOR ART

1) N-Butanol Production:

N-butanol is naturally produced in slow-growing native hosts, that belong to genus *Clostridium*, as a mixture with acetone and ethanol in a biphasic fermentation, especially the most well-known *C. acetobutylicum* (Cornillot et al. 1997, Girbal and Soucaille 1998, Fontaine et al. 2002). Even if the acetone-butanol-ethanol (ABE) fermentation was one of the first large scale industrial fermentation and despite the long research history into the fermentation process, obstacles still remain today. As *clostridia* are strict anaerobes, the growth condition must remain anaerobic and the growth rate is significantly slow compared to many of the aerobic microorganisms resulting in low butanol production rate. Moreover, the use of *Clostridium* acetobutylicum or *C. beijerinckii* strains (which are the most studied) in continuous process are be limited due to the risk of degeneration of the strains.

Advances in genetic manipulation of *clostridia* have recently led to large increases in titer and productivity (Papoutsakis 2008, Soucaille 2007, Jiang et al. 2009, Tracy 2012). Up to now, the best engineered *C. acetobutylicum* ATCC 824 strain for the production of n-butanol at high yield and titre was obtained using a combination of a disruption of particular genes involved in acids production with the overexpression of the AdhE1$^{D485G}$ alcohol dehydrogenase variant. A maximal concentration of 18.4 g/l n-butanol was produced from glucose in batch culture at a yield of 0.28 g/g glucose with low amounts of acetone, ethanol, acetate and butyrate (2 g/L, 3 g/L, 2 g/L and 4.3 g/L respectively) (Jang et al. 2012). As one of drawbacks of the *Clostridia* n-butanol production is the co-synthesis of acetone, which cannot be used as fuel source, several studies were focused on strategies to circumvent carbon lost to this product. One alternative was to overexpress the primary/secondary alcohol dehydrogenase from *C. beijrinckii* NRRL B-593 encoded by the sadh$_{B-593}$ gene to reduce acetone into isopropanol. The engineered *C. acetobutylicum* 824 Δbuk strain overexpressing the sadh gene with the acetone pathway was able to produce, from glucose, 21 g/L of IBE mixture at a yield of 0.34 g/g, in controlled batch fermentations, without any acetone traces (Dusséaux et al. 2013). Another reported alternative was the engineering of *Clostridium tyrobutyricum* ATCC 25755, a non solventogenic acidogen, by expressing the AdhE2 alcohol dehydrogenase from *C. acetobutylicum*. The recombinant strain grown, in batch conditions at pH 6, on RCM medium with mannitol as carbon source, was able to produce 20.5 g/L of butanol at a yield of 0.33 g/g in presence of 6 g/L of butyric acid (Yu et al. 2012).

To overcome some of the problems associated with clostridial butanol production process, the clostridial butanol fermentation pathway was introduced into several heterologous organisms such as *E. coli* B or K12 (Atsumi et al. 2007, Inui et al. 2008, Garza et al. 2012) *Saccharomyces cerevisiae* (Steen et al. 2008), *Bacillus subtilis*, *Pseudomonas putida* (Nielsen et al. 2009) or *Lactobacillus brevis* (Berezina et al. 2010) to convert acetylCoA to butanol. Reported results showed that the seven *C. acetobutylicum* native genes of the pathway (thl, hbd, crt, bcd, etfAB and adhE2) are functional whatever the heterologous organism is, but the final butanol titer is rather low. Neither species could produce more than 1 g/l of butanol.

Two bottlenecks limiting the 1-butanol production were identified: i) the pathway requires four moles of NADH to produce 1 mole of 1-butanol in the engineered *E. coli* strain, and balancing NADH needs an active pyruvate dehydrogenase complex under anaerobic conditions while this enzyme is normally inactive due to inhibition by NADH (Atsumi et al., 2007, Garza et al. 2012) ii) the activity of the butyryl-CoA dehydrogenase (Bcd) catalysing the conversion of crotonyl-CoA to butyryl-CoA was low even if the etfA and etfB genes were expressed simultaneously with bcd (Inui M. et al. 2008, Berezina et al. 2010), and this enzyme complex produced reduced ferredoxin that has to be oxidized in *E. coli* for the reaction to proceed as previously described (Li et al. 2008). This last bottleneck can be overcome by using an alternative enzyme to replace Bcd, a NADH dependent trans-enoyl-CoA reductase (Ter) (Bond-Watts et al. 2011, Shen et al. 2011). The combination of the overexpression of the six following genes atoB (*E. coli*), adhE2, crt, hbd (*C. acetobutylicum*), fdh (*C. boidini*) and Ter (*T. denticola*) into the JCL 299 *E. coli* strain (ΔldhA, ΔadhE, ΔfrdBCΔpta) led up to 15 g/L of butanol produced, after 75 hours of anaerobic culture in flasks containing 2% glucose terrific broth medium (Shen et al. 2011).

Another notable alternative to produce n-butanol was the engineering of the endogenous β-oxidation cycle in *E. coli* by introducing keys genetic modifications to eliminate the regulatory mechanism that represses the genes involved in β-oxidation (fadR atoC(c) crp*ΔarcA), combined with the elimination of competitive native fermentative pathways (ΔadhE, Δpta, ΔfrdA, ΔyqhD, ΔeutE) and the overexpression of both YqeF (a predicted acyl transferase) and FucO (a L 1.2 propanediol oxidoreductase). Grown in bioreactor containing mineral medium supplemented with 5% glucose under micro-anaerobic conditions (5% dissolved oxygen), the engineered *E. coli* strain produced 14 g/l of n-butanol at a yield of 0.33 g/g glucose) (Dellomonaco et al. 2011). However, it should be consider that this system level approach is limited by the ill-defined of the individual components of the engineered pathway.

2) 1.3 Propanediol Production:

1.3-propanediol (1.3Pdiol) is an important chemical widely used as a monomer in the production of polymers (polytrimethylene terephtalate just to cite an example). For a long time, 1.3Pdiol has been produced through chemical ways which generated huge cost and toxic products. Many microorganisms belonging to the genus *Klebsiella, Citrobacter, Lactobacilli* and *Clostridium* were found to naturally produce 1.3Pdiol from glycerol, an abundant waste metabolite produced in the biodiesel industry (Saxena et al. 2009). Most natural producers catabolize glycerol in two parallel pathways: i) the oxidation of glycerol into dihydroxyacetone then transformed into glyceraldehyde-3-phosphate and further to pyruvate, which in turn produces various byproducts and NADH2 reducing equivalent and ii) the reduction of glycerol into 3-hydroxypropionaldehyde (HPA) by a glycerol dehydratase followed by the reduction of HPA into 1.3Pdiol by an NADH dependent 1.3 Pdiol dehydrogenase, and thereby regenerating NAD+. Reduced co-enzymes produced in the oxidative pathway are required for the reductive pathway maintaining the redox balance of the cell.

Depending of the microorganisms, the 1.3Pdiol production can be absolute anaerobic (*Clostridium butyricum*), microaerobic or aerobic (*Klebsiella* or *Citrobacter*) (Saint Amans et al. 2001, Saxena et al. 2009). Whatever the conditions, the methods and the natural producers are, the glycerol 1.3Pdiol conversion yield oscillated from 0.51 to 0.64 mol/mol, and a final 1.3Pdiol titer up to 102 g/L can be reached in fed-batch conditions (Xu et al. 2009, Almeida et al. 2012). Non-natural 1.3 propanediol producers like *E. coli* or *C. acetobutylicum* were also engineered by expressing the genes of the 1.3 Pdiol pathway. For example, the expression of the 1.3Pdiol pathway from *C. butyricum* into *C. acetobutylicum*, naturally unable to grow on glycerol as the sole carbon source, led to the production of 84 g/l of 1.3Pdiol at a yield of 0.65 mol/mol (Meynial-Salles et al. 2005). Finally, the combination of the overexpression of the B12 independent glycerol dehydratase from *C. butyricum* to YqhD (a NADPH 1.3 propanediol dehydrogenase from wild type *E. coli*) in *E. coli* (Tang et al. 2009) allowed the production of 104 g/l of 1.3 Pdiol in a two stages (aerobic and anaerobic) process, at a conversion yield of glycerol to 1.3Pdiol of 90.2% (g/g) during the anaerobic phase, a value that would mean that 1.12 mole of 1,3 propanediol are produced from 1 mole of glycerol which is impossible.

3) Propylene Glycol Production:

1.2 propanediol or propylene glycol is a three-carbon diol with stereogenic center at the central carbon, widely used as a commodity chemical. It is a constituent of unsaturated polyesters resins, non-ionic detergents, cooling, anti-freeze or de-icing fluid for aircraft. It can be used too as an additive in nutrition products and cosmetics. Produced up to now by a petrochemical way using a propylene oxide hydration process, this method has several drawbacks linked to the large amounts of water consumed and the generation of waste streams containing environmental contaminants (Saxena et al. 2010).

As regards the biological way, wide ranges of microorganisms (both bacteria and yeasts) are known to produce 1.2 propanediol i) from common sugars such as glucose or xylose which are metabolized by the glycolysis pathway into dihydroxyacetone phosphate (DHAP) and, then, into methyl glyoxal the precursor of 1.2 propanediol (Bennett and San 2001) or ii) from deoxysugars (fucose or rhamnose) like in *E. coli* which led to the synthesis of (S)-1.2 propanediol (Baldoma and Aguilar 1988).

*Clostridium sphenoïdes* (Tran-Din and Gottschalk 1985) and *Thermoanaerobacterium thermosaccharolyticum* were described as the best 1.2 propanediol natural producers, *T. thermosaccharolyticum* being able to produce up to 9 g/l of (R)-1.2 propanediol from glucose, with a yield of 0.47 mol/mol glucose consumed (Sanchez-Riviera et al. 1987).

Metabolic engineering of the 1.2 propanediol pathway in *E. coli* was performed to force the cells to produce 1.2 propanediol from common sugars like glucose at the place of deoxysugars. A first strategy combining i) the overexpression of the key enzymes involved into DHAP to 1.2 propanediol conversion, ii) to the elimination of competing pathways and iii) to a glucose fed batch fermentation resulted in an engineered *E. coli* strain producing 4.5 g/l of (R)-1.2 propanediol, at a yield of 0.45 mol/mol glucose consumed (Altaras and Cameron 2000). A more recent study used the introduction of keys rational modifications of the central metabolism to link the growth and the glucose consumption to the 1.2 propanediol pathway to favour in vivo metabolic evolution (Meynial-Salles et al. 2005). After adaptive evolution under appropriate culture conditions and reisolation of evolved clones from the population, the evolved engineered *E. coli* ΔtpiA, ΔpflAB, ΔadhE, ΔldhA, ΔgloA, ΔaldA, ΔaldB Δedd strain, grown in batch conditions on glucose mineral medium, produced 1.8 g/l of 1.2 propanediol at a yield of 0.85 mol/mol.

Finally, *E. coli* was rationally engineered to produce 1.2 propanediol from glycerol. Grown in controlled fermenters, the best resulting strain was capable of producing 5.6 g/l of 1.2 propanediol at a yield of 0.25 mol/mol glycerol consumed (Clomburg and Gonzalez 2011). The 1.2 propanediol production was also demonstrated on crude glycerol generated from the biodiesel industry with equivalent performance than on pure glycerol.

4) Ethanol Production:

Several metabolic and evolutionary engineering techniques have been applied to develop efficient strains producing ethanol at a high yield and titer from a wide range of substrates. The most studied organisms are i) *Saccharomyces cerevisiaie* and *Zymomonas mobilis* which naturally produce ethanol at high yield and efforts are concentrated on broadening substrate range and ii) *E. coli* in which efforts are concentrated on ethanol yield improvement (Girio et al. 2010). *E. coli* B strains producing anaerobically ethanol up to 45 g/L have already been obtained (Jarboe et al. 2007). These strains were constructed by either improving the endogenous pathway to ethanol (directed evolution performed on pyruvate dehydrogenase) or introducing a heterologous pathway composed of pyruvate decarboxylase and alcohol dehydrogenase (from *S. cerevisiae* or *Z. mobilis*). In best cases, ethanol was produced at yields of 90% predicted maximum, and these approaches have already been patented (for instance Ingram et al. 1992 WO 9216615; Kim et al. 2007). The poor tolerance of *E. coli* to ethanol remains the major factor that limits final titers, and seems to be linked in particular to the ethanol inhibition of the pyruvate decarboxylase (Trinh et al. 2010).

In recent years, efforts were focused on developing strains i) able to co-utilize C6 (glucose, galactose) and C5 (xylose and arabinose) sugars, the components present in lignocellulosic biomass hydrolysates or ii) growing on glycerol, a cheap and abundant carbon source. For example, the overexpression in *E. coli* K12 of both the glycerol dehydrogenase (glyDh) and the dihydroacetonekinase (DHAK), two enzymes specific of glycerol utilization, enabled the production of nearly 20 g/L of ethanol from crude glycerol during pH controlled anaerobic fermentation, at a yield of 0.92 mol ethanol produced per mole of glycerol consumed (Cintolesi et al. 2012).

Finally, the fermentation performances of the three best engineered E. coliKO11, Z. mobilisAX101 and S. cerevisiae 424A strains were compared on cellulosic hydrolysates (Lau et al. 2010). The results indicated that the metabolic pathway of E. coliKO101 and Z. mobilis was more effective to produce ethanol from consumed sugars relative to the S. cerevisiae 424A pathway. However, in both bacteria xylose consumption was strongly affected in comparison to S. cerevisiae 424A, which was able to use both glucose and xylose from cellulosic hydrolysates.

DESCRIPTION OF THE INVENTION

In a first embodiment, the invention concerns a modified microorganism having modulated Ferredoxin NADP+ reductase enzymatic activity, wherein the activity of the polypeptide having at least 70% identity with the sequence of SEQ ID No 1 is attenuated or enhanced.

More particularly, in such a first embodiment the modified microorganism having Ferredoxin NADP+ reductase enzymatic activity, is such that the activity of the polypeptide having at least 70% identity with the sequence of SEQ ID No 1 is enhanced in comparison with the non-modified microorganism.

The modified microorganism contains or expresses a polypeptide having at least 70% identity with the sequence of SEQ ID No 1 and is characterized in that the Ferredoxin NADP+ reductase enzymatic activity of such polypeptide is enhanced in comparison with the non-modified microorganism.

The polypeptide has at least 70%, particularly 75%, 80%, 81%, 82%, 83%, 84%, 85%, 86%, 87%, 88%, 89%, 90%, 91%, 92%, 93%, 94%, 95%, 96%, 97%, 98%, or 99% or even 100% identity with the sequence of SEQ ID No 1.

In a second embodiment the invention concerns a microorganism according to the first embodiment with attenuated Ferredoxin NADP+ reductase enzymatic activity wherein the expression of the native gene coding for the polypeptide having at least 70% identity with the sequence of SEQ ID No 1 is attenuated.

In a third embodiment, the invention concerns a microorganism according to the second embodiment, wherein production of acetone and acetate is enhanced.

In a forth embodiment, the present invention relates to a microorganism according to first embodiment with enhanced Ferredoxin NADP+ reductase enzymatic activity, wherein a polynucleotide coding for the polypeptide having at least 70% identity with the sequence of SEQ ID No 1 is overexpressed.

In a fith embodiment, the invention is directed to a microorganism according to the forth embodiment wherein it contains at least one modification to produce ethanol.

In a sixth embodiment, the invention concerns a microorganism according to fith embodiment, wherein the at least one modification to produce ethanol comprises:
  Enhancement of the expression of at least one of the following genes: pfor, fdx, udhA
  and/or
  Attenuation of the expression of at least one of the following genes: aceE, aceF, lpd, pflA, pflB, poxB frdABCD, ldhA, mgsA, ackA, pta and iscR.

In a seventh embodiment, the present invention deals with a microorganism according to the forth embodiment wherein it contains at least one modification to produce n-butanol.

In an eighth embodiment, the invention concerns a microorganism according to seventh embodiment, wherein the at least one modification to produce n-butanol comprises:
  Enhancement of the expression of at least one of the following genes: pfor, fdx, atoB, hbd, crt, bcd, effA, etfB, adhE2, udhA,
  and/or
  Attenuation of the expression of at least one of the following genes: aceE, aceF, lpd, NIA, pfl B,frdABCD, adhE, ldhA, mgsA, ackA, pta, and iscR In a ninth embodiement, the invention relates to a microorganism according to forth embodiment wherein it comprises at least one modification to produce 1, 3 propanediol from glycerol.

In a tenth embodiment, the invention concerns a microorganism according to ninth embodiment, wherein the at least one modification to produce 1, 3 propanediol comprises:
  Enhancement of the expression of at least one of the following genes: pfor, fdx, pntAB, dhaB1, dhaB2, yqhD
  and/or
  Attenuation of the expression of at least one of the following genes: aceE, aceF, lpd, poxB, ndh, aldA, aldB, ldhA, pflA, pflB, adhE, iscR, glpA and glpD.

According to a eleventh embodiment, the invention concerns a microorganism according to forth embodiment wherein it comprises at least one modification to produce 1, 2 propanediol.

In a twelth embodiment, the invention relates to a microorganism according to eleventh embodiment, wherein the at least one modification to produce 1, 2 propanediol comprises:
  Attenuation of the expression of at least one of the following genes: ptsG, ptsH ptsI, crr, edd, eda, gloA, aceE, aceF, lpd, aldA, aldB, ldhA, pflA, pflB, adhE, tpiA, gapA, pykA, pykF, ackA, pta, poxB, arcA and ndh,
  And/or
  Enhancement of the expression of at least one of the following genes: pfor, fd, pntAB, gapN, galP, glk, ppsA, mgsA, sadh, yqhD, yafB, ydhF, ycdW, yqhE, yeaE, yghZ, yajO, tas, ydjG, ydbC, gldA,fucO.

In a thirteenth embodiment, the present invention further relates to method for modulating the Ferredoxin NADP+ reductase enzymatic activity in a microorganism, wherein the activity of the polypeptide having at least 70% identity with the sequence of SEQ ID No 1 is enhanced or attenuated in the said microorganism.

In a particular embodiment, the percentage of identity is of at least 75%, at least 80%, at least 85%, at least 90%, at least 92%, at least 93%, at least 94%, at least 95%, at least 96%, at least 97%, at least 98%, at least 99% with the sequence of SEQ IDNo 1. In a further particular embodiment the polypeptide corresponds to SEQ ID No 1.

In a fourteenth embodiment, the invention relates to a method according to thirteenth embodiment, wherein the Ferredoxin NADP+ reductase enzymatic activity is enhanced by overexpressing a polynucleotide coding for the polypeptide having at least 70% identity with the sequence of SEQ ID No 1.

In a particular embodiment, the percentage of identity is of at least 75%, at least 80%, at least 85%, at least 90%, at least 92%, at least 93%, at least 94%, at least 95%, at least 96%, at least 97%, at least 98%, at least 99% with the sequence of SEQ IDNo 1. In a further particular embodiment the polypeptide corresponds to SEQ ID No 1.

The invention also relates to a fifteenth embodiment which relates to a method according to thirteenth embodiment, wherein the Ferredoxin NADP+ reductase enzymatic activity is attenuated by attenuating the expression of a polynucleotide coding for the polypeptide having at least 70% identity with the sequence of SEQ ID No 1.

In a particular embodiment, the percentage of identity is of at least 75%, at least 80%, at least 85%, at least 90%, at least 92%, at least 93%, at least 94%, at least 95%, at least 96%, at least 97%, at least 98%, at least 99% with the sequence of SEQ IDNo 1. In a further particular embodiment the polypeptide corresponds to SEQ ID No 1.

Also, the invention relates in a sixteenth embodiment to a method for preparing ethanol wherein the microorganism according to fifth or sixth embodiment is grown in an appropriate culture medium comprising a source of carbon and the ethanol is recovered.

In a seventeenth embodiment the invention relates to a method for preparing n-butanol wherein the microorganism according to seventh or eighth embodiment is grown in an appropriate culture medium comprising a source of carbon and the n-butanol is recovered.

In an eighteenth embodiment, the invention relates to a method for preparing 1, 3 propanediol wherein the microorganism according to ninthe or tenth embodiment is grown in an appropriate culture medium comprising a source of carbon and the 1, 3-propanediol is recovered.

In a nineteenth embodiment, the present invention concerns a method for preparing 1, 2 propanediol wherein the microorganism according to eleventh or twelfth embodiment is grown in an appropriate culture medium comprising a source of carbon and the 1, 2-propanediol is recovered.

Also, in twentieth embodiment the present invention relates to the use of a microorganism according to fifth or sixth embodiment to produce ethanol.

In a twentyfirst embodiment, the present invention relates to the use of a microorganism according to seventh or eighth embodiment to produce n-butanol.

Also, in a twentysecond embodiment the present invention discloses the use of microorganism according to nineth or tenth embodiment to produce 1,3 propanediol.

Eventually, the present invention, in a twentythirth embodiment relates to the use of microorganism according to eleventh or twelfth embodiment to produce 1,2 propanediol.

The present invention concerns an isolated polypeptide having a Ferredoxin-NADP+ reductase enzymatic activity comprising the sequence of SEQ ID NO 1, a fragment or homologous sequence thereof.

The invention also related to a polypeptide having at least 70% identity with the sequence of SEQ ID No 1 having Ferredoxin NADP+ reductase enzymatic activity.

The invention also relates to the use of a polypeptide having at least 70% identity with the sequence of SEQ ID No 1 for the reduction of NADP+ using electrons from reduced ferredoxin in a microorganism or in the culture medium of a microorganism.

The invention also provides a polynucleotide comprising a sequence coding for said polypeptide. Inventors report the identification of a gene from *C. acetobutylicum* encoding a protein having a Ferredoxin-NADP+ reductase activity. This gene was previously known as the CA_C0764 gene annotated as coding for a potential small subunit of glutamate synthase (Nölling et al, 2001). Glutamate synthase (GOGAT) are heterodimeric proteins composed of a large alpha subunit and a small beta subunit that catalysed the NAD(P)H dependent conversion of alpha-ketoglutarate to glutamate. This protein has been purified from *Clostridium pasteurianum* (Singhal R K et al, 1989) and *Bacillus subtilis* (Matsuoka K, and Kimura K, 1986), and was shown to be a complex iron-sulfur flavoprotein (Vanoni M and Curti B, 1999). No association of glutamate synthase with a Ferredoxin-NADP+ reductase activity has ever been reported in the literature.

The invention is furthermore related to an expression cassette comprising said polynucleotide under the control of regulatory elements functional in a host cell and to a transformation vector comprising said cassette or said polynucleotide.

The invention also provides a modified microorganism having modulated Ferredoxin-NADP+ reductase enzymatic activity wherein activity of the polynucleotide of the invention is attenuated or enhanced.

It is one object of the present invention to use the new knowledge of a gene encoding for Ferredoxin-NADP+ reductase protein from *C. acetobutylicum* to design microorganisms with enhanced Ferredoxin-NADP+ reductase activity and new metabolic pathways for the production of either ethanol, n-butanol, 1,3 propanediol or 1, 2 propanediol. These microorganisms use new metabolic pathways to convert i) glucose to either ethanol, n-butanol, or 1, 2 propanediol, and ii) glycerol to 1,3 propanediol. In certain embodiments of the invention, microorganisms with enhanced Ferredoxin-NADP+ reductase activity are further modified to enhance i) the soluble transhydrogenase activity for the production of either ethanol or n-butanol at high yield or ii) the membrane bound transhydrogenase for the production of either 1,3 propanediol or 1, 2 propanediol at high yield. Additionnally, a method for preparing either ethanol, n-butanol, 1,3 propanediol or 1, 2 propanediol wherein said microorgansims are grown in appropriate growth medium and either ethanol, n-butanol, 1,3 propanediol or 1, 2 propanediol are recovered is provided.

It is also an object of the present invention to use the new knowledge of the gene encoding for the Ferredoxin-NADP+ reductase protein from *C. acetobutylicum* to design a microorganism with attenuated Ferredoxin-NADP+ reductase activity useful for the production of acetone. Attenuation of said gene coding for Ferredoxin-NADP+ reductase provides a *C. acetobutylicum* strain able to produce butanol at a lower yield and acetone at higher yield, therefore increasing the acetone productivity of the process. A method for preparing acetone wherein said microorgansims are grown in appropriate growth medium and acetone is recovered is provided.

The invention is also related to a method for modulating the Ferredoxin-NADP+ reductase enzymatic activity in a microorganism, wherein activity of the polypeptide of the invention is enhanced or attenuated in said microorganism.

DETAILED DESCRIPTION OF THE INVENTION

The present invention is related to an isolated polypeptide having a Ferredoxin-NADP+ reductase enzymatic activity comprising the sequence of SEQ ID No 1, a fragment or homologous sequence thereof.

```
SEQ ID No 1:
MDNPNLLSEEANRCLLCKNPRCKANCPINTPIPEIISLYKEGKIMEAGEI
LFNNNPLSVICSLVCIHEDQCKGNCVRGIKSEPIKFHEIEEEISEKYLKE
```

```
-continued
AKLKNVQKDKDRIAIVGGGPAGITVAFVLANKGYNVTIFEAHDKIGGVLR

YGIPEYRLTKKLVDKLEERLIEVGVKIRPNTVIGPVISLDRLLEDSYKAV

FIGTGVWNPKTLDVKGETLGNVHFAIDYLKSPESYRLGKKVAVIGAGNVA

MDAARTAKRNGAEVTILYRKSFNEMPASKQEIRETKEDGVEFKLFRAPIE

ITEEGIKVAFTENVTDAEGKIRTKIIEGKEEFFECDSVVVAVSQAPKDNI

VSNTTGLDTKWGLIVTDEKGNTTKKGTFACGDVVTGAKTVVEAAAQAKVV

AETIDEYCKNN
```

As used herein, the following terms may be used for interpretation of the claims and specification.

According to the invention, the term "polypeptide" refers to peptide or protein which comprises a sequence of two or more amino-acids linked with peptide bonds.

The term "isolated" refers to a protein or DNA sequence that is removed from at least one component with which it is naturally associated.

The term "Ferredoxin-NADP+ reductase" refers to a polypeptide responsible for an enzyme activity that catalyzes the reduction of NADP+ using electrons from reduced ferredoxin. Such an enzyme activity was described in *C. acetobutylicum* by Vasconcelos et al (1994) and methods to measure this enzyme activity were provided.

The terms "enzyme activity" and "enzymatic activity" are used interchangeably and refer to the ability of an enzyme to catalyse a specific chemical reaction, for example the reduction of NADP+ using electrons from reduced ferredoxin for Ferredoxin-NADP+ reductase enzyme activity.

The isolated polypeptide of the present invention can be obtained from microorganisms having Ferredoxin-NADP+ reductase activity, for example by using the purification procedure as described in the following examples. Microorganisms that can be used to isolate the polypeptide include, but are not limited to, *C. acetobutylicum*.

The term "comprising the sequence of SEQ ID No 1" means that the amino-acid sequence of the polypeptide may not be strictly limited to SEQ ID No 1 but may contain additional amino-acids. The term "a fragment of SEQ ID No 1" means that the sequence of the polypeptide may include less amino-acid than SEQ ID No 1 but still enough amino-acids to confer Ferredoxin-NADP+ reductase activity. It is well known in the art that a polypeptide can be modified by substitution, insertion, deletion and/or addition of one or more amino-acids while retaining its enzymatic activity. For example, substitutions of one amino-acid at a given position by a chemically equivalent amino-acid that do not affect the functional properties of a protein are common. For the purposes of the present invention, substitutions are defined as exchanges within one of the following groups:

Small aliphatic, non-polar or slightly polar residues: Ala, Ser, Thr, Pro, Gly

Polar, negatively charged residues and their amides: Asp, Asn, Glu, Gln

Polar, positively charged residues: His, Arg, Lys

Large aliphatic, non-polar residues: Met, Leu, Ile, Val, Cys

Large aromatic residues: Phe, Tyr, Trp.

Thus, changes which result in substitution of one negatively charged residue for another (such as glutamic acid for aspartic acid) or one positively charged residue for another (such as lysine for arginine) can be expected to produce a functionally equivalent product.

The positions where the amino-acids are modified and the number of amino-acids subject to modification in the amino-acid sequence are not particularly limited. The man skilled in the art is able to recognize the modifications that can be introduced without affecting the activity of the protein. For example, modifications in the N- or C-terminal portion of a protein would not be expected to alter the activity of a protein.

The term "homologous" refers to polypeptides submitted to modifications such as defined above while still retaining the original enzymatic activity.

In a specific embodiment of the invention, the polypeptide of the present invention have at least 70% identity with the sequence of SEQ ID No 1, preferentially at least 80% identity and more preferentially at least 90% identity.

Methods for determination of the percentage of identity between two protein sequences are known from the man skilled in the art. For example, it can be made after alignment of the sequences by using the software CLUSTALW available on the website http://www.ebi.ac.uk/clustalw/ with the default parameters indicated on the website. From the alignment, calculation of the percentage of identity can be made easily by recording the number of identical residues at the same position compared to the total number of residues. Alternatively, automatic calculation can be made by using for example the BLAST programs available on the website http://www.ncbi.nlm.nih.gov/BLAST/ with the default parameters indicated on the website.

In a specific embodiment of the invention, the polypeptide comprises at least 100 contiguous amino-acids from the sequence of SEQ ID No 1, preferentially at least 150, at least 200, at least 250, at least 300, at least 350 or more preferentially at least 400 contiguous amino-acids of the sequence shown in SEQ ID No 1 In another embodiment of the invention, the polypeptide has a polypeptidic sequence strictly identical to the sequence of SEQ ID No 1.

The present invention is also related to a polynucleotide comprising a sequence coding for the polypeptide of the invention.

The term "polynucleotide" refer to a polymer of ribonucleotides (or RNA) or to a polymer of deoxyribonucleotides (or DNA), that is single or double-stranded, optionally containing synthetic, non-natural, or altered nucleotide bases. An isolated polynucleotide in the form of DNA may contain one or more segments of synthetic DNA, genomic DNA or cDNA.

The origin of the polynucleotide is not necessarily the organism where the enzymatic activity is originally measured. Hybridization under different conditions of stringency with a probe that comprises the nucleotide sequence of SEQ ID No 2 can be used to screen a gene library for such polynucleotides by the man skilled in the art. Detailed protocols for hybridization are disclosed in Sambrook et al (1989).

The sequences of such polynucleotides can be extracted from the databases using for example the BLAST programs defined above and searching for homology with the nucleotide sequence of SEQ ID No 2.

```
SEQ ID No 2:
ATGGATAACCCTAATTTATTGTCAGAAGAGGCAAACAGATGCCTACTATG

CAAAAACCCTAGATGTAAAGCAAATTGCCCTATTAATACACCCATACCAG

AAATTATAAGCCTTTATAAAGAAGGAAAAATTATGGAAGCAGGAGAAATT
```

```
-continued
TTATTTAATAACAATCCTCTTTCAGTAATATGCTCATTGGTCTGTATTCA

TGAGGATCAATGTAAGGGAAATTGTGTAAGAGGAATAAAAAGCGAGCCAA

TAAAATTTCACGAGATAGAAGAAGAGATATCAGAGAAGTACTTAAAAGAG

GCCAAGCTTAAGAATGTTCAGAAGGACAAGGATAGAATTGCAATAGTTGG

AGGAGGTCCAGCAGGAATCACAGTTGCATTTGTACTTGCTAATAAAGGCT

ATAATGTTACCATTTTTGAGGCTCACGATAAAATAGGAGGAGTACTTAGA

TATGGTATTCCAGAGTATAGATTGACTAAGAAATTAGTGGATAAGCTTGA

AGAAAGACTTATAGAGGTTGGAGTGAAAATTAGACCTAATACTGTTATTG

GACCAGTTATTTCTTTGGACAGGTTACTTGAAGATTCATATAAGGCAGTA

TTTATTGGAACTGGAGTATGGAATCCAAAAACCTTAGATGTAAAGGGAGA

AACTTTAGGAAATGTTCATTTTGCTATTGATTATTTAAAATCTCCTGAAA

GCTATAGATTAGGAAAAAAGTAGCTGTAATAGGAGCAGGTAATGTTGCC

ATGGATGCTGCAAGAACTGCTAAGAGAAATGGTGCTGAGGTAACAATACT

TTATAGAAAAGCTTTAATGAGATGCCAGCATCAAAACAAGAAATAAGAG

AAACTAAAGAAGATGGAGTAGAGTTTAAATTATTTAGAGCACCAATTGAA

ATAACAGAAGAGGGTATTAAAGTAGCATTTACAGAAAATGTTACAGATGC

AGAAGGAAAAATAAGAACTAAAATTATTGAAGGAAAAGAAGAGTTTTTTG

AGTGTGATTCAGTAGTTGTTGCCGTAAGTCAAGCACCTAAGGATAATATA

GTATCTAATACAACAGGCTTAGATACTAAATGGGGATTAATAGTAACAGA

TGAAAAAGGCAATACAACTAAAAAAGGAACCTTTGCATGTGGAGATGTAG

TTACAGGAGCAAAAACTGTAGTTGAAGCTGCAGCACAAGCAAAAGTAGTT

GCAGAAACTATTGATGAGTATTGCAAGAATAATTAA.
```

Preferred polynucleotides of the present invention are polynucleotides that are at least 80% identical to the nucleotide sequence of SEQ ID No 2. More preferred polynucleotides of the present invention are polynucleotides that are at least 90% identical to the nucleotide sequence of SEQ ID No 2. Even more preferred polynucleotides of the present invention are polynucleotides that are at least 95% identical to the nucleotide sequence of SEQ ID No 2.

In particular, the polynucleotide that comprises the nucleotide sequence of SEQ ID No 2 is included in the invention.

The terms "encoding" or "coding" refer to the process by which a polynucleotide, through the mechanisms of transcription and translation, produces an amino-acid sequence. This process is allowed by the genetic code, which is the relation between the sequence of bases in DNA and the sequence of amino-acids in proteins. One major feature of the genetic code is to be degenerate, meaning that one amino-acid can be coded by more than one triplet of bases (one "codon"). The direct consequence is that the same amino-acid sequence can be encoded by different polynucleotides. As an example, polynucleotide sequences derived from SEQ ID No 2 by degeneracy of the genetic code can also code for the polypeptide sequence of SEQ ID No 1 and are therefore contemplated by the present invention. It is well known from the man skilled in the art that the use of codons can vary according to the organisms. Among the codons coding for the same amino-acid, some can be used preferentially by a given microorganism. It can thus be of interest to design a polynucleotide adapted to the codon usage of a particular microorganism in order to optimize the expression of the corresponding protein in this organism.

The present invention is also related to an expression cassette comprising the polynucleotide of the invention under the control of regulatory elements functional in a host microorganism.

The term "expression" refers to the transcription and translation of a gene sequence leading to the generation of the corresponding protein, product of the gene.

The term "expression cassette" refers to a polynucleotide preferably linked with regulatory elements, such as promoters, enhancers, ribosome binding site or terminator allowing the expression of the gene contained in the polynucleotide inside a suitable host organism. Such regulatory elements can be the own regulatory elements of the gene, but also modified or synthetic elements, to allow a stronger expression of the gene. For example, stronger expression can be obtained by replacing the native promoter of the gene by stronger promoters. For *E. coli* these promoters are for example: lac promoter, tac promoter, trc promoter, lambda cI promoter and GI promoters (Meynial-Salles et al. 2005, Soucaille et al. 2012). For other organisms, the skilled artisan may be able to choose the more adapted promoter.

The term "host microorganism" refers to a microorganism able to receive foreign or heterologous genes or extra copies of its own genes and able to express those genes to produce an active protein product.

The present invention provides for a transformation vector comprising the polynucleotide or the cassette according to the invention.

The term "transformation" refers to the introduction of new genes or extra copies of existing genes into a host organism. The acquired genes may be incorporated into chromosomal DNA or introduced as extra-chromosomal elements. As an example, in *E. coli*, a method for transferring DNA into a host organism is electroporation.

The term "transformation vector" refers to any vehicle used to introduce a polynucleotide in a host organism. Such vehicle can be for example a plasmid, a phage or other elements known from the expert in the art according to the organism used. The transformation vector usually contains in addition to the polynucleotide or the expression cassette other elements to facilitate the transformation of a particular host cell. An expression vector comprises an expression cassette allowing the suitable expression of the gene borne by the cassette and additional elements allowing the replication of the vector into the host organism. An expression vector can be present at a single copy in the host organism or at multiple copies.

The present invention also provides for a modified microorganism having modulated Ferredoxin-NADP+ reductase activity, wherein activity of the polypeptide of the invention is attenuated or enhanced.

The term "attenuation of the activity of an enzyme" refers to a decrease of activity of the enzyme of interest, compared to the observed activity in the same microorganism before any modification. The man skilled in the art knows numerous means to obtain this result, and for example:

Introduction of a mutation into the gene, decreasing the expression level of this gene, or the level of activity of the encoded protein.
  Replacement of the natural promoter of the gene by a low strength promoter, resulting in a lower expression.
  Use of elements destabilizing the corresponding messenger RNA or the protein.
  Deletion of the gene if no expression at all is needed.

An "increased enzymatic activity" or an "enhanced enzymatic activity" means that the activity is superior to the original activity measured in the same microorganism before any modification. The corresponding non-modified microorganism is a microorganism having the same characteristics of the modified microorganism except for the enzyme activity under consideration. Advantageously, the enzyme activity is increased by at least 50%, preferably by at least 100%, compared to the native activity of the corresponding non-modified microorganism. A method for measuring Ferredoxin-NADP+ reductase activity is given in Example 1 below.

More particularly the expression "enhanced" or "Enhanced Enzyme Activity" means that enzyme activity is higher than that which naturally occurs in a microorganism that is non-modified or non-transformed (i. e. enzyme activity that occurs naturally in a microorganism in the absence of direct or indirect manipulation of such activity/microorganism by man). This can apply to a non-modified microorganism that exhibits or not any enzyme activity prior to the modification.

The expression "Enhanced activity" in relation with a modified strain that possesses Ferredoxin NADP+ reductase activity (naturally, prior to the the modification), means an increase in enzymatic activity that is larger than the margin of error inherent in the measurement technique, preferably an increase by about 1.2-fold, 1.5 fold, particularly 2-fold or greater of the activity of the wild-type microorganism (ie activity of the enzyme of the non-modified microorganism), more preferably an increase by about 3-fold or greater, and most preferably an increase by about 5-fold or greater.

In the case the non-modified microorganism does not contain any Ferredoxin NADP+ reductase activity prior to its modification, the "Enhanced activity" corresponds to the expression of such activity at a detectable level following the modification leading to obtaining the modified microorganism of the invention, such a detectable level being sufficient for orienting the metabolism of the modified microorganism.

"Modification" or "Transformation" means a process for introducing heterologous DNA into a bacterium cell. Transformed or Modified bacterium cells are understood to encompass not only the end product of a transformation process, but also transgenic or modified progeny thereof.

"Modified" or "Transformed" or "recombinant" refer to a host organism such as a bacterium into which a heterologous nucleic acid molecule has been introduced.

The nucleic acid molecule can be stably integrated into the genome of the host or the nucleic acid molecule can also be present as an extrachromosomal molecule. Such an extrachromosomal molecule can be auto-replicating.

A "non-transformed", "non-modified" or "non-recombinant" host cell refers to a wild-type organism, e. g., a bacterium, which does not contain any heterologous nucleic acid molecule.

Percent identity: the phrase "percent identical", in the context of two nucleic acid or protein sequences, refers to two or more sequences or subsequences that have for example 60%, preferably 70%, more preferably 80%, still more preferably 90%, even more preferably 95%, and most preferably at least 99% nucleotide or amino acid residue identity, when compared and aligned for maximum correspondence, as measured using the following sequence comparison algorithms or by visual inspection.

Preferably, the percent identity exists over a region of the sequences that is at least about 50 residues in length, more preferably over a region of at least about 100 residues, and most preferably the percent identity exists over at least about 150 residues. In an especially preferred embodiment, the percent identity exists over the entire length of the coding regions.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence (s) relative to the reference sequence, based on the designated program parameters.

The microorganism according to the invention is selected among the group consisting of bacteria, yeast and fungi. Preferentially, the bacterium is selected among the group consisting of Clostridiaceae, Cyanobacteriaceae, Enterobacteriaceae, Bacillaceae, Streptomycetaceae, Pseudomonaceae and Corynebacteriaceae. More preferentially, the bacterium is selected among the group consisting of *Clostridium acetobutylicum, Thermoanaerobacterium saccharolyticum, Clostridium thermocellum, Synecchococcus elongatus, Escherichia coli, Bacillus subtilis, Lactobacillus brevis, Pseudomonas putida* and *Corynebacterium glutamicum*. Preferentially, the yeast is *Saccharomyces cerevisiae*.

It is an object of the present invention to provide a microorganism with enhanced Ferredoxin-NADP+ reductase activity, wherein expression of the native gene coding for the polypeptide of the invention is enhanced. This is preferentially obtained by introducing a strong promoter upstream the coding sequence of the native gene.

Additionnally, other regulatory elements of the gene can be modified. For example, suitable mutations that can be selected by the expert in the field in the upstream region of the gene (start codon, ribosome binding site) can results in increased expression. In addition, an inducible promoter can be introduced in order to turn on/off the expression of the gene when desired.

In a prefered embodiment of the invention, a strong promoter is present upstream to the coding sequence of the native gene coding for the polypeptide according to the invention.

It is also an object of the present invention to provide a microorganism with enhanced Ferredoxin-NADP+ reductase activity, wherein the polynucleotide of the invention is overexpressed.

Preferentially, the overexpression is obtained by transforming the organism with the vector of the invention or by integrating the polynucleotide or the cassette of the invention into the chromosome of the organism.

One single copy or multiple copies of the gene borne by expression vectors or integrated into the chromosome can be introduced in order to modulate the overexpression. In addition, different kind of promoters inducing different level of expression of the gene can be used.

The adequate position on the chromosome for the insertion of the new gene can be selected by the expert in the art. This position (or locus) should not affect the essential functions of the host organism. Methods for integration of a gene into the chromosome of a host organism are disclosed for example in Sambrook et al (1989).

The present invention is also related to a microorganism with enhanced Ferredoxin-NADP+ reductase activity, which is further modified to produce ethanol, n-butanol, 1, 3 propanediol and 1, 2 propanediol by new metabolic pathways.

In a specific embodiment of the invention, modifications are introduced into the microorganism with enhanced Ferredoxin-NADP+ reductase activity specifically for the production of ethanol by a new metabolic pathway (FIG. 1).

Preferentially, the pyruvate ferredoxin oxidoreductase and the soluble transhydrogenase activities are increased. The preferred method is the overexpression of the pfor (CA_C2229), fdx (CA_C0303) genes coding for pyruvate ferredoxin oxidoreductase and ferredoxin respectively, and udhA gene coding for soluble transhydrogenase. Additionnally, the activity Fe—S cluster assembly proteins, IscS, IscU, and IscA are increase to improve [4Fe-4S] assembly in Pfor and Fdx to increase the pyruvate ferredoxin oxidoreductase and the soluble transhydrogenase activities. This can be achieved by the attenuation of the iscR gene coding for a factor IscR, responsible for the repression of the isc operon. Furthermore, one or several mutations can be introduced in the pfor, fdx or udhA genes to increase the pyruvate ferredoxin oxidoreductase and the soluble transhydrogenase activities under the culture conditions used.

The other gene whose expression may advantageously be enhanced is adhE coding for a bifunctionnal acetaldehyde and ethanol dehydrogenase.

In another embodiment of the invention, the methylglyoxal synthase enzyme activity, the first enzyme of the methylglyoxal bypass, encoded by the gene mgsA is attenuated.

Preferentially, in the microorganism according to the invention, some enzyme activities involved in by-product formation pathways are attenuated to increase the yield of ethanol:

The pyruvate formate lyase activity, responsible for the synthesis of acetyl-CoA and formate from pyruvate, encoded by the genes pflA and pflB.

The pyruvate dehydrogenase activity, responsible for the synthesis of acetyl-CoA and NADH from pyruvate, encoded by the genes aceE, aceF and lpd. The fumarate reductase activity, responsible for the synthesis of succinate from fumarate, encoded by the operonfrdABCD.

The lactate dehydrogenase activity, responsible for the synthesis of lactate from pyruvate, encoded by the gene ldhA.

The phosphotransacetylase and acetate kinase activities, responsible for the synthesis of acetate in two steps from acetyl-CoA, encoded respectively by the genes pta and ackA.

The pyruvate oxidase activity, responsible for the synthesis of acetate in one step from pyruvate, encoded by the gene poxB.

Preferentially, the attenuation of activity is obtained by the attenuation of at least one of these genes.

Preferentially the microorganism designed to produce ethanol by this new metabolic pathway is selected among bacteria, yeasts or fungi. More preferentially, the microorganism is selected among Enterobacteriaceae, Cyanobacteriaceae, Bacillaceae, Clostridiaceae, Streptomycetaceae, Pseudomonaceae and Corynebacteriaceae. Even more preferentially, the microorganism is either from the species *Escherichia coli*, *Synecchococcus elongatus*, *Bacillus subtilis*, *Lactobacillus brevis*, *Pseudomonas putida*, *Clostridium acetobutylicum*, *Thermoanaerobacterium saccharolyticum*, *Clostridium thermocellum*, or *Corynebacterium glutamicum*. Preferentially, the yeast is *Saccharomyces cerevisiae*.

In another specific embodiment of the invention, modifications are introduced into the microorganism with enhanced Ferredoxin-NADP+ reductase activity specifically for the production of n-butanol by a new metabolic patway (FIG. 2).

Preferentially, the pyruvate ferredoxin oxidoreductase, the thiolase, the β-hydroxybutyryl-CoA dehydrogenase, the crotonase, the butyryl-coA dehydrogenase, the butyraldehyde dehydrogenase, the butanol dehydrogenase and the soluble transhydrogenase activities are increased. The preferred method is the overexpression of the pfor (CA_C2229), fdx (CA_C0303) genes coding for pyruvate ferredoxin oxidoreductase and ferredoxin respectively, atoB gene coding for thiolase, hbd (CA_C2708) gene coding for β-hydroxybutyryl-CoA dehydrogenase, crt (CA_C2712) gene coding for crotonase, bcd (CA_C2711), etfA (CA_C2709) and etfB (CA_C2710) genes coding for butyrylCoA dehydrogenase complex, adhE2 (cap035) gene coding for bifunctionnal butyraldehyde and butanol dehydrogenase and udhA gene coding for soluble transhydrogenase. Additionnally, the activity Fe—S cluster assembly proteins, IscS, IscU, and IscA are increase to improve [4Fe-4S] assembly in Pfor and Fdx to increase the pyruvate ferredoxin oxidoreductase and the soluble transhydrogenase activities. This can be achieved by the attenuation of the iscR gene coding for a factor IscR, responsible for the repression of the isc operon. Furthermore, one or several mutations can be introduced in the pfor, fdx, atoB, hbd, crt, bcd, etfA, etfB, adhE2 or udhA genes to increase the pyruvate ferredoxin oxidoreductase, the thiolase, the β-hydroxybutyryl-CoA dehydrogenase, the crotonase, the butyryl-coA dehydrogenase, the butyraldehyde dehydrogenase, the butanol dehydrogense or the soluble transhydrogenase activities under the culture conditions used.

In another embodiment of the invention, the methylglyoxal synthase enzyme activity, the first enzyme of the methylglyoxal bypass, encoded by the gene mgsA is attenuated.

Preferentially, in the microorganism according to the invention, some enzyme activities involved in by-product formation pathways are attenuated in order to increase the yield of n-butanol:

The pyruvate formate lyase activity, responsible for the synthesis of acetyl-CoA and formate from pyruvate, encoded by the genes pflA and pflB.

The pyruvate dehydrogenase activity, responsible for the synthesis of acetyl-CoA and NADH from pyruvate, encoded by the genes aceE, aceF and lpd. The fumarate reductase activity, responsible for the synthesis of succinate from fumarate, encoded by the operonfrdABCD.

The lactate dehydrogenase activity, responsible for the synthesis of lactate from pyruvate, encoded by the gene ldhA.

The phosphotransacetylase and acetate kinase activities, responsible for the synthesis of acetate in two steps from acetyl-CoA, encoded respectively by the genes pta and ackA.

The pyruvate oxidase activity, responsible for the synthesis of acetate in one step from pyruvate, encoded by the gene poxB.

The alcool-aldehyde dehydrogenase activity, responsible for the synthesis of ethanol from acetyl-CoA, encoded by the gene adhE.

Preferentially, the attenuation of activity is obtained by the attenuation of at least one of these genes.

Preferentially the microorganism designed to produce n-butanol by this new metabolic pathway is selected among bacteria, yeasts or fungi. More preferentially, the microorganism is selected among Enterobacteriaceae, Cyanobacteriaceae, Bacillaceae, Clostridiaceae, Streptomycetaceae, Pseudomonaceae and Corynebacteriaceae. Even more preferentially, the microorganism is either from the species *Escherichia coli, Synecchococcus elongatus. Lactobacillus brevis, Pseudomonas putida, Bacillus subtilis, Clostridium acetobutylicum, Thermoanaerobacterium saccharolyticum, Clostridium thermocellum* or *Corynebacterium glutamicum*. Preferentially, the yeast is *Saccharomyces cerevisiae*.

In another specific embodiment of the invention, modifications are introduced into the microorganism with enhanced Ferredoxin-NADP+ reductase activity specifically for the production of 1, 3 propanediol from glycerol by a new metabolic patway (FIG. 3).

Preferentially, the pyruvate ferredoxin oxidoreductase, the B12-independent glycerol dehydratase, the NADP+ dependent 1, 3 propanediol dehydrogenase and the membrane bound transhydrogenase activities are increased. The preferred method is the overexpression of the pfor (CA_C2229) and fdx (CA_C0303) genes coding for pyruvate ferredoxin oxidoreductase and ferredoxin, dhaB1, dhaB2 genes coding for glycerol dehydratase and glycerol dehydratase activating enzyme (Sarcabal et al, 1999), yqhD gene coding for 1, 3 propanediol dehydrogenase and pntAB genes coding for membrane bound transhydrogenase. Additionnally, the activity of Fe—S cluster assembly proteins, IscS, IscU, and IscA are increase to improve [4Fe-4S] assembly in Pfor and Fdx to increase the pyruvate ferredoxin oxidoreductase activity. This can be achieved by the attenuation of the iscR gene coding for a factor IscR, responsible for the repression of the isc operon. Furthermore, one or several mutations can be introduced in the pfor, fdx, dhaB1, dhaB2, yqhD and pntAB genes to increase the pyruvate ferredoxin oxidoreductase, the glycerol dehydratase, the NADP+ dependent 1, 3 propanediol dehydrogenase and the membrane bound transhydrogenase activities activities under the culture conditions used.

Other genes whose expression may advantageously be enhanced are the following: ack and pta coding respectively for acetate kinase and phosphotransacetylase.

In another embodiment of the invention, the soluble transhydrogenase enzyme involved in NADPH oxidation to produce NADH encoded by the gene udhA is attenuated.

Preferentially, in the microorganism according to the invention, some enzyme activities involved in by-product formation pathways are attenuated in to increase the yield of 1, 3-propanediol:

The pyruvate formate lyase activity, responsible for the synthesis of acetyl-CoA and formate from pyruvate, encoded by the genes pflA and pflB.

The pyruvate dehydrogenase activity, responsible for the synthesis of acetyl-CoA and NADH from pyruvate, encoded by the genes aceE, aceF and lpd. The fumarate reductase activity, responsible for the synthesis of succinate from fumarate, encoded by the operonfrdABCD.

The lactate dehydrogenase activity, responsible for the synthesis of lactate from pyruvate, encoded by the gene ldhA.

The pyruvate oxidase activity, responsible for the synthesis of acetate in one step from pyruvate, encoded by the gene poxB.

The alcool-aldehyde dehydrogenase activity, responsible for the synthesis of ethanol from acetyl-CoA, encoded by the gene adhE.

The aldehyde dehydrogenase activities, responsible of the synthesis of hydroxypropionate from hydroxypropionaldehyde encoded by the aldA and aldB genes The anaerobic glycerol-3-phosphate dehydrogenase, responsible of the synthesis of dihydroxyacetone phosphate from glycerol-3-phosphate encoded by the gene glpA The aerobic glycerol-3-phosphate dehydrogenase, responsible of the synthesis of dihydroxyacetone phosphate from glycerol-3-phosphate encoded by the gene glpD Preferentially, the attenuation of activity is obtained by the attenuation of at least one of these genes.

Preferentially the microorganism designed to heterologously produce 1, 3 propanediol from glycerol by this new metabolic pathway is selected among bacteria, yeasts or fungi. More preferentially, the microorganism is selected among Enterobacteriaceae, Cyanobacteriaceae, Bacillaceae, Clostridiaceae, Streptomycetaceae, Pseudomonaceae and Corynebacteriaceae. Even more preferentially, the microorganism is either from the species *Escherichia coli, Synecchococcus elongates, Lactobacillus brevis, Bacillus subtilis, Pseudomonas putida, Clostridium acetobutylicum, Thermoanaerobacterium saccharolyticum, Clostridium thermocellum* or *Corynebacterium glutamicum*. Preferentially, the yeast is *Saccharomyces cerevisiae*.

In one embodiment of the invention, the microorganism with enhanced Ferredoxin-NADP+ reductase activity activity is further modified to produce 1,2-propanediol from a source of carbon by a new metabolic pathway.

Preferentially, the pyruvate ferredoxin oxidoreductase, methylglyoxal synthase, methylglyoxal reductase, 1,2-propanediol dehydrogenase and membrane bound transhydrogenase. To obtain the increase of the specific enzymatic activities, the genes coding for these activities are preferentially overexpressed: the pfor (CA_C2229), and fdx (CA_C0303) coding for pyruvate ferredoxin oxidoreductase and ferredoxin, mgsA gene, coding for methylglyoxal synthase, yqhD, yafB, ydhF, ycdW, yqhE, yeaE, yghZ, yajO, tas, ydjG, and ydbC, all coding for methylglyoxal reductases, gldA, fucO or sadh from *C. heijerinckii* coding for 1,2-propanediol dehydrogenase and pntAB coding for membrane bound transhydrogenase.

The combination of the overexpression of the pfor, fdx, mgsA, yqhD and gldA genes or pfor, fdx, mgsA, yqhD and sadh and pntAB are preferentially used.

Additionnally, the activity of Fe—S cluster assembly proteins, IscS, IscU, and IscA. are increase to improve [4Fe-4S] assembly in Pfor and Fdx to increase the pyruvate ferredoxin oxidoreductase and the soluble transhydrogenase activities. This can be achieved by the attenuation of the iscR gene coding for a factor IscR, responsible for the repression of the isc operon. Furthermore, one or several mutation can be introduced in the pfor, fdx, mgsA, yqhD and gldA to increase the pyruvate ferredoxin oxidoreductase, methylglyoxal synthase, methylglyoxal reductase and 1,2-propanediol dehydrogenase activities under the culture conditions used.

Attenuation of the enzymatic activities involved in the Entner-Doudoroff pathway, encoded by the genes edd and eda. The Entner-Doudoroff pathway provides an alternative way to degrade glucose to glyceraldehyde-3-phosphate and pyruvate besides glycolysis. The attenuation of the Entner-Doudoroff pathway assures that most or at best all glucose is degraded via glycolysis and is utilized for the production of 1,2-propanediol.

Attenuation of enzymes involved in the conversion of methylglyoxal into lactate: glyoxalase I and II, encoded respectively by the gloA and gloB genes, catalysing the synthesis of lactoyl glutathione from methylglyoxal and lactaldehyde dehydrogenases encoded by the aldA and aldB genes, catalysing the synthesis of (S) lactate from (S)

lactaldehyde and glyoxalase III encoded by yedU gene (also known as hchA) catalysing the reduction of methylglyoxal to (S) lactate.

Attenuation of these enzymes is intended to spare the precursor methylglyoxal for the synthesis of the desired products.

Attenuation of enzymes involved in the synthesis of by-products such as lactate, ethanol and formate: lactate dehydrogenase, encoded by the gene ldhA, catalysing the synthesis of lactate from pyruvate, alcohol-aldehyde dehydrogenase, encoded by the gene adhE, catalysing the synthesis of ethanol from acetyl-CoA and pyruvate formate lyase, encoded by the genes pflA and pflB, catalysing the synthesis of acetyl-CoA and formate from pyruvate.

Preferentially, at least one of these genes is attenuated.

In another specific embodiment of the invention, the triose phosphate isomerase activity is attenuated. Preferentially, this result is achieved by attenuating the expression of the tpiA gene. More preferably, the tpiA gene is deleted. The tpiA gene encodes the enzyme 'triose phosphate isomerase', which catalyses the conversion of DHAP into glyceraldehyde 3-phosphate. The attenuation of the expression of this gene ensures that half of the glucose metabolized is converted to 1,2-propanediol.

In another specific embodiment of the invention, the glyceraldehyde 3 phosphate dehydrogenase activity is attenuated. The glyceraldehyde 3-phosphate dehydrogenase, also called GAPDH, is one of the key enzymes involved in the glycolytic conversion of glucose to pyruvic acid. The attenuation of the enzyme resulted in the redirection of part of the GA3P toward the synthesis of 1,2-propanediol. The yield of 1,2-propanediol over glucose can then be greater than 1 mole/mole.

In another embodiment of the invention, in the microorganism according to the invention, the efficiency of the sugar import is increased. A strong attenuation of the expression of the gapA gene resulting in a decrease of the carbon flux in the GAPDH reaction by more than 50% result in the synthesis of less than 1 mole of PEP per mole of glucose imported. PEP is required by the sugar-phosphotransferase system (PTS) normally used for the import of simple sugars into the cell, since import is coupled to a phospho-transfer from PEP to glucose yieding glucose-6-phosphate. Thus reducing the amount of PEP will negatively impact on sugar import.

In a specific embodiment of the invention, the sugar might be imported into the microorganism by a sugar import system independent of phosphoenolpyruvate. The galactase-proton symporter encoded by the gene galP that does not involve phosphorylation can be utilized. In this case, the imported glucose has to be phosphorylated by the glucose kinase activity encoded by the glk gene. To promote this pathway, the expression of at least one gene selected among galP and glk is increased.

In another specific embodiment of the invention, the efficiency of the sugar-phosphotransferase system (PTS) is increased by increasing the availability of the metabolite phosphoenopyruvate by increasing the activity of the phosphoenolpyruvate synthase enzyme. This enzyme is encoded by the ppsA gene. Therefore, preferentially in the microorganism, the expression of the ppsA gene is preferentially increased.

In another specific embodiment of the invention, the synthesis of the by-product acetate is prevented by attenuating at least one enzyme involved in its synthesis. It is preferable to avoid such acetate synthesis to optimize the production of 1,2-propanediol.

To prevent the production of acetate, advantageously at least one gene selected among ackA, pta is attenuated. These genes all encode enzymes involved in the different acetate biosynthesis pathways.

To obtain an overexpression of a gene of interest, the man skilled in the art knows different methods, and for example:

1—Replacement of the native promoter of the gene with a promoter inducing a stronger level of expression of the gene of interest.

2—Introduction into the microorganism of an expression vector carrying and expressing said gene of interest.

3—Introduction of additional copies of the gene of interest into the chromosome of the microorganism.

Another way to obtain an increased enzymatic activity is to introduce into the gene of interest a specific mutation allowing the translation of a gene product presenting a higher activity than the native protein.

Under anaerobic or microaerobic conditions, availability of NADH for the reduction of the precursors into 1,2-propanediol is advantageously increased. This is obtained by alleviating the repression on the tricarboxylic acid cycle mediated by the global regulator ArcA (encoded by the arcA gene).

Preferentially the microorganism designed to produce mainly 1,2-propanediol is selected among bacteria, yeasts or fungi. More preferentially, the microorganism is selected among Enterobacteriaceae, Cyanobacteriaceae, Bacillaceae, Clostridiaceae, Pseudomonaceae Streptomycetaceae and Corynebacteriaceae. Even more preferentially, the microorganism is either from the species *Escherichia coli, Synechococcus elongatus. Lactobacillus brevis, Bacillus subtilis, Pseudomonas putida, Clostridium acetobutylicum, Thermoanaerobacterium saccharolyticum, Clostridium thermocellum* or *Corynebacterium glutamicum*. Preferentially, the yeast is *Saccharomyces cerevisiae*.

The term "attenuation of the expression of a gene" according to the invention denotes the partial or complete suppression of the expression of a gene, which is then said to be "attenuated". This suppression of expression can be either an inhibition of the expression of the gene, a deletion of all or part of the promoter region necessary for the gene expression, or a deletion in the coding region of the gene. Preferentially, the attenuation of a gene is essentially the complete deletion of that gene, which gene can be replaced by a selection marker gene that facilitates the identification, isolation and purification of the strains according to the invention. A gene is inactivated preferentially by the technique of homologous recombination (Datsenko, K. A. & Wanner, B. L., 2000).

The present invention provides for a method for modulating the Ferredoxin-NADP+ reductase activity enzymatic activity in a microorganism, wherein activity of the polypeptide of the invention is enhanced or attenuated in said microorganism.

Preferentially, in said method, the Ferredoxin-NADP+ reductase activity enzymatic activity is enhanced by overexpressing the polynucleotide of the invention.

Preferentially, in said method, the Ferredoxin-NADP+ reductase activity enzymatic activity is attenuated by attenuating the expression of the polynucleotide of the invention.

The invention is also related to a method for preparing ethanol, wherein a microorganism according to the invention is grown in an appropriate culture medium comprising a source of carbon, and the produced ethanol is recovered. The production of ethanol is performed under microaerobic or anaerobic conditions, preferentially under anaerobic conditions.

The term "carbon substrate" or "source of carbon" means any carbon source capable of being metabolized by a microorganism wherein the substrate contains at least one carbon atom. Authors refer particularly to renewable, inexpensive and fermentable carbon source such as monosaccharides, oligosaccharides, polysaccharides, single-carbon substrates, and polyols such as glycerol. Saccharides of the formula $(CH_2O)_n$ are also called oses or "simple sugars"; monosaccharides include fructose, glucose, galactose and mannose. Other carbon sources are disaccharides, trisaccharides, oligosaccharides and polysaccharides. Disaccharides include saccharose (sucrose), lactose and maltose. Starch and hemicellulose are polysaccharides, also known as "complex sugars".

Advantageously the recovered ethanol is furthermore purified.

The invention is also related to a method for preparing n-butanol, wherein a microorganism according to the invention is grown in an appropriate growth medium containing a carbon source, and the n-butanol is recovered. The production of n-butanol is performed under microaerobic or anaerobic conditions, preferentially under anaerobic conditions.

Advantageously, the recovered n-butanol is furthermore purified.

The invention is also related to a method for preparing 1,3-propanediol, wherein a microorganism according to the invention is grown in an appropriate growth medium containing glycerol as a carbon source, and the 1,3-propanediol is recovered. The production of 1,3-propanediol is performed under microaerobic or anaerobic conditions, preferentially under anaerobic conditions.

Advantageously, the recovered 1,3-propanediol is furthermore purified.

The invention is also related to a method for preparing 1,2-propanediol, wherein a microorganism according to the invention is grown in an appropriate growth medium containing a carbon source, and the 1,2-propanediol is recovered. The production of 1,2-propanediol is performed under microaerobic or anaerobic conditions, preferentially under anaerobic conditions.

Advantageously, the recovered 1,2-propanediol is furthermore purified.

The culture conditions for fermentation processes can be readily defined by those skilled in the art. In particular, bacteria are fermented at temperatures between 20° C. and 55° C., preferably between 25° C. and 40° C., and preferably at about 35° C. for *C. acetobutylicum* and at about 37° C. for *E. coli* and *K. pneumoniae*.

This process can be carried out either in a batch process, in a fed-batch process or in a continuous process.

Micro-aerobic conditions are defined as culture conditions wherein low percentages of oxygen (e.g. using a mixture of gas containing between 0.1 and 10% of oxygen, completed to 100% with nitrogen), is dissolved into the liquid phase.

Anaerobic conditions are defined as culture conditions wherein no oxygen is provided to the culture medium. Strictly anaerobic conditions are obtained by sparging an inert gas like nitrogen into the culture medium to remove traces of other gas. Nitrate can be used as an electron acceptor to improve ATP production by the strain and improve its metabolism.

The term "appropriate growth medium" according to the invention denotes a medium of known molecular composition adapted to the growth of the micro-organism. For example, a mineral culture medium of known set composition adapted to the bacteria used, containing at least one carbon source. In particular, the mineral growth medium for *E. coli* or *K. pneumoniae* can thus be of identical or similar composition to M9 medium (Anderson, 1946, *Proc. Natl. Acad. Sci. USA* 32:120-128), M63 medium (Miller, 1992; A Short Course in Bacterial Genetics: A Laboratory Manual and Handbook for *Escherichia coli* and Related Bacteria, Cold Spring Harbor Laboratory Press, Cold Spring Harbor, New York) or a medium such as that defined by Schaefer et al. (1999, *Anal. Biochem.* 270: 88-96).

The carbon source used for the culture of *E. coli* or *C. acetobutylicum* is preferentially a simple carbon source and can be arabinose, fructose, galactose, glucose, lactose, maltose sucrose, xylose or glycerol. An especially preferred simple carbon source is glucose.

The invention is described above, below and in the Examples with respect to *C. acetobutylicum* and *E. coli*. Thus the genes that can be attenuated, deleted or overexpressed for the initial and evolved strains according to the invention are defined using the denomination of the genes from *E. coli* or *C. acetobutylicum*. However, this designation has a more general meaning according to the invention, and covers the corresponding genes in other micro-organisms. Using the GenBank references of the genes from *E. coli* or *C. acetobutylicum*, those skilled in the art can determine equivalent genes in other organisms than *E. coli* or *C. acetobutylicum*.

The means of identification of the homologous sequences and their percentage homologies are well-known to those skilled in the art, and include in particular the BLAST programmes that can be used on the website http://www.ncbi.nlm.nih.gov/BLAST/ with the default parameters indicated on that website. The sequences obtained can be exploited (aligned) using for example the programmes CLUSTALW (http://www.ebi.ac.uk/clustalw/), with the default parameters indicated on these websites.

The PFAM database (protein families database of alignments and hidden Markov models http://www.sanger.ac.uk/Software/Pfam/) is a large collection of alignments of protein sequences. Each PFAM makes it possible to visualise multiple alignments, view protein domains, evaluate distributions among organisms, gain access to other databases and visualise known protein structures.

COGs (clusters of orthologous groups of proteins http://www.ncbi.nlm.nih.gov/COG/) are obtained by comparing protein sequences derived from 66 fully sequenced unicellular genomes representing 14 major phylogenetic lines. Each COG is defined from at least three lines, making it possible to identify ancient conserved domains.

EXAMPLES

Example 1

Figure 1:
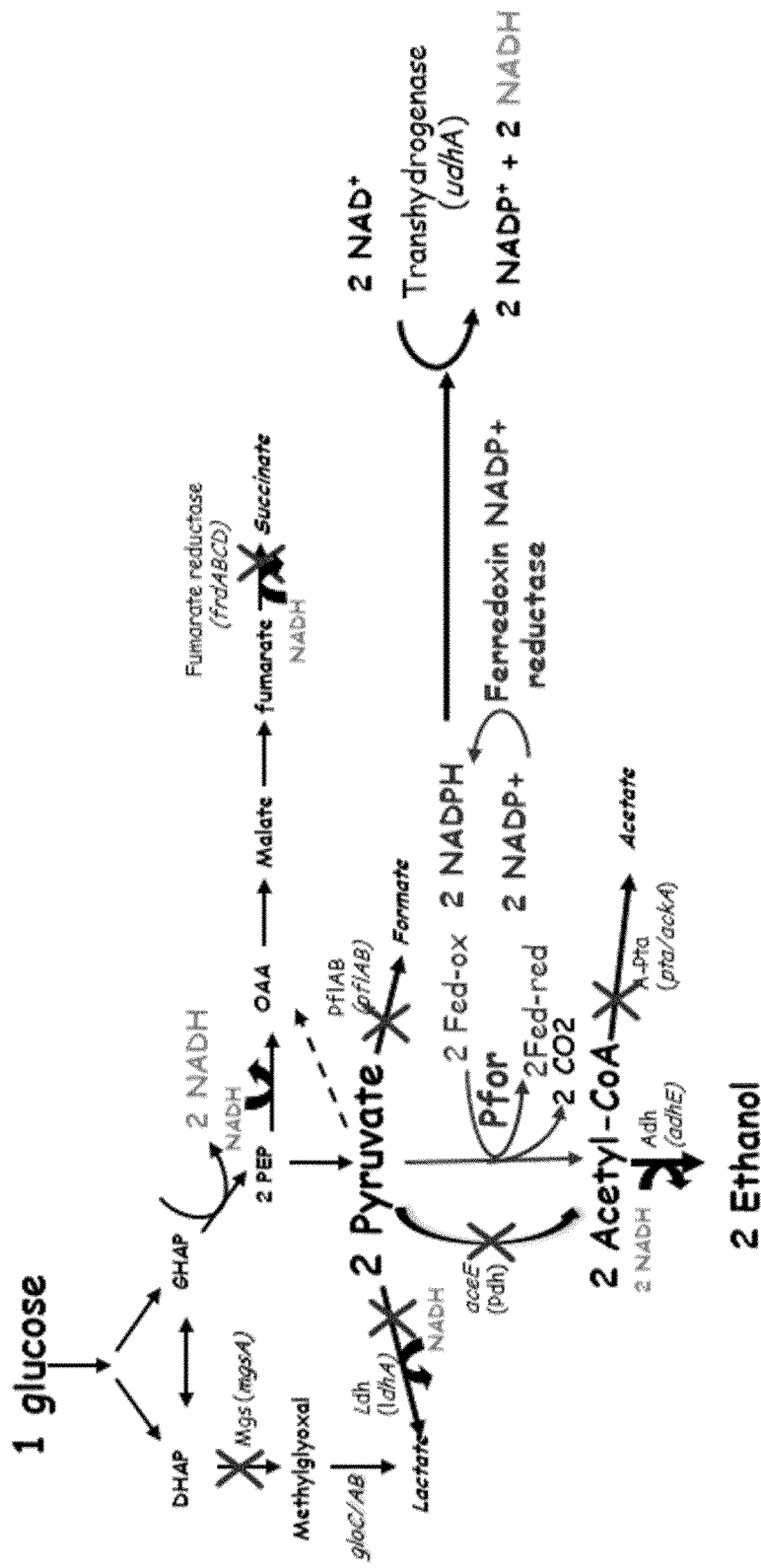
FIG. 1: New metabolic pathway for ethanol production
Figure 2:
FIG. 2: New metabolic pathway for butanol production
Figure 3:
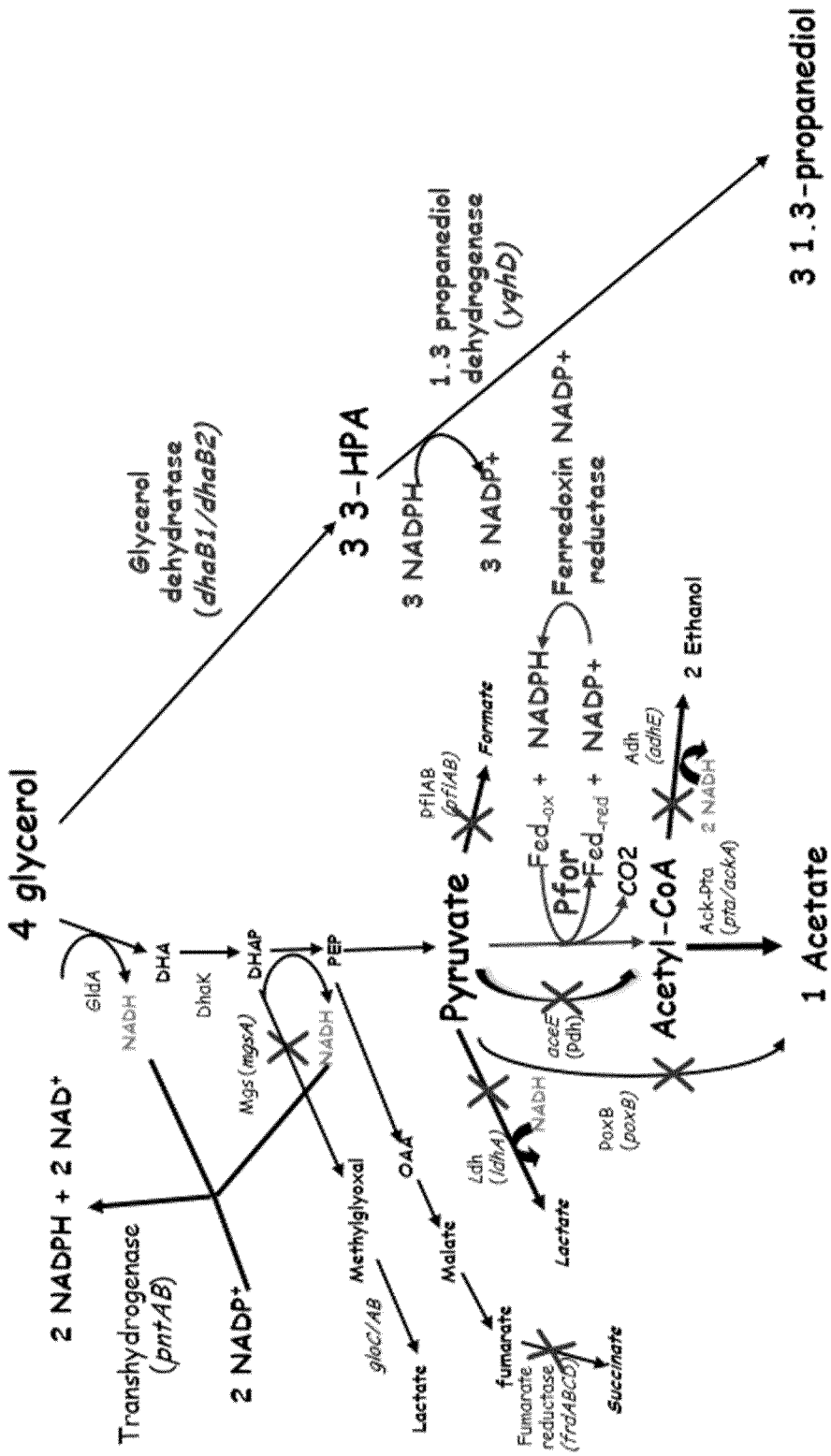
FIG. 3: New metabolic pathway for 1.3 propanediol production
Figure 4:
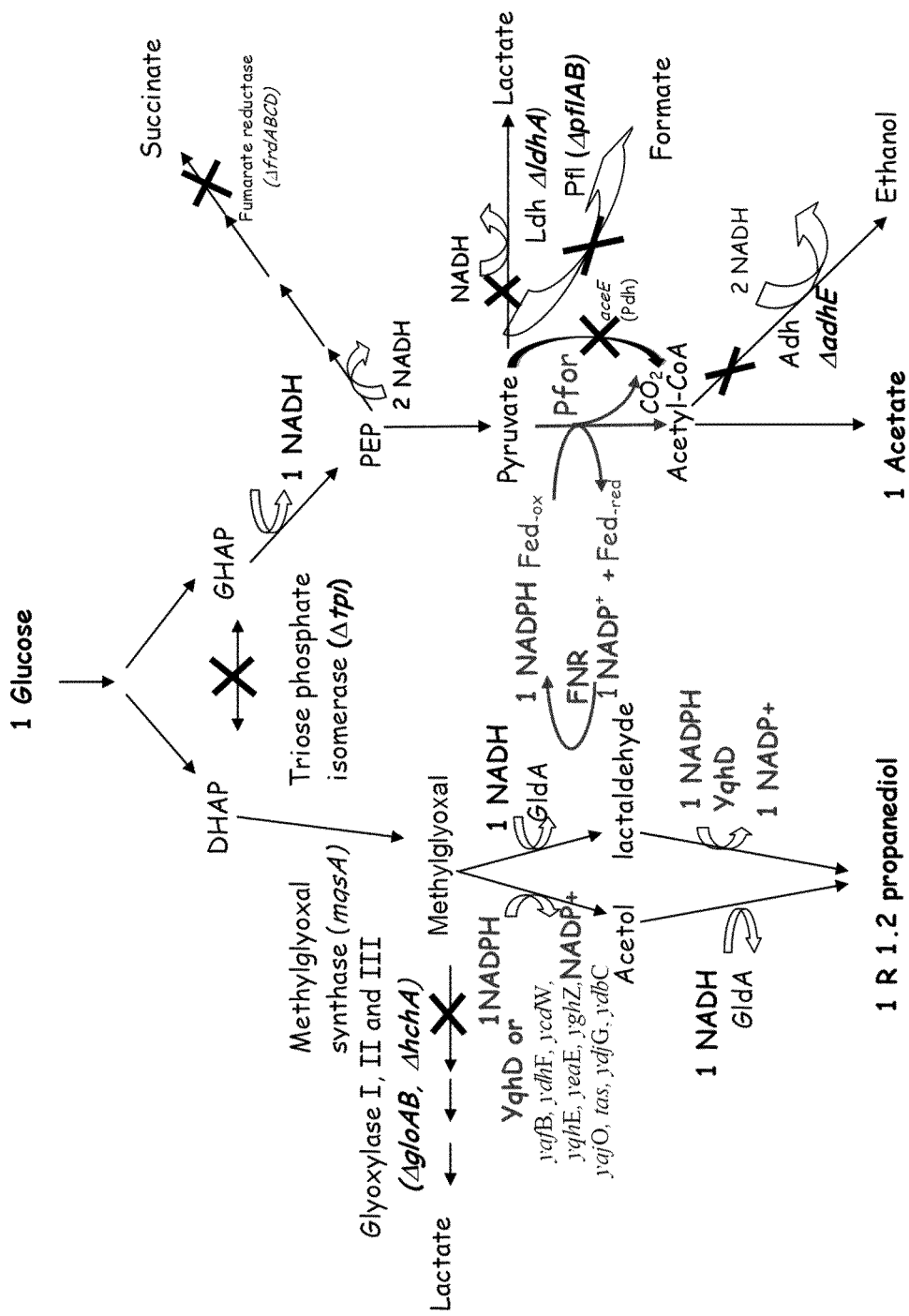
FIG. 4: New metabolic pathway for 1.2 propanediol production
Figure 5:
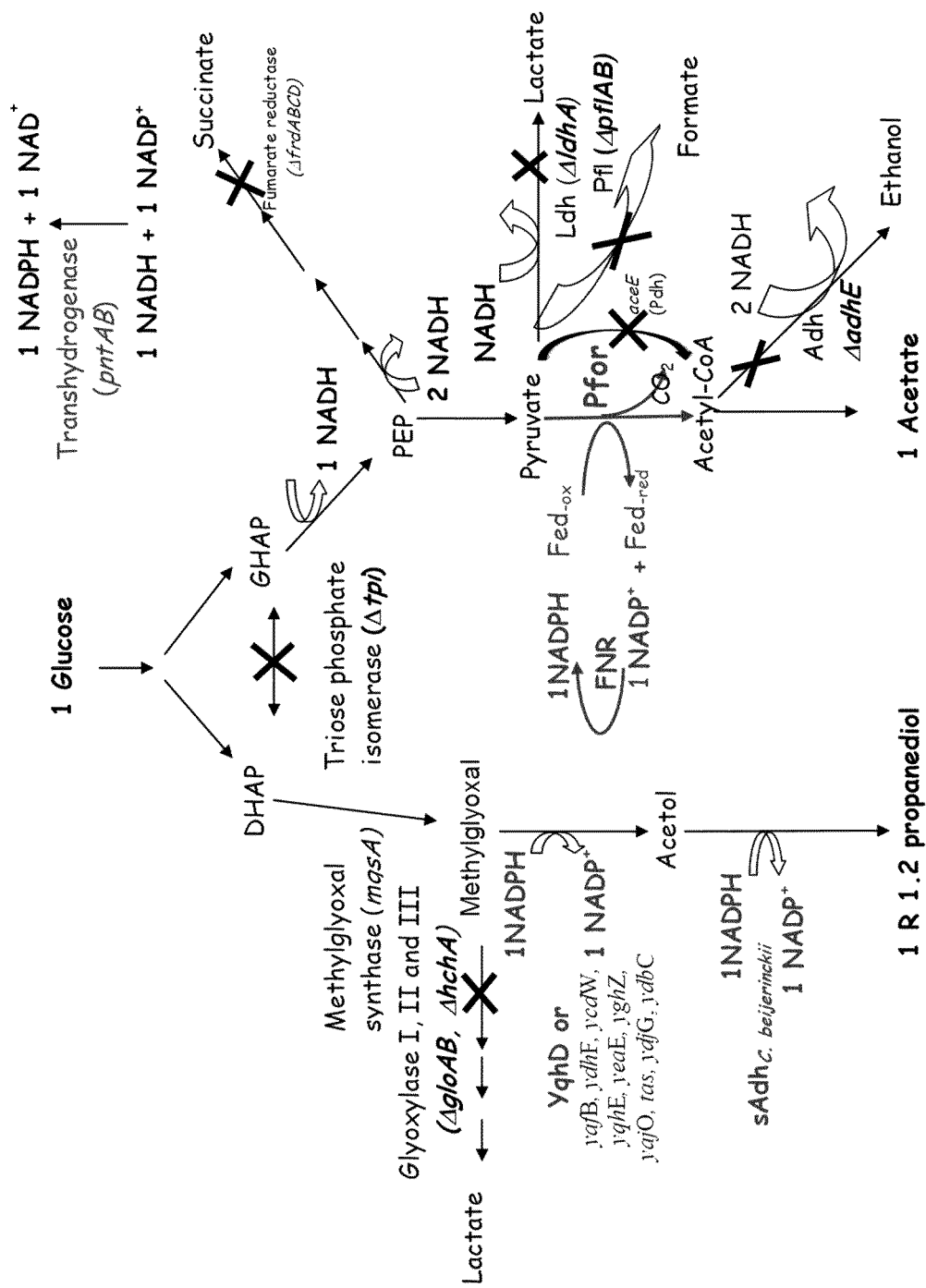
FIG. 5: Another New metabolic pathway for 1.2 propanediol production

Purification of Ferredoxin NADP+ Activity in *C. acetobutylicum* and Identification of the Encoding Gene 1.1—Ferredoxin NADP+ Reductase Activity and NADPH Ferredoxin Reductase Activity Assays:

All enzyme assays were performed in the anaerobic workstation under a nitrogen atmosphere. All reagent solutions were prepared in the assay buffer (previously boiled and degassed with nitrogen) and kept under a nitrogen atmosphere. Specific activities were determined in a range where linearity with protein concentration was established. Each enzyme assay was done at least in duplicate. One unit of enzyme activity is defined as the amount of enzyme that catalyzes the conversion of 1 μmol of substrate per min. The concentrations of components in the reaction mixtures (1 ml total volume) are given below.

In vitro ferredoxin NADP+ reductase activity was assayed by measuring the reduction of NADP+ using electrons from reduced methyl viologen or reduced ferredoxin (CA_C0303) with H2 as the reductant of the methyl viologen or ferredoxin (CA_C 0303) (Demuez et al. 2007) in the presence of the Fe—Fe Hydrogenase from *Clostridium acetobutylicum* (CA_C0028) (Vasconcelos et al. 1994, Girbal et al. 2005). The reaction was performed anaerobically at 37° C., in 100 mM Tris-HCl buffer (pH 7) with 2 mM DTT, 25 μM FAD, 150 μM methyl viologen, 1.6 mM NADP+, 6 U (or more) of purified hydrogenase HydA from *C. acetobutylicum* and crude extract (or purified protein) and followed by monitoring the increase in A 340 nm as an indication of the apparition of NADPH using a spectrophotometer (Hewlett Packard 8453). After a gentle stream with hydrogen in the quartz cuvette cells, assays were initiated by the addition of methyl-viologen and then, after the reduction of methyl viologen followed at a wavelength of 560 nm, by the addition of NADP+. In all reactions, non-enzymatic rates were subtracted from the observed initial reaction rates.

In vitro NADPH ferredoxin reductase activity was assayed by monitoring the increase of A560 nm as an indication of the reduction of methyl viologen using a spectrophotometer (Hewlett Packard 8453). The reaction was carried out anaerobically at 37° C. in quartz cuvette cells in 100 mM Tris-HCl buffer (pH 7.6) with 2 mM DTT, 10 μM FAD, 250 μM NADPH, ethanol 3% vol/vol, 45 U Adh (*S. cerevisiae*), 10 mM methyl viologen, 250 μM NADPH, and crude extract or purified protein. Assays were initiated by the addition of methyl viologen. In all reactions, non-enzymatic rates were subtracted from the observed initial reaction rates.

The extinction coefficient of methyl viologen at 560 nm and NADPH at 340 were 7.71 mM-1 cm-1 and 6.29 mM-1 cm-1 respectively. The total protein concentration of the cell-free extract or purified fraction was determined using the Bradford method (Biorad reagent) (Bradford 1976) with bovine serum albumin as the standard.

1.2—Purification of Ferredoxin NADP reductase in *C. acetobutylicum* Under Solventogenic Conditions:

*C. acetobutylicum* ATCC 824 strain was kept in spore form at −20° C. in the synthetic medium (MS), as previously described (Meynial-Salles et al. 2005). The flask cultures of *C. acetobutylicum* strains were grown anaerobically in synthetic medium (MS) and were inoculated with spore stock at 10% (v/v) and heat-shocked at 80° C. for 15 min. Cells were grown up at 37° C. to an OD620 nm of approximately 2.0 and the pH was maintained by buffering the culture medium with calcium carbonate, prior to inoculation of the bioreactor at 10% (v/v).

The pH-controlled batch fermentations were performed in synthetic medium. A 2 L Biostat B bioreactor (Sartorius, Aubagne, France) was used with a working volume of 1.3 L. After sterilization, the medium was sparged with O2-free nitrogen for 30 min During the course of the experiment, the medium was maintained under a slight nitrogen overpressure to avoid O2 entry into the reactor. All tubing was made of butyl rubber, and the reactor gas outlet was protected with a pyrogallol arrangement.

Cultures were stirred at 300 rpm, the temperature was set at 35° C., and the pH was maintained at 4.8 with automatic addition of NH4OH (3N). The cell concentration was measured turbidimetrically by monitoring the optical density (OD) at 620 nm (Biochrom libra S11) and products formation were measured in duplicate using High Performance Liquid Chromatography (HPLC) analysis (Agilent 1200 series, Massy, France) (Dusséaux et al. 2013).

When the OD620 nm reached an approximatively value of 16, after the switch from acidogenic to solventogenic phase, cells were harvested under Hydrogen pressure and transferred into anaerobic chamber. Cells were washed and concentrated 20 times in 100 mM Tris-HCl 2 mM DTT 10% glycerol (pH 7.6) buffer and frozen at −80° C.

The entire purification procedure was performed under anaerobic conditions. All purification buffers were preliminary degassed and 10 μM FAD and 2 mM DTT were added to prevent non-reversible activity losses.

Later, the frozen cells from solventogenic batch cultures of *C. acetobutylicum* ATCC 824 were thawed and broken by sonication using an ultrasonic disintegrator (vibracell 72434, Bioblock) at 4° C. in four cycles of 30 sec with 2-min intervals. Debris were removed by centrifugation at 8600 g for 10 min, 4° C. (Sigma centrifuge 2-16K). Nucleic acids were precipitated by addition of streptomycin sulfate (200 mg/ml) in the supernatant and removed by centrifugation as before. The recovered extract was then diluted 5 times in 100 mM Tris-HCL buffer (pH 8) before loaded on a 5 mL HiTrap Capto-DEAE matrix (GE Healthcare, ref 28-9165-40) connected to an AKTA purifier (GE Healthcare, Sweden). Active fractions were screened with the NADPH Ferredoxin Reductase assay using methyl viologen as previously described. The column was equilibrate in 100 mM Tris-HCL buffer (pH 8) and elution was performed with a 3 steps gradient of 100 mM Tris-HCL+1M NaCl buffer (pH 8): 1CV 0-4%, 20CV 4-16% (target elution) and 5CV 16-100%; 2 mL fractions were collected. The most active fraction from Capto-DEAE column was concentrated on Vivaspin 15/10000MW (Sartorius Stedim, ref VS1502) to reduce the sample volume at 150 μL by centrifugation at 3000 g, 15 min. For the last purification step, the 150 □1 sample volume was applied on a Superose 12, 10/300 GL column (GE Healthcare, ref 17-5173-01) preliminary equilibrated in 100 mM Tris-HCl+150 mM NaCl buffer (pH7.6) and fractions of 400 μL were collected. Finally, the total protein concentration of the cell-free extract or purified fraction was determined using the Bradford method (Biorad reagent) (Bradford 1976) with bovine serum albumin as the standard.

Yields and purification factor of each step were calculated. The purity factor of the separate active fractions was also evaluated using a SDS electrophoresis in 40 mL polyacrylamide gels.

Both in vitro ferredoxin NADP+ reductase and NADPH ferredoxin reductase activities were evaluated on the recovered pure fraction. According to table 1, the purified enzyme is strictly NADPH/NADP+ dependent:

TABLE 1

Ferredoxin NADP+ reductase and NADPH ferredoxin reductase specific activities on the final purified fraction using methyl viologen as a substrate:

| | Specific activity U/mg protein | | | |
|---|---|---|---|---|
| Activities | Ferredoxin NAD+ reductase | Ferredoxin NADP+ reductase | NADH ferredoxin reductase | NADPH ferredoxin reductase |
| Purified fraction | ND* | 0.43 +/− 0.064 9.5 +/− 1.41# | ND* | 56.5 +/− 2.03 |

*ND: non-detectable;
using reduced ferredoxin (CA_C0303) instead of methyl viologen as the substrate.

1.3—Identification of the Gene Coding for Ferredoxin NADP Reductase Activity:

The region of the gel corresponding to the protein at 45 kDa was cut off using a sterile pipette tip. This gel plug was then used for identification of proteins by mass spectroscopy.

The sample was subjected to trypsin digestion and analyzed by nano LC/MS/MS on a CapLC-Q-TOF2 (Waters) and by MALDI on MALDI MX (Waters). The candidate proteins were identified with the softwares ProteinLynx Global Server (Waters) and Mascot (Matrix Science) using the protein data bank of C. acetobutylicum. For both analyses, there was only one protein identified with a significant score (77% sequence coverage). This 45 kDa protein was shown to be encoded by CA_C0764 a gene annotated to encode for a small subunit of glutamate synthase.

Example 2

Modulation of Ferredoxin NADP Reductase Activity in C. acetobutylicum 2.1—Disruption of CA_C0764 Gene in C. acetobutylicum, Validation of Loss of Ferredoxin NADP+ Reductase Activity and Enhanced Selectivity for Acetone:

To investigate the involvement of CA_C0764 in the in vivo butanol metabolic pathway in C. acetobutylicum, the group II intron-based Clostron technology (Heap J et al. 2007) was used to inactivate the CA_C0764 gene into the C. acetobutylicum ☐cac15 (Soucaille et al. 2006). This technology uses the insertion of a group II intron into a genomic target site coupled to a retrotransposition-activated marker (erythromycin resistance) allowing a stable gene inactivation.

2.1.1: Construction of the C. acetobutylicum Δcac15cac0764-408s::CT Mutant:

The intron target site was identified at the 408/409s bp (from the start of the orf) on the sense strand and intron retargeting PCR primers were designed using a computer algorithm (Perutka et al. 2004):

1-408/409s-IBS consisting of 53 bases
(SEQ ID NO 3)
AAAAAAGCTTATAATTATCCTTAGGCTACAATGTTGTGCGCCCAGATA
GGGTG 2. 408/409s-EBS1d consisting of 60 bases
(SEQ ID NO 4)
CAGATTGTACAAATGTGGTGATAACAGATAAGTCAATGTTACTAACTT
ACCTTTCTTTGT 3. 408/409s-EBS2 consisting of 49 bases
(SEQ ID NO 5)
TGAACGCAAGTTTCTAATTTCGATTTAGCCTCGATAGAGGAAAGTGTCT The three 408/409-IBS, 408/409-IEBS1d, 408/409-EBS2 and the EBS universal primers were used in a single-tube reaction with the pMTL007 plasmid (Heap J. et al. 2007) to mutate the intron at several positions spanning a 350 bp region. The PCR reaction, which re-targets the intron by primer-mediated mutation, was performed according to the Targetron Gene Knockout System kit Protocol (http://www.sigmaaldrich.com/life-science/functional-genomics-and-rnai/targetron.html). The 350 bp PCR fragment was purified and then cloned into the pMTL007 plasmid at the HindIII and BsrGI sites, to replace the original intron fragment. The ligation product was then introduced into Top10 chemically competent E. coli cells (Invitrogen™). Some single colonies were then grown in LB liquid culture supplemented with ampicillin (100 μg/ml), overnight at 37° C., to finally carry out a DNA plasmid extraction (GenElute HP plasmid miniprep kit, Sigma) and check for the presence of the pMTL007:Ca-cac0764-4085 plasmid.

The retargeted plasmid pMTL007:Ca-cac0764-4085 was finally controlled by restriction and by DNA sequencing using the 408/409-IBS and 408/409-IEBS1d primers.

C. acetobutylicum Δcac15 was then electroporated as previously described (Mermelstein et al., 1992) using unmethylated retargeted pMTL007:Ca-cac0764-4085 plasmid, because the CA_C1502 gene encoding the type II restriction endonuclease Cac824I was deleted (Soucaille et al. 2006). After 5 hours of recovery, cells were plated on RCA (Clostridium Nutrient Medium with 15 g/l agar, Fluka (Saint-Quentin Fallavier, France, no 27546) medium supplemented with thiamphenicol (10 μg/ml). Single colonies were chosen from the plate and streaked separately on a RCA plate with erythromycin (40 μg/ml) to select integrants.

The insertion mutants were screened via colony-PCR using the two following primers flanking the target site:

cac0764del_for (SEQ ID NO 6):
(homologous to the sequence 886263 to 886287)
cgagccaataaaatttcacgagata cac0764del_rv (SEQ ID NO 7):
(homologous to the sequence 886512 to 886541)
ccaacctctataagtctttcttcaagctta PCR products were purified and confirmed by DNA sequencing.

One of the colonies was selected to cure the pMTL007:Ca-cac0764-4085 plasmid and generate the C. acetobutylicum Δcac15cac0764408s::CT.

This clone was inoculated into Clostridum Growth Medium (CGM) medium supplemented with erythromycin (40 μg/mL) for successive subcultures, as previously described (Dusséaux et al. 2013). 100 μL of fully grown culture was inoculated into 1 mL fresh CGM medium supplemented with erythromycin (40 μg/mL), grown anaerobically at 37° C. for at least 12 h until full growth achieved. This transfer process was repeated at least 3 times. The last culture was then plated onto solid RCA plate supplemented with erythromycin (40 μg/mL). Colonies were re-streaked successively onto RCA plates supplemented with thiamphenicol (10 µg/mL) and then onto RCA plates supplemented with erythromycin (40 µg/mL). One erythromycin-resistant and thiamphenicol-sensitive clone was selected and inoculated into 3 mL of synthetic medium supplemented with erythromycin (40 µg/mL), grown anaerobically at 37° C. for at least 24 h and transferred in 30 mL synthetic medium supplemented with erythromycin (40 µg/mL). The culture was grown anaerobically at 37° C. for 7 days until sporulation and then the spore suspension was stored at −20° C.

2.1.2: Phenotypic Analysis of the C. acetobutylicum Δcac15cac0764408s::CT Mutant:

C. acetobutylicum Δcac15cac0764408s::CT strain was kept in spore form at −20° C. in the synthetic medium (MS), as previously described (Meynial-Salles et al. 2005). The flask cultures of C. acetobutylicum strains were grown anaerobically in synthetic medium (MS) and were inoculated with spore stock at 10% (v/v) and heat-shocked at 80° C. for 15 min. Cells were grown up at 37° C. during several days, and the pH was maintained by buffering the culture medium with calcium carbonate. As a control, the C. acetobutylicum □cac15 was grown in the same conditions.

The comparative phenotypic analysis was performed by measuring both glucose consumption as well as the concentration of fermentation products as is shown in table 2:

|  | Products yield (% g/g glucose consumed) | | | | | | |
| --- | --- | --- | --- | --- | --- | --- | --- |
|  | Ethanol | Acetone | Butanol | Acetic acid | Lactate | Acetoin | Butyric acid |
| C. acetobutylicum Δcac15 | 1.90 | 9.70 | 23 | 0 | 6 | 3.15 | 1.37 |
| C. acetobutylicum Δcac15cac0764408s::CT | 1.80 | 13.88 | 16.10 | 0 | 5.59 | 5.18 | 1.58 |

The C. acetobutylicum Δcac15cac0764408s::CT strain produces more acetone and less butanol than the control strain.

2.1.3: Ferredoxin NADP+ Reductase Activity Determination in C. acetobutylicum Δcac15cac0764408s::CT Mutant:

C. acetobutylicum Δcac15cac0764408s::CT strain was grown anaerobically in synthetic medium (MS) at 37° C., inoculated with spore stock at 10% (v/v) and heat-shocked at 80° C. for 15 min. Cells were grown up to an approximatively $OD_{620\,nm}$ of 2, and the pH was maintained by buffering the culture medium with calcium carbonate. As a control, the C. acetobutylicum Δcac15 was grown in the same conditions. Cells were transferred into anaerobic chamber, harvested, washed and 20 times concentrated in 100 mM Tris-HCl 2 mM DTT 10% glycerol (pH 7.6) buffer, frozen at −80° C. or immediately used. Cells were further broken by sonication using an ultrasonic disintegrator (vibracell 72434, Bioblock) at 4° C. in four cycles of 30 sec with 2-min intervals. Debris were removed by centrifugation at 8600 g for 10 min, 4° C. (Sigma centrifuge 2-16K) and the acellular crude extract was loaded onto a SephadexG25 column to eliminate salts and metabolites, before the ferredoxin $NADP^+$ reductase activity determination using ferredoxin as a substrate and following the procedure already described in 1.1 (table A).

TABLE A

Ferredoxin $NADP^+$ reductase specific activities determined on crude extracts using ferredoxin as a substrate:

| Strains | Ferredoxin NADP+ reductase specific activity U/mg protein |
| --- | --- |
| C. acetobutylicum Δcac15 | 0.64 |
| C. acetobutylicum Δcac15cac0764408s::CT | 0 |

No ferredoxin $NADP^+$ reductase activity is detected in the acellular crude extract prepared from the C. acetobutylicum Δcac15cac0764408s::CT mutant cells in which the CA_C0764 encoding gene is inactivated.

2 2—Overexpression of CA_C0764 Gene in C. acetobutylicum, Validation of Ferredoxin $NADP^+$ Reductase Activity Increases and Enhanced Selectivity for Butanol:

2.2.1: Construction of the pCLF 0764 for CA_C 0764 Overexpression:

The CA_C0764 gene was amplified from the genomic DNA of C. acetobutylicum ΔTCC824 using primers Ocac07641 and Ocac0764r. The primers were designed to introduce a RBS region along with the CA_C0764 gene, as well as placing BamHI and SfoI restriction sites upstream and downstream respectively:

```
Ocac0764f (SEQ ID NO 8):
AGGATCCATCAAAATTTAGGAGGTTAGTTA

Ocac0764r (SEQ ID NO 9):
GGCGCCTTAATTATTCTTGCAATACTCATCAATAGTTTC
```

The amplified PCR fragment was then subcloned into a Zero Blunt TOPO vector (Invitrogen, Saint Aubin, France) to yield the Zero Blunt TOPO—cac0764 plasmid and sequenced using universal primers T7P and T3P to assure that no mutations were introduced. The fragment containing the CA_C0764 gene was purified on an agarose gel after digestion of the Zero Blunt TOPO—cac0764 vector with BamHI and SfoI. The 7 kb p50594 vector (Dusséaux et al. 2013) was also digested with BamHI and SfoI and ligated to the BamHI-SfoI digested sadh gene, yielding the 6.25 kb p50594-cac0764 vector. The p50594-cac0764 vector was digested with SalI, and the operon-containing fragments from each vector were purified on an agarose gel. The 4.9 kb pCLF1 vector (Soucaille et al. 2006) was digested with SalI, treated with Antarctic phosphatase and ligated with the previously purified fragment to yield the pCLFcac0764.

C. acetobutylicum Δcac15 was then electroporated as previously described (Mermelstein et al., 1992) using unmethylated pCLFcac0764plasmid. After 5 hours of recovery, cells were plated on RCA (*Clostridium* Nutrient Medium with 15 g/l agar, Fluka (Saint-Quentin Fallavier, France, no 27546) medium supplemented with thiamphenicol (10 μg/ml). Single colonies were chosen from the plate and streaked separately on a RCA plate with thiamphenicol (10 μg/ml). The transformants were screened using PCR amplification of the synthetic operon expressing CA_C0764. The cells were then transferred and grown on a MS agar plate with thiamphenicol (10 μg/ml) before inoculation into liquid MS medium. One selected clone was grown anaerobically at 37° C. for 7 days until sporulation and then the spore suspension was stored at −20° C.

2. 2.2: Phenotypic Analysis of the *C. acetobutylicum* Δcac15 pCLF 0764 Mutant:

*C. acetobutylicum* Δcac15pCLF 0764 mutant was kept in spore form at −20° C. in the synthetic medium (MS), as previously described (Meynial-Salles et al. 2005). The flask cultures of *C. acetobutylicum* strains were grown anaerobically in synthetic medium (MS) (at the exception that cystein was omitted) and were inoculated with spore stock at 10% (v/v) and heat-shocked at 80° C. for 15 min. Cells were grown up at 37° C. during several days, and the pH was maintained by buffering the culture medium with calcium carbonate. As a control, the *C. acetobutylicum* Δcac15 was grown in the same conditions.

The comparative phenotypic analysis was performed by measuring both glucose consumption as well as the concentration of fermentation products as is shown in table 3:

TABLE B

Ferredoxin NADP$^+$ reductase specific activities determined on crude extracts using ferredoxin as a substrate:

| Strains | Ferredoxin NADP+ reductase specific activity U/mg protein |
|---|---|
| *C. acetobutylicum* Δcac15 | 0.64 |
| *C. acetobutylicum* Δcac15 pCLFCA_C0764 | 2 |

A 3-fold increase of the ferredoxin NADP$^+$ reductase activity is measured in the acellular crude extract prepared from the *C. acetobutylicum* Δcac15 pCLFCA_C0764 mutant cells in which the CA_C0764 encoding gene is overexpressed from a plasmid.

Example 3

Heterologous Production of Ethanol by a New Metabolic Pathway in an *E. coli* Strain with an Enhanced Ferredoxin NADP$^+$ Reductase Activity 3.1: Construction of an *E. coli* MG1655ΔldhA::FRT, ΔpflAB::FRT, Δack-pta::FRT, ΔiscR::FRT, ΔfrdABCD::FRT Δace::FRT, ΔmgsA Modified Strain 3.1.1 Construction of an *E. coli* MG1655 ΔldhA::FRT-cm-FRT Modified Strain The ldhA gene was replaced with a chloramphenicol antibiotic resistance cassette flanked by Flp recognition target (FRT) that is generated by PCR by using primers with 80-nt homology extensions, deleting most of the gene concerned. The used technique was described by Datsenko and Wanner in 2000.

Two oligonucleotides were designed and used to replace the ldhA gene:

|  | Products yield (% g/g glucose consumed) | | | | | | |
|---|---|---|---|---|---|---|---|
|  | Ethanol | Acetone | Butanol | Acetic acid | Lactate | Acetoin | Butyric acid |
| *C. acetobutylicum* Δcac15 | 1.96 | 9 | 20.9 | −3.47 | 1.15 | 3.75 | 5.34 |
| *C. acetobutylicum* Δcac15 pCLFcac0764 | 8.69 | 4.69 | 25.72 | −3.14 | 0.63 | 1.39 | 3.53 |

The *C. acetobutylicum* □cac15 pCLFcac0764 strain produces less acetone and more butanol and ethanol than the control strain.

2.2.3. Ferredoxin NADP$^+$ Reductase Activity Determination in *C. acetobutylicum* Δcac15 pCLF 0764 Mutant: *C. acetobutylicum* Δcac15 pCLF 0764 mutant was grown anaerobically in synthetic medium (MS), at 37° C., inoculated with spore stock at 10% (v/v) and heat-shocked at 80° C. for 15 min. Cells were grown up to an approximatively OD$_{620\,nm}$ of 2, and the pH was maintained by buffering the culture medium with calcium carbonate. As a control, the *C. acetobutylicum* Δcac15 was grown in the same conditions. Cells were transferred into anaerobic chamber, harvested, washed and 20 times concentrated in 100 mM Tris-HCl 2 mM DTT 10% glycerol (pH 7.6) buffer, frozen at −80° C. or immediately used. Cells were further broken by sonication using an ultrasonic disintegrator (vibracell 72434, Bioblock) at 4° C. in four cycles of 30 sec with 2-min intervals. Debris were removed by centrifugation at 8600 g for 10 min, 4° C. (Sigma centrifuge 2-16K) and the acellular crude extract was loaded onto a SephadexG25 column to eliminate salts and metabolites, before the ferredoxin NADP$^+$ reductase activity determination using ferredoxin as a substrate and following the procedure already described in 1.1 (table B).

1-DldhAr, consisting of 101 bases (SEQ ID NO 10):
ttaaaccagttcgttcgggcaggtttcgccttttccagattgcttaag ttttgcagcgtagtctgagaaatactggtcagCATATGAATATCCTCC

TTAG

With a region (lower-case letters) homologous to the sequence (1439878-1439958) of the ldhA gene (sequence 1439878 to 1440867), a reference sequence on the website http://ecocyc.org/(Keseler et al. 2005) and a region (upper-case letters) for the amplification of the chloramphenicol resistance cassette of the pKD3 plasmid (Datsenko and Wanner 2000).

2. DldhAf, consisting of 100 bases (SEQ ID NO 11):
gaaactcgccgtttatagcacaaaacagtacgacaagaagtacctgcaac aggtgaacgagtcctttggctttgagctggTGTAGGCTGGAGCTGCTTCG With a region (lower-case letters) homologous to the sequence (1440786-1440865) of the ldhA gene (sequence 1439878 to 1440867), a reference sequence on the website http://ecocyc.org/ and a region (upper-case letters) for the amplification of the chloramphenicol resistance cassette carried by the pKD3 plasmid.

Both oligonucleotides DldhAr and DldhAf were used to amplify the chloramphenicol resistance cassette from the pKD3plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the ldhA gene by the chloramphenicol cassette was checked by PCR analysis using both hslJC and ldhAC2 oligonucleotides.

3-hslJC (SEQ ID NO 12):
gccatcagcaggcttagcgc (homologous to the sequence 1439724 to 1439743)

4-ldhAC2 (SEQ ID NO 13):
gggtattgtggcatgtttaaccg (homologous to the sequence 1441007 to 1441029).

The chloramphenicol resistance cassette was then eliminated by using the Flp helper pCP20 plasmid (Cheperanov and Wagernagel 1995). $Cm^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 12 and 13).

3.1.2 Construction of a E. coli MG1655 ΔpflAB::FRT-cm-FRT Modified Strain:

The pflAB genes were replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the pflAB genes:

1. DpflBr, consisting of 100 bases (SEQ ID NO 14):
ccggacatcctgcgttgccgtaaatctggtgttctgaccggtctgccaga tgcatatggccgtggccgtatcatcggtgaCATATGAATATCCTCCTTAG With a region (lower-case letters) homologous to the sequence (952236-952315) of the pflB gene (sequence 950495-952777), a reference sequence on the website http://ecocyc.org/ and a region (upper-case letters) for the amplification of the chloramphenicol resistance cassette of the pKD3 plasmid (Datsenko and wanner 2000).

2. Dpflaf, consisting of 100 bases (SEQ ID NO 15):
gatgcactataagatgtgttaaaaacgctgtagcagaatgaagcgcggaa taaaaaagcggcaactcaataaagttgccgTGTAGGCTGGAGCTGCTTCG With a region (lower-case letters) homologous to the sequence (949470-949549) located upstream the pflA gene (sequence 949563-950303), a reference sequence on the website http://ecocyc.org/and a region (upper-case letters) for the amplification of the chloramphenicol resistance cassette carried by the pKD3 plasmid.

Both oligonucleotides DpflBr and DpflAf were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the pflAB genes by the chloramphenicol cassette was checked by PCR analysis using both pflAB1 and pflAB2 oligonucleotides.

3. pflAB1 (SEQ ID NO 16):
agacattaaaaatatacgtgcagctacccg (homologous to the sequence 948462 to 948491)

4. pflAB2 (SEQ ID NO 17):
gtgaaagctgacaacccttttgatcttta (homologous to the sequence 953660 to 953689).

3.1.3 Construction of an E. coli MG1655 ΔldhA::FRT ΔpflAB:: cm Modified Strain.

Both pflA and pflB genes were then replaced with a chloramphenicol resistance cassette into the MG1655 ΔldhA::FRT strain and the deletion was achieved by generalized P1 phage transduction from the single mutant lysate (Miller 1972).

The $Cm^R$ transductants were selected on plate and the replacement of the pflAB genes by the chloramphenicol cassette into the MG1655ΔldhA::FRT was checked by PCR analysis using both pflAB1 and pflAB2 oligonucleotides. Finally, both hslJC and ldhAC2 primers were also used in PCR analysis to confirm the deletion of ldhA the gene in the strain ΔpflAB::cm. The resulting strain was named MG1655 ΔldhA::FRT ΔpflAB::cm.

The chloramphenicol-resistance cassette was then eliminated by using the Flp helper pCP20 plasmid (Cheperanov and Wagernagel 1995). $Cm^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 16 and 17). The new strain was named MG1655 ΔldhA::FRT ΔpflAB::FRT.

3.1.4 Construction of an MG1655 ΔackA-pta::cm E. coli Modified Strain:

The ackA-pta genes were replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the ackA-pta genes:

1. DackAf, consisting of 100 bases (SEQ ID NO 18):
gtcgagtaagttagtactggttctgaactgcggtagttcttcactgaaat ttgccatcatcgatgcagtaaatggtgaagTGTAGGCTGGAGCTGCTTCG With a region (lower-case letters) homologous to the sequence (2411494-2411573) of the ackA gene (sequence 2411492 to 2412694), a reference sequence on the website http://ecocyc.org/ and a region (upper-case letters) for the amplification of the chloramphenicol resistance cassette of the pKD3 plasmid (Datsenko and Wanner 2000).

2. Dptar, consisting of 97 bases (SEQ ID NO 19):
tgctgtgcagactgaatcgcagtcagcgcgatggtgtagacgatatcgtc aaccagtgcgccacgggacaggtcgttCATATGAATATCCTCCTTAG With a region (lower-case letters) homologous to the sequence (2414906-2414830) of the pta gene (sequence 2412769 to 2414913), a reference sequence on the website http://ecocyc.org/ and a region (upper-case letters) for the amplification of the chloramphenicol resistance cassette carried by the pKD3 plasmid.

Both DackAf and Dptar oligonucleotides were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the ackA pta genes by the chloramphenicol cassette was checked by PCR analysis using both B2295f and YfcCR oligonucleotides.

3. B2295f (SEQ ID NO 20):
gcatgggtaaacttaaggcg (homologous to the sequence 2410902 to 2410921)

4. YfcCr (SEQ ID NO 21):
taatcaccaacgtatcgggc (homologous to the sequence 2415147 to 2415166).

3.1.5: Construction of an E. coli MG1655 ΔldhA::FRT ΔpflAB::FRT ΔackA-pta::FRT Modified Strain Both ackA and pta genes were then replaced with a chloramphenicol resistance cassette flanked by Flp recognition target (FRT) into the MG1655 ΔldhA::FRT ΔpflAB::FRT strain and the deletion was achieved by generalized P1 phage transduction from the single mutant lysate (Miller 1972).

The Cm$^R$ transductants were selected on plate and the replacement of the ackA pta genes by the chloramphenicol cassette into the MG1655 ΔldhA::FRT ΔpflAB::FRT was checked by PCR analysis using both B2295f and YfcCr oligonucleotides. Finally, both i) hslJC and ldhAC2 and pFlAB1 and pflAB2 couple of primers were also used in PCR analysis to confirm the deletion of ldhA and pflAB genes in the strain ΔackA-pta::cm. The resulting strain was named MG1655 ΔldhA::FRTΔpflAB::FRTΔackA-pta::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 20 and 21). The new strain was named MG1655 ΔldhA::FRT ΔpflAB::FRT ΔackA-pta::FRT.

3.1.7. Construction of an E. coli MG1655 ΔiscR::km Modified Strain

The iscR gene was replaced with a kanamycin antibiotic resistance cassette flanked by Flp recognition target (FRT) that is generated by PCR by using primers with 50-nt homology extensions, deleting most of the concerned gene. The used technique was described by Datsenko and Wanner in 2000.

Two oligonucleotides were designed and used to replace the iscR gene:

1. DiscRf, consisting of 70 bases (SEQ ID NO 22):
tacaataaaaaacccccgggcaggggcgagtttgaggtgaagtaagacatg

ATTCCGGGGATCCGTCGACC

With a region (lower-case letters) homologous to the sequence (2660151-2660200) corresponding to the upstream chromosomal sequence of the iscR gene (sequence 2659665 to 2660153), a reference sequence on the website http://ecocyc.org/, including the iscR gene initiation codon, and a region (upper-case letters) for the amplification of the kanamycin resistance cassette carried by the pKD13 plasmid.

2. DiscRr, consisting of 70 bases (SEQ ID NO 23):
cactccggcctgattctgaattctttttattaagcgcgtaacttaacgtc

TGTAGGCTGGAGCTGCTTCG

With a region (lower-case letters) homologous to the sequence (2659636-2659685) corresponding to the downstream chromosomal sequence of the iscR gene (sequence 2659665 to 2660153), a reference sequence on the website http://ecocyc.org/, including the codons for the six C-terminal residues and the stop codon of the iscR gene, and a region (upper-case letters) for the amplification of the kanamycin resistance cassette of the pKD13 plasmid Datsenko and Wanner in 2000. Both DiscRf and DiscRr oligonucleotides were used to amplify the kanamycin resistance cassette from the pKD13 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the iscR gene by the chloramphenicol cassette was checked by PCR analysis using both iscr1s and iscr1rv oligonucleotides.

3. iscr1s (SEQ ID NO 24):
cgccgcatccgacaacagg (homologous to the sequence 2660325 to 2660343)

4. iscr1rv (SEQ ID NO 25):
tgctggtgatgatgtgcttgcct (homologous to the sequence 2659253 to 2659275).

3.1.8. Construction of an E. coli MG1655 ΔldhA::FRTΔpflAB::FRTΔackA-pta::FRT ΔiscR::FRT Modified Strain:

The iscR gene was then replaced with a kanamycin resistance cassette into the MG1655 ΔldhA::FRTΔpflAB::FRTΔackA-pta::FRT strain and the deletion was achieved by generalized P1 phage transduction from the single mutant lysate (Miller 1972).

The Km$^R$ transductants were selected on plate and the replacement of the iscR gene by the kanamycin cassette into the MG1655ΔldhA::FRTΔpflAB::FRTΔackA-pta::FRT was checked by PCR analysis using both iscrs and iscr1rv oligonucleotides. Finally, i) hslJC and ldhAC2, ii) pFLAB1 and pflAB2 and iii) B2295f and YfcCR couple of primers were also used in PCR analysis to confirm the deletion of ldhA, pflAB and ackA-pta genes respectively in the strain ΔiscR::km. The resulting strain was named MG1655 ΔldhA::FRTΔpflAB::FRTΔackA-pta::FRTΔiscR::km. The kanamycin-resistance cassette was then eliminated by using the Flp helper pCP20 plasmid (Cheperanov and Wagernagel 1995). Km$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 24 and 25). The new strain was named MG1655 ΔldhA:: FRTΔpflAB::FRTΔackA-pta::FRTΔiscR::FRT.

3.1.9 Construction of a E. coli MG1655 ΔfrdABCD::cm Modified Strain:

The frdA, frdB, frdC and frdD genes were replaced with a chloramphenicol antibiotic resistance cassette flanked by Flp recognition target (FRT) that is generated by PCR by using primers with 50-nt homology extensions, deleting most of the concerned genes. The used technique was described by Datsenko and Wanner in 2000.

Two oligonucleotides were designed and used to replace the frdA, frdB, frdC and frdD genes:

```
1. DfrdAf, consisting of 70 bases (SEQ ID No 26):
acctgaagtacgtggctgtgggataaaaacaatctggaggaatgtcgtg

TGTAGGCTGGAGCTGCTTCG
```

With a region (lower-case letters) homologous to the sequence (4380339-4380388) corresponding to the upstream chromosomal sequence of the frdA gene (sequence 4378533 to 4380341), a reference sequence on the website http://ecocyc.org/, including the frdA gene initiation codon, and a region (upper-case letters) for the amplification of the chloramphenicol resistance cassette of the plasmid pKD3 (Datsenko and Wanner in 2000).

```
2. DfrdDr, consisting of 70 bases (SEQ ID No 27):
aggcgggccggatttacattggcgatgcgttagattgtaacgacaccaat

CATATGAATATCCTCCTTAG
```

With a region (lower-case letters) homologous to the sequence (4377001-4377050) corresponding to the downstream chromosomal sequence of the frdD gene (sequence 4377030 to 4377389), a reference sequence on the website http://ecocyc.org/, including the codons for the six C-terminal residues and the stop codon of the frdD gene, and a region (upper-case letters) for the amplification of the chloramphenicol resistance cassette carried by the plasmid pKD3.

Both DfrdAf and DfrdDr oligonucleotides were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the frdABCD genes by the chloramphenicol cassette was checked by PCR analysis using both frdABCD1s and frdABCD1rv oligonucleotides.

```
3. frdABCD1s (SEQ ID NO 28):
ctggctcatacaaggcgtctcc (homologous to the sequence
4380779 to 4380800)

4. frdABCD1rv (SEQ ID NO 29):
tcccattccactgtttagcggta (homologous to the sequence 4376610 to 4376632).
```

3.1.10 Construction of an E. coli MG1655 ΔldhA:: FRTΔpflAB::FRT ΔackA-pta::FRT ΔiscR::FRT ΔfrdABCD::FRT Modified Strain:

The frdABCD genes were then replaced with a chloramphenicol resistance cassette into the MG1655ΔldhA:: FRTΔpflAB::FRTΔackA-pta::FRTΔiscR::FRT strain and the deletion was achieved by generalized P1 phage transduction from the single mutant lysate (Miller 1972). The Cm$^R$ transductants were selected on plate and the replacement of the frdABCD genes by the chloramphenicol cassette into the MG1655ΔldhA::FRTΔpflAB::FRTΔackA-pta::FRT ΔiscR:: FRT was checked by PCR analysis using both frdABCD1s and frdABCD1rv oligonucleotides. Finally, i) hslJC and ldhAC2, ii) pFLAB1 and pflAB2 iii) B2295f and YfcCR and iv) iscr1s and iscr1rv couple of primers were also used in PCR analysis to confirm the deletion of ldhA, pflAB ackA-pta and iscR genes respectively, in the strain ΔiscR::km. The resulting strain was named MG1655ΔldhA::FRT ΔpflAB:: FRTΔackA-pta::FRTΔiscR::FRTΔfrdABCD::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 28 and 29). The new strain was named MG1655ΔldhA::FRTΔpflAB::FRT ΔackA-pta::FRTΔiscR:: FRTΔfrdABCD::FRT.

3.1.11 Construction of an E. coli MG1655 ΔaceE::km Modified Strain:

The aceE gene was replaced with a kanamycin antibiotic resistance cassette flanked by Flp recognition target (FRT) that is generated by PCR by using primers with 50-nt homology extensions deleting most of the concerned gene. The used technique was described by Datsenko and Wanner in 2000.

Two oligonucleotides were designed and used to replace the aceE gene:

```
1. DaceEf, consisting of 70 bases (SEQ ID NO 30):
acaggttccagaaaactcaacgttattagatagataaggaataacccatg

ATTCCGGGGATCCGTCGACC
```

With a region (lower-case letters) homologous to the sequence (122970-123019) corresponding to the upstream chromosomal sequence of the aceE gene (sequence 123017 to 125680), a reference sequence on the website http://ecocyc.org/, including the aceE gene initiation codon, and a region (upper-case letters) for the amplification of the kanamycin resistance cassette carried by the pKD13 plasmid (Datsenko and Wanner 2000).

2. DaceEr, consisting of 70 bases (SEQ ID NO 31):
gatttcgatagccattattatttacctcttacgccagacgcgggttaacT

GTAGGCTGGAGCTGCTTCG

With a region (lower-case letters) homologous to the sequence (125660-125709) corresponding to the downstream chromosomal sequence of the aceE gene (sequence 123017 to 125680), a reference sequence on the website http://ecocyc.org/, including the codons for the six C-terminal residues and the stop codon of the aceE gene and a region (upper-case letters) for the amplification of the kanamycin resistance cassette of the pKD13 plasmid (Datsenko and Wanner 2000).

Both DaceEf and DaceEr oligonucleotides were used to amplify the kanamycin resistance cassette from the pKD13 plasmid. The amplified PCR fragment was then introduced by electroporation into the MG1655 *E. coli* strain carrying the RED plasmid helper (pKD46) expressing the system α, β and exo genes encoding Gam, Bet and Exo recombinases to promote homologous recombination. The antibiotic-resistant transformants were then selected and the replacement of the aceE gene by the kanamycin cassette was checked by PCR analysis using both aceEs and aceErv oligonucleotides.

3. aceEs (SEQ ID NO 32): gagagccgccgtgagcgttc
(homologous to the sequence 122806 to 122825)

4. aceErv (SEQ ID NO 33): ctgcaccgtcggcggaatcg
(homologous to the sequence 125916 to 125935).

3.1.12. Construction of an *E. coli* MG1655ΔldhA::FRTΔpflAB::FRTΔackA-pta::FRTΔiscR::FRTΔfrdABCD::FRTΔaceE::FRT Modified Strain:

The aceE gene was then replaced with a kanamycin resistance cassette into the MG1655 ΔldhA::FRTΔpflAB::FRTΔackA-pta::FRTΔiscR::FRTΔfrdABCD::FRT strain and the deletion was achieved by generalized P1 phage transduction from the single mutant lysate (Miller 1972).

The km$^R$ transductants were selected on plate and the replacement of the aceE gene by the kanamycin cassette into the MG1655ΔldhA::FRTΔpflAB::FRTΔackA-pta::FRTΔiscR ::FRTΔfrdABCD::FRT was checked by PCR analysis using both aceEs and aceErv oligonucleotides. Finally, both i) hslJC and ldhAC2, ii) pFLAB1 and pflAB2 iii) B2295f and YfcCR, iv) iscr1s and iscr1rv and v) frdABCD1s and frdABCD1rv primers were also used in PCR analysis to confirm the deletion of ldhA, pflAB, ackA-pta, iscR and frdABCD genes respectively in the strain ΔaceE::kan. The resulting strain was named MG1655 ΔldhA::FRT ΔpflAB::FRTΔackA-pta::FRTΔiscR::FRTΔaceE::km.

The kanamycin-resistance cassette was then eliminated by using the Flp helper pCP20 plasmid (Cheperanov and Wagernagel 1995). Km$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 32 and 33). The new strain was named MG1655ΔldhA::FRTΔpflAB::FRTΔackA-pta::FRTΔiscR::FRTΔfrdABCD::FRT ΔaceE::FRT.

3.1.13. Construction of an *E. coli* MG1655 ΔmgsA::cm Modified Strain:

The mgsA gene was replaced with a chloramphenicol antibiotic resistance cassette flanked by Flp recognition target (FRT) that is generated by PCR by using primers with 50-nt homology extensions deleting most of the concerned gene. The used technique was described by Datsenko and Wanner in 2000.

Two oligonucleotides were designed and used to replace the mgsA gene:

1. DmgsAf, consisting of 70 bases (SEQ ID NO 34):
taagtgcttacagtaatctgtaggaaagttaactacggatgtacattatg

TGTAGGCTGGAGCTGCTTCG

With a region (lower-case letters) homologous to the sequence (1026236-1026285) corresponding to the upstream chromosomal sequence of the mgsA gene (sequence 1025780 to 1026238), a reference sequence on the website http://ecocyc.org/, including the mgsA gene initiation codon, and a region (upper-case letters) for the amplification of the chloramphenicol resistance cassette of the pKD3 plasmid.

2. DmgsAr, consisting of 70 bases (SEQ ID NO 35):
aacaggtggcgtttgccacctgtgcaatattacttcagacggtccgcgag

CATATGAATATCCTCCTTAG

With a region (lower-case letters) homologous to the sequence (1025751-1025800) corresponding to the downstream chromosomal sequence of the mgsA gene (sequence 1025780 to 1026238), a reference sequence on the website http://ecocyc.org/, including the codons for the six C-terminal residues and the stop codon of the mgsA gene and a region (upper-case letters) for the amplification of the chloramphenicol resistance cassette carried by the pKD3 plasmid.

Both DmgsAf and DmgsAr oligonucleotides were used to amplify the chloramphenicol resistance cassette from the pKD3 plasmid. The amplified PCR fragment was then introduced by electroporation into the MG1655 *E. coli* strain carrying the RED plasmid helper (pKD46) expressing the system α, β and exo genes encoding Gam, Bet and Exo recombinases to promote homologous recombination. The antibiotic-resistant transformants were then selected and the replacement of the mgsA gene by the chloramphenicol cassette was checked by PCR analysis using both mgsAs and mgsArv oligonucleotides.

3. mgsAs (SEQ ID NO 36): cccagctcatcaaccaggtc
(homologous to the sequence 1026715 to 1026734)

4. mgsArv (SEQ ID NO 37): ggagtcgattatggaagaggcg
(homologous to the sequence 1025559 to 1025580).

3.1.14. Construction of an *E. coli* MG1655ΔldhA::FRTΔpflAB::FRTΔackA-pta::FRTΔiscR::FRTΔfrdABCD::FRTΔaceE::FRTΔmgsA::FRT Modified Strain.

The mgsA gene was then replaced with a chloramphenicol resistance cassette into the MG1655ΔldhA::FRT ΔpflAB::FRTΔackA-pta::FRTΔiscR::FRT ΔfrdABCD::FRTΔaceE::FRT strain and the deletion was achieved by generalized P1 phage transduction from the single mutant lysate (Miller 1972).

The Cm$^R$ transductants were selected on plate and the replacement of the mgsA gene by the chloramphenicol cassette into the MG1655ΔldhA::FRTΔpflAB::FRTΔackA-pta::FRTΔiscR ::FRTΔfrdABCD::FRTΔaceE::FRT was checked by PCR analysis using both mgsAs and mgsArv oligonucleotides. Finally, i) hslJC and ldhAC2, ii) pFLAB1 and pflAB2 iii) B2295f and YfcCR, iv) iscr1s and iscr1rv v) frdABCD1s and frdABCD1rv and vi) aceEs and aceErv primers were also used in PCR analysis to confirm the deletion of ldhA, pflAB, ackA-pta, iscR, frdABCD and aceE genes respectively in the strain ΔmgsA::cm. The resulting strain was named MG1655 ΔldhA::FRT ΔpflAB::FRTΔackA-pta::FRTΔiscR::FRTΔfrdABCD::FRT ΔaceE::FRTΔmgsA::cm. The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 36 and 37). The new strain was named MG1655 ΔldhA::FRTΔpflAB::FRTΔackA-pta::FRTΔiscR::FRTΔfrdABCD::FRT ΔaceE::FRTΔmgsA::FRT.

3.2. Construction of the pSC101-pGI1.6-cac2229-cac0764-cac0303 Expression Vector Three CA_C2229, CA_C0764, CA_C0303 synthetic genes encoding the pyruvate ferredoxin oxidoreductase, the ferredoxin NADP reductase and the ferredoxin respectively, from *Clostridium acetobutylicum* were firstly designed using the method termed codon harmonization (Angov et al. 2008). Synonymous codons from *E. coli* that match as closely as possible the codon usage frequency used in the native genes from *C. acetobutylicum* were selected. Based on the generated sequences, the synthetic genes were further synthetized by Life Technologies (ThermoFisher Scientific, Saint aubin, France) introducing the native RBS region along with each gene, as well as placing two unique restriction sites upstream and downstream each gene. Each synthetic gene with its RBS region flanked by two unique restriction sites were then subcloned into the pCR4TOPO vector (Invitrogen, Saint Aubin, France), before to be cloned as an operon into a low-copy pSC101-derived plasmid (Bernardi and Bernardi 1984) under the control of the GI 1.6 promoter (Meynial-Salles et al. 2005, Soucaille et al. 2012) and upstream the adc terminator (from *C. acetobutylicum*) to yield the 9.54 kb pSC101-pGI-cac2229-cac0764-cac0303 plasmid.

3.3. Introduction of the pSC101-PGI-cac2229-cac0764-cac0303 Expression Vector into the MG1655 ΔldhA::FRTΔpflAB::FRTΔackA-pta::FRTΔiscR::FRTΔfrdABCD::FRT ΔaceE::FRTΔmgsA::FRT *E. coli* Strain.

ThepSC101-PGI-cac2229-cac0764-cac0303 expression vector was used to transform the MG1655 ΔldhA::FRTΔpflAB::FRTΔackA-pta::FRTΔiscR::FRTΔfrdABCD::FRT ΔaceE::FRTΔmgsA::FRT by electroporation (Sambrook and Russel 2001).

The transformants were selected on LB agar plates supplemented with spectinomycin (70 µg/ml) at 37° C. Some transformants were then grown in LB liquid culture supplemented with spectinomycin (100 µg/ml) overnight at 37° C. to carry out a DNA plasmid extraction (GenElute HP plasmid miniprep kit, Sigma) and check for the presence of the pSC101-PGI-cac2229-cac0764-cac0303 plasmid. The pSC101-PGI-cac2229-cac0764-cac0303 plasmid was finally controlled by restriction profile.

The final *E. coli* MG1655 ΔldhA::FRTΔpflAB::FRTΔackA-pta::FRTΔiscR::FRTΔfrdABCD::FRT ΔaceE::FRTΔmgsA::FRT (pSC101-PGI-cac2229-cac0764-cac0303) was grown in LB liquid medium supplemented with spectinomycin (100 µg/ml) and kept in 20% glycerol solution at −80° C.

3.4.: Physiological Characterization of the MG1655 ΔldhA::FRTΔpflAB::FRTΔackA-pta::FRTΔiscR::FRTΔfrdABCD::FRT ΔaceE::FRTΔmgsA::FRT (pSC101-pGI1.6-cac2229-cac0764-cac0303) *E. coli* Strain:

The MG1655 ΔldhA::FRTΔpflAB::FRTΔackA-pta::FRTΔiscR::FRTΔfrdABCD::FRT ΔaceE::FRTΔmgsA::FRT (pSC101-pGI1.6-cac2229-cac0764-cac0303) *E. coli* strain was grown anaerobically on a 20 g/L glucose mineral medium containing minerals salts as previously described (Meynial-salles et al. 2005) supplemented with 4 g/l of yeast extract, 5 mM sodium nitrate and spectinomycin (100 µg/ml) and inoculated with 100 µl of a LB overnight culture. Cells were grown up at 37° C. during several days, and the pH was maintained by buffering the culture medium with MOPS. As controls, both the MG1655 ΔldhA::FRTΔpflAB::FRTΔackApta::FRTΔiscR::FRTΔfrdABCD::FRTΔaceE::FRTΔmgsA::FRT *E.coli* (without plasmid) and the MG1655 ΔldhA::FRTΔpflAB::FRTΔackApta::FRTΔiscR::FRTΔfrdABCD::FRTΔaceE::FRTΔmgsA::FRT (pSC101-pGI1.6-cac2229-cac0303) (without the cac0764 gene) were grown in the same conditions.

The comparative phenotypic analysis was performed by measuring glucose consumption as well as the concentration of fermentation products for the culture of each strain as is shown in table 3:

| Strains | Glucose consumption (g/L) | Products yield (% g/g glucose consumed) | | | | | |
|---|---|---|---|---|---|---|---|
| | | Pyruvate | Succinate | Lactate | Formate | Acetate | Ethanol | CO$_2$ |
| MG1655ΔldhA::FRTΔpflAB::FRTΔackApta::FRTΔiscR::FRTΔfrdABCD::FRTΔaceE::FRTΔmgsA::FRT | 2.27 | 87.7 | 1.54 | 0.66 | 1.45 | 4.84 | 17 | 19.86 |
| MG1655ΔldhA::FRTΔpflAB::FRTΔackApta::FRTΔiscR::FRTΔfrdABCD::FRTΔaceE::FRTΔmgsA::FRT (pSC101-pGI1.6-cac2229-cac0303) | 3.14 | 37.90 | 3.18 | 3.82 | 2.23 | 1.27 | 23.89 | 23.71 |
| MG1655ΔldhA::FRTΔpflAB::FRTΔackApta::FRTΔiscR::FRTΔfrdABCD::FRTΔaceE::FRTΔmgsA::FRT (pSC101-pGI1.6-cac2229-cac0764-cac0303 | 20.23 | 2.37 | 0.84 | 6.13 | 0.00 | 1.43 | 42.46 | 41.31 |

As shown in table 3, the expression of the complete synthetic CA_C2229-CA_C0764-CA_C0303 operon into the MG1655 ΔldhA::FRTΔpflAB::FRTΔackApta::FRTΔiscR::FRTΔfrdABCD::FRTΔaceE::FRTΔmgsA::FRT *E.coli* led to the production of ethanol as the main fermentation product from glucose at a yield of 42.5 g/g glucose consumed corresponding to 83% of the theoretical yield. Moreover, the expression of the complete synthetic CA_C2229-CA_C0764-CA_C0303 operon favoured the growth which was strongly hampered in both control strains as the strains were unable to balance the redox.

3.5. Ferredoxin NADP+ reductase activity determination in the MG1655 ΔldhA::FRTΔpflAB::FRTΔackA-pta::FRTΔiscR::FRTΔfrdABCD::FRT ΔaceE::FRTΔmgsA::FRT (pSC101-pGI1.6-cac2229-cac0764-cac0303) E. coli Strain:

The MG1655 ΔldhA::FRTΔpflAB::FRTΔackA-pta::FRTΔiscR::FRTΔfrdABCD::FRT ΔaceE::FRTΔmgsA::FRT (pSC101-pGI1.6-cac2229-cac0764-cac0303) E. coli strain was grown anaerobically on a 20 g/L glucose mineral medium containing minerals salts as previously described (Meynial-salles et al. 2005) supplemented with 4 g/l of yeast extract, 5 mM sodium nitrate and spectinomycin (100 µg/ml) and inoculated with 100 µl of a LB overnight culture. Cells were grown up at 37° C. up to an approximatively $OD_{550\ nm}$ of 2, and the pH was maintained by buffering the culture medium with MOPS. As controls, both the MG1655 ΔldhA::FRTΔpflAB::FRTΔackApta::FRTΔiscR::FRTΔfrdABCD::FRTΔaceE::FRTΔmgsA::FRT (pSC101-pGI1.6-cac2229-cac0303) (without the cac0764 gene) were grown in the same conditions. Cells were transferred into anaerobic chamber, harvested, washed and 20 times concentrated in 100 mM Tris-HCl 2 mM DTT 10% glycerol (pH 7.6) buffer, frozen at −80° C. or immediately used. Cells were further broken by sonication using an ultrasonic disintegrator (vibracell 72434, Bioblock) at 4° C. in four cycles of 30 sec with 2-min intervals. Debris were removed by centrifugation at 8600 g for 10 min, 4° C. (Sigma centrifuge 2-16K) and the acellular crude extract was loaded onto a SephadexG25 column to eliminate salts and metabolites, before the ferredoxin $NADP^+$ reductase activity determination using ferredoxin as a substrate and following the procedure already described in 1.1 (table C).

TABLE C

Ferredoxin $NADP^+$ reductase specific activities determined on crude extracts using ferredoxin as a substrate:

| Strains | Ferredoxin NADP+ reductase specific activity U/mg protein |
|---|---|
| MG1655ΔldhA::FRTΔpflAB::FRTΔackApta::FRTΔiscR::FRTΔfrdABCD::FRTΔaceE::FRTΔmgsA::FRT(pSC101-pGI1.6-cac2229-cac0303) | 0 |
| MG1655ΔldhA::FRTΔpflAB::FRTΔackApta::FRTΔiscR::FRTΔfrdABCD::FRTΔaceE::FRTΔmgsA::FRT (pSC101-pGI1.6-cac2229-cac0764-cac0303 | 0.08 |

As shown in table C, a ferredoxin $NADP^+$ reductase activity is only detected into the E. coli modified strain expressing the CA_C0764 encoding gene.

Example 4

Heterologous Production of n-Butanol by a New Metabolic Pathway in an E. coli Strain with an Enhanced Ferredoxin $NADP^+$ Eductase Activity 4.1: Construction of an E. coli MG1655ΔldhA::FRT, ΔpflAB::FRT, Δack-pta::FRT, ΔiscR::FRT, ΔfrdABCD::FRT Δace::FRT, ΔmgsA::FRT ΔadhE::FRT ΔmelB::TT02-Ptrc01/RBSOP2-crt-hbd-TT07-FRT ptrc30/RBS01*2-atoB-FRT Modified Strain 4.1.1: Construction of an E. coli MG1655 ΔadhE::FRT-cm-FRT Modified Strain:

The adhE gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the adhE gene:

DadhE r de 100 bases (SEQ ID No 38):
atggctgttactaatgtcgctgaacttaacgcactcgtagagcgtgtaa aaaaagcccagcgtgaatatgccagtttcactCATATGAATATCCT

CCTTAG

With a region (lower-case letters) homologous to the sequence (1297264-1297344) including the adhE gene initiation codon of the adhE gene (sequence 1294669 to 1297344), a reference sequence on the website http://ecocyc.org/, and a region (upper-case letters) for the amplification of the chloramphenicol resistance cassette of the pKD3 plasmid.

DadhEf de 100 bases (SEQ ID NO 39):
ttaagcggattttttcgcttttttctcagctttagccggagcagcttct ttcttcgctgcagtttcaccttctacataatTGTAGGCTGGAGCTG

CTTCG

With a region (lower-case letters) homologous to the sequence (1294693-1294748) corresponding to the downstream chromosomal sequence of the adhE gene (sequence 1294669 to 1297344), a reference sequence on the website http://ecocyc.org/ and a region (upper-case letters) for the amplification of the chloramphenicol resistance cassette carried by the pKD3 plasmid.

Both DadhEf and DadhEr oligonucleotides were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the adhE gene by the chloramphenicol cassette was checked by PCR analysis using both ychGf and adhECr oligonucleotides.

ychGf (SEQ ID NO 40): ggctcattgcaccaccatccag
(homologous to the sequence 1294357 to 1294378)

adhECr (SEQ ID NO 41): gaaaagacgcgctgacaatacgcc
(homologous to the sequence 1297749 to 1297772).

4.1.2. Construction of an E. coli MG1655ΔldhA::FRTΔpflAB::FRTΔackA-pta::FRTΔiscR::FRTΔfrdABCD::FRTΔaceE::FRTΔmgsA::FRTΔadhE::FRT Modified Strain.

The adhE gene was then replaced with a chloramphenicol resistance cassette into the MG1655ΔldhA::FRT ΔpflAB::FRTΔackA-pta::FRTΔiscR::FRT ΔfrdABCD::FRTΔaceE::

FRT ΔmgsA::FRT strain and the deletion was achieved by generalized P1 phage transduction from the single mutant lysate (Miller 1972).

The $Cm^R$ transductants were selected on plate and the replacement of the adhE gene by the chloramphenicol cassette into the MG1655ΔldhA::FRT ΔpflAB::FRT ΔackA-pta::FRTΔiscR::FRT ΔfrdABCD::FRTΔaceE::FRT ΔmgsA::FRT was checked by PCR analysis using both ychGf and adhECr oligonucleotides. Finally, i) hslJC and ldhAC2, ii) pFLAB1 and pflAB2 iii) B2295f and YfcCR, iv) iscr1s and iscr1rv v) frdABCD1s and frdABCD1rv vi) aceEs and aceErv and vii) mgsAs and mgsArv couple of primers were also used in PCR analysis to confirm the deletion of ldhA, pflAB, ackA-pta, iscR, frdABCD, aceE, mgsA genes respectively in the strain ΔadhE::cm. The resulting strain was named MG1655 ΔldhA::FRT ΔpflAB::FRTΔackA-pta::FRTΔiscR::FRTΔfrdABCD::FRT ΔaceE::FRTΔmgsA::FRTΔadhE::cm.

The chloramphenicol-resistance cassette was then eliminated by using the Flp helper pCP20 plasmid (Cheperanov and Wagernagel 1995). $Cm^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 40 and 41). The new strain was named MG1655 ΔldhA::FRTΔpflAB::FRTΔackA-pta::FRTΔiscR::FRTΔfrdABCD::FRT ΔaceE::FRTΔmgsA::FRTΔadhE::FRT.

4.1.3. Construction of an *E. coli* MG1655ΔmelB::TT02-ptrc01/RBS01*2-crt-hbd-TT07-Km modified strain Both CA_C2712 and CA_C2708 synthetic genes encoding the crotonase and the β-hydroxy-butyrylCoA dehydrogenase respectively, from *Clostridium acetobutylicum* were firstly designed using the method termed codon harmonization (Angov et al. 2008). Synonymous codons from *E. coli* that match as closely as possible the codon usage frequency used in the native genes from *C. acetobutylicum* were selected. Based on the generated sequences, the synthetic genes were further synthetized in operon by Life Technologies (ThermoFisher Scientific, Saint aubin, France) introducing the RBS01 region along with each gene, as well as placing two unique restriction sites upstream and downstream each gene. The synthetic crt-hbd operon was then cloned under the control of ptrc01 promoter into the pUC18-TTadc-CI*0-PlambdaR*(−35)-ΔmelB::Km (Norrander et al. 1983) carrying two homologous region of the melB locus and the kanamycin resistant cassette. The plasmid was digested with SmaI-BamHI and ligated with the SmaI-crt-hbd-BamHI synthetic operon to yield the pUC18-TTadc-CI*0-PlambdaR*(−35)-ΔmelB::TT02-ptrc01/RBS01*2-crt-hbd-TT07-Km plasmid.

Both ome1847 and ome1850 primers were then used in a single tube PCR reaction with the pUC18-TTadc-CI*0-PlambdaR*(−35)-ΔmelB::TT02-Ptrc01/RBS01*2-crt-hbd-TT07-Km plasmid to amplify the TT02-ptrc01/RBS01*2-crt-hbd-TT07::Km region.

Ome1847
                                         (SEQ ID No 42)
TTCGTCACGGAATCGTCAGAAC

Ome1850
                                         (SEQ ID No 43)
CCTGATTTATACCGGCATTTCGG

The amplified PCR fragment was then introduced by electroporation into the MG1655 *E. coli* strain carrying the RED plasmid helper (pKD46) expressing the system α, β and exo genes encoding Gam, Bet and Exo recombinases to promote homologous recombination. The antibiotic-resistant transformants were then selected and the replacement of the melB gene by the TT02-ptrc01/RBS01*2-crt-hbd-TT07-Km cassette was checked by PCR analysis using both ome1845 and 1846rv oligonucleotides. The final strain was named MG1655 ΔmelB::TT02-ptrc01/RBS01*2-crt-hbd-TT07-Km.

ome1845s
                                         (SEQ ID No 44)
gccgatttttgtcgtggtggc (homologous to the sequence
from 4340168 to 4340187)

ome1846rv
                                         (SEQ ID No 45)
gccggttatccatcaggttcac (homologous to the sequence
from 4344065 to 4344044)

4.1.4 Construction of an *E. coli* MG1655ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-ptrc01/RBS01*2-crt-hbd-TT07-FRT Modified Strain The melB locus into the MG1655ΔldhA::FRTΔpflAB::FRTΔackA-pta::FRTΔiscR::FRTΔfrdABCD::FRT ΔaceE::FRTΔmgsA::FRTΔadhE::FRT *E. coli* strain was then replaced by the ptrc01/RBS01*2-crt-hbd-TT07::Km synthetic operon and the replacement was achieved by generalized P1 phage transduction from the single mutant lysate (Miller 1972). The $Km^R$ transductants were selected on plate and the replacement of the melB gene by the ptrc01/RBS01*2-crt-hbd-TT07-Km synthetic operon into the MG1655ΔldhA::FRT ΔpflAB::FRT ΔackA-pta::FRTΔiscR::FRT ΔfrdABCD::FRTΔaceE::FRT ΔmgsA::FRTΔadhE::FRT was checked by PCR analysis using both ome1845 and 1846rv oligonucleotides. Finally, i) hslJC and ldhAC2, ii) pFLAB1 and pflAB2 iii) B2295f and YfcCR, iv) iscr1s and iscr1rv v) frdABCD1s and frdABCD1 rv vi) aceEs and aceErv vii) mgsAs and mgsArv and viii) ychGf and adhECr couple of primers were also used in PCR analysis to confirm the deletion of ldhA, pflAB, ackA-pta, iscR, frdABCD, aceE, mgsA and adhE genes respectively in the strain ΔmelB::TT02-ptrc01/RBS01*2-crt-hbd-TT07-Km. The resulting strain was named MG1655 ΔldhA::FRT ΔpflAB::FRTΔackA-pta::FRTΔiscR::FRTΔfrdABCD::FRT ΔaceE::FRTΔmgsA::FRTΔadhE::FRT ΔmelB::TT02-ptrc01/RBS01*2-crt-hbd-TT07-Km.

The kanamycin-resistance cassette was then eliminated by using the Flp helper pCP20 plasmid (Cheperanov and Wagernagel 1995). $Km^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 44 and 45). The new strain was named MG1655 ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-ptrc01/RBS01*2-crt-hbd-TT07-FRT.

4.1.5. Construction of an *E. coli* MG1655 ptrc30/RBS01*2-atoB-cm Modified Strain:

Both Ome1246 and Odi0247 oligonucleotides were used to amplify the chloramphenicol resistance cassette from the pKD3 plasmid and introduced ptrc30 and RBS01 regions upstream the atoB gene and replace the natural promoter region.

Ome1246_3'D r (SEQ ID 46)

TGTAGGCTGGAGCTGCTTCG

Homologous to a region for the amplification of the chloramphenicol resistance cassette of the pKD3 plasmid Odi 0247_Ptrc30/RBS01*2-atoB R r (SEQ ID 47)

CAATTTTTCATtataacctccttaTTCCACACAGTATACGAGCCGGAT

GATTAATCGTCAACAGCTCCATGGTC<u>CATATGAATATCCTCTTA</u>

With a region (bold letters) homologous to the sequence 2324141-2324131 of the atoB gene (sequence 2 324 131 to 2 325 315) a reference sequence on the website http://ecocyc.org/, a region (lower case letters) homologous to the RBS01*2 consensus sequence containing the PsiI restriction site, a region (italic letters) containing the artficial ptrc30 promoter and a region (underlined letters) for the amplification of the chloramphenicol resistance cassette of the pKD3 plasmid.

The PCR product was then purified and used for a second PCR using both Odi0242 and 0246 oligonucleotides to increase the size of homologous regions and, finally, favour in vivo homologous recombination.

Odi 0242

(SEQ ID No 48)

GCATCACTGCCCTGCTCTTCTCCGGTGTCATTTTCGTCATTGGTTTAAC

GCTGTTCTGACGGCACCCCTACAAACAGAAGGAATATAAACTGGCTCAC

CTTCGGGTGGGCCTTTCTGC<u>TGTAGGCTGGAGCTGCTTC</u>

With a region (bold letters) homologous to the sequence 2324042-2324130 upstream of the atoB gene (sequence 2 324 131 to 2 325 315) a reference sequence on the website http://ecocvc.org/, a region (italic letters) corresponding to the transcriptional terminator T7T of the T7 phage (Harrington et al. 2001) and a region (underlined letters) for the amplification of the chloramphenicol resistance cassette of the pKD3 plasmid.

Odi 0246

(SEQ ID No 49)

TTACTGTCGCCCCCAGGTCGATGGCGCTGGTGGAAGCGAGTGAACCGTT

AAAACTACCGATAGCAGTACGTACCGCACTGACGATGACACAATTTTTC

ATT<u>TATAACCTCCTTA</u>

With a region (bold letters) homologous to the sequence 2324230-2324131 of the atoB gene (sequence 2 324 131 to 2 325 315) a reference sequence on the website http://ecocyc.org/ and a region (underlined letters) homologous to the RBS01*2 consensus sequence containing the PsiI restriction site.

The second amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the natural promoter region of the atoB gene by the ptrc01/RBS01*2-cm cassette was checked by PCR analysis using both atoBs and atoBrvoligonucleotides. The final strain was named MG1655 MG1655 ptrc30/RBS01*2-atoB-cm.

atoBs (SEQ ID No 50)

gcgcggcagcacgcagtac (homologous to the sequence 2323667 to 2323685)

atoBrv (SEQ ID No 51)

cgcacatcaggccatcgcgc (homologous to the sequence 2324584 to 2324565)

4.1.6. Construction of an E. coli MG1655ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-Ptrc01/RBS01*2-crt-hbd-TT07::FRT ptrc30/RBS01*2-atoB-::FRT modified strain The natural promoter region of the atoB gene was then replaced by the artificial ptrc01/RBS01*2 region into the MG1655ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-Ptrc01/RBS01*2-crt-hbd-TT07-FRT and the replacement was achieved by generalized P1 phage transduction from the single mutant lysate (Miller 1972).

The Cm$^R$ transductants were selected on plate and the replacement of the natural promoter region by the ptrc01/RBS01*2 artificial region into the MG1655ΔldhA::FRT ΔpflAB::FRT ΔackA-pta::FRTΔiscR::FRT ΔfrdABCD::FRTΔaceE::FRT ΔmgsA::FRTΔadhE::FRTΔmelB::TT02-Ptrc01/RBS01*2-crt-hbd-TT07-FRT was checked by PCR analysis using both atoBs and atoBrv oligonucleotides. Finally, i) hslJC and ldhAC2, ii) pFLAB1 and pflAB2 iii) B2295f and YfcCR, iv) iscr1s and iscr1rv v) frdABCD1s and frdABCD1 rv vi) aceEs and aceErv vii) mgsAs and mgsArv viii) ychGf and adhECr and ix) ome1845 and 1846rv couple of primers were also used in PCR analysis to confirm the deletion of ldhA, pflAB, ackA-pta, iscR, frdABCD, aceE, mgsA and adhE genes respectively and the crt-hbd expression in the ptrc30/RBS01*2-atoB-cm strain. The resulting strain was named MG1655 ΔldhA::FRT ΔpflAB::FRTΔackA-pta::FRTΔiscR::FRTΔfrdABCD::FRT ΔaceE::FRTΔmgsA::FRTΔadhE::FRT ΔmelB::TT02-ptrc01/RBS01*2-crt-hbd-TT07-FRT ptrc30/RBS01*2-atoB-cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 50 and 51). The new strain was named MG1655 ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-ptrc01/RBS01*2-crt-hbd-TT07-FRT ptrc30/RBS01*2-atoB-FRT.

4.2. Construction of pSC101_pGI-cac2229-cac0764-cac0303_pthl-cap0035-cac2711-cac2710-cac2709 Expression Vector:

Four CA_P0035, CA_C2711, CA_C2710, CA_C2701 synthetic genes encoding the bifunctionnal butyraldehyde and butanol dehydrogenase NADH dependent AdhE2, the butyrylCoA dehydrogenase, the electron transfer flavoproteins B and A respectively, from *Clostridium acetobutylicum* were firstly designed using the method termed codon harmonization (Angov et al. 2008). Synonymous codons from *E. coli* that match as closely as possible the codon usage frequency used in the native genes from *C. acetobutylicum* were selected. Based on the generated sequences, the synthetic genes were further synthetized by Life Technologies (ThermoFisher Scientific, Saint aubin, France) introducing the RBS region along with each gene, as well as placing two unique restriction sites upstream and downstream each gene. The CA_C2711, CA_C2710 and CA_C2701 were synthesized as an operon and the adhE2 was synthesized independently.The synthetic adhE2 gene was firstly inserted into the pSOS95 plasmid (Genbank accession number AY187686.1) between the BamHI site located downstream the thl promoter and the SfoI site, located upstream the adc terminator. The bcd-etfB-etfA synthetic artificial operon was then introduced into the pSOS95-adhE2 between the XhoI site located downstream the adhE2 gene and the SfoI site, located upstream the adc terminator to yield the pSOS95 adhE2-bcd-etfB-etfA plasmid. The pSOS95 adhE2-bcd-etfB-etfA plasmid was then digested with SalI and the operon containing fragment was purified on agarose gel before to be ligated to the pSC101_pGI-cac2229-cac0764-cac0303 plasmid pre-digested with SalI, yielding the 15.4 kb pSC101-pGI-cac2229-cac0764-cac0303-pthl-cap0035-cac2711-cac2710-cac2709 plasmid.

4.3. Construction of pSC101_pGI-cac2229-cac0764-cac0303-udhA_pthl-cap0035-cac2711-cac2710-cac2709 Expression Vector:

The udhA gene was amplified from the genomic DNA of *E. coli* MG1655 using primers udhA-NheIf and udhA-xma1r. The primers were designed to introduce a RBS region along with the udhA gene, as well as placing NheI and XmaI restriction sites upstream and downstream respectively:

```
udhA-NheIf: (SEQ ID No 52):
AATTGCTAGCATTATATACAAGGAGGAAACAGCTATGCCACATTCCTACG
ATTACGATG udhA-xma1r: (SEQ ID No 53)
AATTCCCGGGATAATTTTAAAACAGGCGGTTTAAACCGTTTAAC
```

The amplified PCR fragment was then subcloned into a Zero Blunt TOPO vector (Invitrogen, Saint Aubin, France) to yield the Zero Blunt TOPO-udhA plasmid and sequenced using universal primers T7P and T3P to assure that no mutations were introduced. The fragment containing the udhA gene was purified on an agarose gel after digestion of the Zero Blunt TOPO-udhA vector with NheI and XmaI. The 15.4 kb pSC101_pGI-cac2229-cac0764-cac0303_pThl-cap0035-cac2711-cac2710-cac2709 expression vector was also digested with NheI and XmaI and ligated to the NheI-XmaI digested udhA fragment, yielding the 16.8 kb pSC101_pGI-cac2229-cac0764-cac0303-udhA_pthl-cap0035-cac2711-cac2710-cac2709 vector.

4.4. Introduction of the pSC101_pGI-cac2229-cac0764-cac0303-udhA_pthl-cap0035-cac2711-cac2710-cac2709 expression vector into the *E. coli* MG1655 ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-Ptrc01/RBS01*2-crt-hbd-TT07::FRT ptrc30/RBS01*2-atoB::FRT Modified Strain.

The pSC101_pGI-cac2229-cac0764-cac0303-udhA_pthl-cap0035-cac2711-cac2710-cac2709 expression vector was used to transform the *E. coli* MG1655 ΔldhA::FRTΔpflAB::FRTΔackA-pta::FRTΔiscR::FRTΔfrdABCD::FRT ΔaceE::FRTΔmgsA::FRT ΔadhE::FRT ΔmelB::TT02-ptrc01/RBS01*2-crt-hbd-TT07::FRT ptrc30/RBS01*2-atoB::FRT modified strain by electroporation (Sambrook and Russel 2001).

The transformants were selected on LB agar plates supplemented with spectinomycin (70 µg/ml) at 37° C. Some transformants were then grown in LB liquid culture supplemented with spectinomycin (100 µg/ml) overnight at 37° C. to carry out a DNA plasmid extraction (GenElute HP plasmid miniprep kit, Sigma) and check for the presence of the pSC101_pGI-cac2229-cac0764-cac0303-udhA_pthl-cap0035-cac2711-cac2710-cac2709 plasmid. The pSC101_pGI-cac2229-cac0764-cac0303-udhA_pthl-cap0035-cac2711-cac2710-cac2709 plasmid was finally controlled by restriction profile.

The final *E. coli* MG1655 ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-ptrc01/RBS01*2-crt-hbd-TT07::FRT ptrc30/RB SO1*2-atoB::FRT (pSC101_pGI-cac2229-cac0764-cac0303-udhA_pthl-cap0035-cac2711-cac2710-cac2709) was grown in LB liquid medium supplemented with spectinomycin (100 µg/ml) and kept in 20% glycerol solution at −80° C.

4.5.: Physiological Characterization of the *E. coli* MG1655 ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-ptrc01/RBS01*2-crt-hbd-TT07::FRT ptrc30/RBS01*2-atoB::FRT pSC101_PGI-cac2229-cac0764-cac0303-udhA_PThl-cap0035-cac2711-cac2710-cac2709 modified strain.

The *E. coli* MG1655 ΔldhA::FRTΔpflAB::FRTΔackA-pta::FRTΔiscR::FRTΔfrdABCD::FRT ΔaceE::FRTΔmgsA::FRTΔadhE::FRT ΔmelB::TT02-Ptrc01/RBS01*2-crt-hbd-TT07::Km ptrc30/RBS01*2-atoB::cm pSC101_pGI-cac2229-cac0764-cac0303-udhApthl-cap0035-cac2711-cac2710-cac2709 strain was grown anaerobically on a 20 g/L glucose mineral medium containing minerals salts as previously described (Meynial-salles et al. 2005) supplemented with 4 g/l of yeast extract, 5 mM nitrate and spectinomycin (100 µg/ml) and inoculated with 100 µl of a LB overnight culture. Cells were grown up at 37° C. during several days, and the pH was maintained by buffering the culture medium with MOPS. As a control, the *E.coli* MG1655 ΔldhA::FRTΔpflAB::FRTΔackApta::FRTΔiscR::FRTΔfrdABCD::FRTΔaceE::FRTΔmgsA::FRTΔa dhE::FRT ΔmelB::TT02-ptrc01/RBS01*2-crt-hbd-TT07::FRT ptrc30/RBS01*2-atoB::FRT strain was grown in the same conditions.

The comparative phenotypic analysis was performed by measuring both glucose consumption as well as the concentration of fermentation products for the culture of each strain as is shown in table 4:

| Strains | Glucose consumption (g/l) | Products yield (% g/g glucose consumed) | | | | | | | |
|---|---|---|---|---|---|---|---|---|---|
| | | Butanol | Succinate | Lactate | Butyrate | Acetate | Ethanol | Pyruvate | $CO_2$ |
| MG1655ΔldhA::FRTΔpflAB::FRTΔackApta::FRTΔiscR::FRTΔfrdABCD::FRTΔaceE:: | 2.53 | 0 | 5.30 | 0 | 10.27 | 0 | 12.25 | 62 | 16.9 |

-continued

| Strains | Glucose consumption (g/l) | Products yield (% g/g glucose consumed) | | | | | | | |
|---|---|---|---|---|---|---|---|---|---|
| | | Butanol | Succinate | Lactate | Butyrate | Acetate | Ethanol | Pyruvate | CO$_2$ |
| FRTΔmgsA::FRTΔadhE:: FR TΔmelB::TT02- Ptrc01/RBS01*2-crt-hbd- TT07ptrc30/RBS01*2-atoB MG1655ΔldhA::FRTΔpflAB:: FRTΔackApta::FRTΔiscR:: FRTΔfrdABCD::FRTΔaceE:: FRTΔmgsA::FRTΔadhE:: FRTΔmelB::TT02- Ptrc01/RBS01*2-crt-hbd- TT07ptrc30/RBS01*2-atoB pSC101_PGI-cac2229-cac0764- cac0303-udhA_pthl-cap0035- cac2711-cac2710-cac2709 | 32 | 29.54 | 0.65 | 0.4 | 4.71 | 0.46 | 2.88 | 0.37 | 7 |

As shown in table 4, the expression of the both synthetic CA_C2229-CA_C0764-CA_C0303 and CA_P0035-CA_C2711-CA_C2710-CA_C2709 operons into the MG1655ΔldhA::FRTΔpflAB::FRTΔackApta::FRTΔiscR:: FRTΔfrdABCD::FRTΔaceE::FRTΔmgsA ::FRTΔadhE:: FRTΔmelB::TT02-Ptrc01/RBS01*2-crt-hbd-TT07ptrc30/ RBS01*2-atoB E.coli strain led to the production of butanol as the main fermentation product from glucose at a yield of 0.3 g/g glucose consumed corresponding to 73% of the theoretical yield. Moreover, the expression of the both synthetic CA_C2229-CA_C0764-CA_C0303 and CA_P0035-CA_C2711-CA_C2710-CA_C2709 operons, favoured the growth which was strongly hampered in the control strain (without plasmid).

4.6: Ferredoxin NADP+ Reductase Activity Determination in the the E. coli MG1655 ΔldhA::FRTΔpflAB:: FRTΔackA-pta::FRTΔiscR::FRTΔfrdABCD::FRT ΔaceE:: FRTΔmgsA::FRTΔadhE::FRT ΔmelB::TT02-ptrc01/ RBS01*2-crt-hbd-TT07::FRT ptrc30/RBS01*2-atoB::FRT pSC101_PGI-cac2229-cac0764-cac0303-udhA_PThl- cap0035-cac2711-cac2710-cac2709 Modified Strain.

The E. coli MG1655 ΔldhA::FRTΔpflAB::FRTΔackA-pta::FRTΔiscR::FRTΔfrdABCD::FRT ΔaceE::FRTΔmgsA:: FRTΔadhE::FRT ΔmelB::TT02-Ptrc01/RBS01*2-crt-hbd-TT07::Km ptrc30/RBS01*2-atoB::cm pSC101_pGI- cac2229-cac0764-cac0303-udhA_pthl-cap0035-cac2711- cac2710-cac2709 strain was grown anaerobically on a 20 g/L glucose mineral medium containing minerals salts as previously described (Meynial-salles et al. 2005) supplemented with 4 g/l of yeast extract, 5 mM nitrate and spectinomycin (100 g/ml) and inoculated with 100 µl of a LB overnight culture. Cells were grown up at 37° C. up to an approximatively OD$_{550\ nm}$ of 2, and the pH was maintained by buffering the culture medium with MOPS. As a control, the E.coli MG1655 ΔldhA::FRTΔpflAB:: FRTΔackApta::FRTΔiscR::FRTΔfrdABCD::FRTΔaceE:: FRTΔmgsA::FRTΔa dhE::FRT ΔmelB::TT02-ptrc01/ RBS01*2-crt-hbd-TT07::FRT ptrc30/RBS01*2-atoB::FRT strain was grown in the same conditions.

Cells were transferred into anaerobic chamber, harvested, washed and 20 times concentrated in 100 mM Tris-HCl 2 mM DTT 10% glycerol (pH 7.6) buffer, frozen at −80° C. or immediately used. Cells were further broken by sonication using an ultrasonic disintegrator (vibracell 72434, Bioblock) at 4° C. in four cycles of 30 sec with 2-min intervals. Debris were removed by centrifugation at 8600 g for 10 min, 4° C. (Sigma centrifuge 2-16K) and the acellular crude extract was loaded onto a SephadexG25 column to eliminate salts and metabolites, before the ferredoxin NADP+ reductase activity determination using ferredoxin as a substrate and following the procedure already described in 1.1 (table D).

TABLE D

| Ferredoxin NADP+ reductase specific activities determined on crude extracts using ferredoxin as a substrate: | |
|---|---|
| Strains | Ferredoxin NADP+ reductase specific activity U/mg protein |
| MG1655ΔldhA::FRTΔpflAB:: FRTΔackApta::FRTΔiscR:: FRTΔfrdABCD::FRTΔaceE:: FRTΔmgsA::FRTΔadhE:: FR TΔmelB::TT02-Ptrc01/ RBS01*2-crt-hbd-TT07ptrc30/ RBS01*2-atoB | 0 |
| MG1655ΔldhA::FRTΔpflAB:: FRTΔackA-pta::FRTΔiscR:: FRTΔfrdABCD::FRTΔaceE:: FRTΔmgsA::FRTΔadhE:: FRTΔmelB::TT02-Ptrc01/ RBS01*2-crt-hbd-TT07 ptrc30/ RBS01*2-atoBpSC101_PGI- cac2229-cac0764-cac0303- udhA_pthl-cap0035-cac2711- cac2710-cac2709 | 0.11 |

As shown in table D, a ferredoxin NADP+ reductase activity is only detected into the E. coli modified strain expressing the CA_C0764 encoding gene.

Example 5

Heterologous Production of 1, 3 Propanediol from Glycerol by a New Metabolic Pathway in an E. coli Strain with an Enhanced Ferredoxin NADP Reductase Activity 5.1: construction of a E. coli MG1655ΔldhA::FRT, ΔpflAB::FRT, ΔiscR::FRT, ΔfrdABCD::FRT ΔaceE::FRT, ΔmgsA::FRT ΔadhE::FRT, ΔaldA::FRT, ΔaldB::FRT, ΔglpD::FRT, ΔglpA::FRT Modified Strain 5.1.1: Construction of a E. coli MG1655ΔldhA::FRT, ΔpflAB::FRT, ΔiscR::FRT Modified Strain:

The iscR gene was then replaced with a kanamycin resistance cassette into the MG1655 ΔldhA::FRTΔpflAB:: FRT strain and the deletion was achieved by generalized P1 phage transduction from the single mutant lysate (Miller 1972) using the MG1655ΔiscR::km strain (see 3.1.7).

The Km$^R$ transductants were selected on plate and the replacement of the iscR gene by the kanamycin cassette into the MG1655ΔdhA::FRTΔpflAB::FRT was checked by PCR analysis using both iscrs and iscr1rv oligonucleotides. Finally, i) hslJC and ldhAC2 and ii) pFLAB1 and pflAB2 couple of primers were also used in PCR analysis to confirm the deletion of ldhA and pflAB genes respectively in the strain ΔiscR::km. The resulting strain was named MG1655 ΔldhA::FRTΔpflAB::FRT ΔiscR::km.

The kanamycin-resistance cassette was then eliminated by using the Flp helper pCP20 plasmid (Cheperanov and Wagernagel 1995). Km$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 24 and 25). The new strain was named MG1655 ΔldhA::FRTΔpflAB::FRTΔiscR::FRT.

5.1.2: Construction of a E. coli MG1655ΔldhA::FRT, ΔpflAB::FRT, ΔiscR::FRT, ΔfrdABCD::FRT Modified Strain:

The frdABCD genes were then replaced with a chloramphenicol resistance cassette into the MG1655ΔldhA::FRTΔpflAB::FRTΔiscR::FRT strain and the deletion was achieved by generalized P1 phage transduction from the single mutant lysate (Miller 1972) using the MG1655ΔfrdABCD::cm E. coli strain (see 3.1.9).

The CmR transductants were selected on plate and the replacement of the frdABCD genes by the chloramphenicol cassette into the MG1655ΔldhA::FRTΔpflAB::FRTΔiscR::FRT was checked by PCR analysis using both frdABCD1s and frdABCD1 rv oligonucleotides. Finally, i) hslJC and ldhAC2, ii) pFLAB1 and pflAB2 and iii) iscr1s and iscr1rv couple of primers were also used in PCR analysis to confirm the deletion of ldhA, pflAB and iscR genes respectively, in the strain ΔfrdABCD::cm. The resulting strain was named MG1655ΔldhA::FRT ΔpflAB::FRΔiscR::FRTΔfrdABCD::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 28 and 29). The new strain was named MG1655ΔldhA::FRTΔpflAB::FRTΔiscR::FRTΔfrdABCD::FRT.

5.1.3: Construction of a E. coli MG1655ΔldhA::FRT, ΔpflAB::FRT, ΔiscR::FRT, ΔfrdABCD::FRT ΔaceE::FRT Modified Strain:

The aceE gene was then replaced with a kanamycin resistance cassette into the MG1655 ΔldhA::FRTΔpflAB::FRTΔiscR::FRTΔfrdABCD::FRT strain and the deletion was achieved by generalized P1 phage transduction from the single mutant lysate (Miller 1972) using the MG1655·aceE::km E. coli strain (see 3.1.11).

The km$^R$ transductants were selected on plate and the replacement of the aceE gene by the kanamycin cassette into the MG1655ΔldhA::FRTΔpflAB::FRTΔiscR::FRTΔfrdABCD::FRT was checked by PCR analysis using both aceEs and aceErv oligonucleotides. Finally, i) hslJC and ldhAC2, ii) pFLAB1 and pflAB2 iii) iscr1s and iscr1rv and iv) frdABCD1s and frdABCD1 rv primers were also used in PCR analysis to confirm the deletion of ldhA, pflAB, iscR and frdABCD genes respectively in the strain ΔaceE::km. The resulting strain was named MG1655 ΔldhA::FRT ΔpflAB::FRTΔiscR::FRTΔaceE::km.

The kanamycin-resistance cassette was then eliminated by using the Flp helper pCP20 plasmid (Cheperanov and Wagernagel 1995). Km$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 32 and 33). The new strain was named MG1655ΔldhA::FRTΔpflAB::FRTΔiscR::FRTΔfrdABCD::FRT ΔaceE::FRT.

5.1.4.: Construction of a E. coli MG1655ΔldhA::FRT, ΔpflAB::FRT, ΔiscR::FRT, ΔfrdABCD::FRT ΔaceE::FRT, ΔmgsA::FRT Modified Strain:

The mgsA gene was then replaced with a chloramphenicol resistance cassette into the MG1655ΔldhA::FRT ΔpflAB::FRTΔiscR::FRT ΔfrdABCD::FRTΔaceE::FRT strain and the deletion was achieved by generalized P1 phage transduction from the single mutant lysate (Miller 1972) using the MG1655ΔmgsA::cm E. coli strain (see 3.1.13).

The Cm$^R$ transductants were selected on plate and the replacement of the mgsA gene by the chloramphenicol cassette into the MG1655ΔldhA::FRTΔpflAB::FRTΔiscR ::FRTΔfrdABCD::FRTΔaceE::FRT was checked by PCR analysis using both mgsAs and mgsArv oligonucleotides. Finally, i) hslJC and ldhAC2, ii) pFLAB1 and pflAB2, iii) iscr1s and iscr1rv iv) frdABCD1s and frdABCD1 rv and v) aceEs and aceErv couple of primers were also used in PCR analysis to confirm the deletion of ldhA, pflAB, iscR, frdABCD and aceE genes respectively in the strain ΔmgsA::cm. The resulting strain was named MG1655 ΔldhA::FRTΔpflAB::FRTΔiscR::FRTΔfrdABCD::FRTΔaceE::FRTΔmgsA::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 36 and 37). The new strain was named MG1655ΔldhA::FRTΔpflAB::FRTΔiscR::FRTΔfrdABCD::FRT ΔaceE::FRTΔmgsA::FRT.

5.1.5.: Construction of a E. coli MG1655ΔldhA::FRT, ΔpflAB::FRT, ΔiscR::FRT, ΔfrdABCD::FRT ΔaceE::FRT, ΔmgsA::FRT ΔadhE::FRT Modified Strain:

The adhE gene was then replaced with a chloramphenicol resistance cassette into the MG1655ΔldhA::FRT ΔpflAB::FRTΔiscR::FRT ΔfrdABCD::FRTΔaceE::FRT ΔmgsA::FRT strain and the deletion was achieved by generalized P1 phage transduction from the single mutant lysate (Miller 1972) using the MG1655ΔadhE::cm E. coli strain (see 4.1.1).

The Cm$^R$ transductants were selected on plate and the replacement of the adhE gene by the chloramphenicol cassette into the MG1655ΔldhA::FRT ΔpflAB::FRTΔiscR::FRT ΔfrdABCD::FRTΔaceE::FRTΔmgsA::FRT was checked by PCR analysis using both ychGf and adhECr oligonucleotides. Finally, i) hslJC and ldhAC2, ii) pFLAB1 and pflAB2, iii) iscr1s and iscr1rv, iv) frdABCD1s and frdABCD1rv, v) aceEs and aceErv and vi) mgsAs and mgsArv couple of primers were also used in PCR analysis to confirm the deletion of ldhA, pflAB, iscR, frdABCD, aceE and mgsA genes respectively in the strain ΔadhE::cm.

The resulting strain was named MG1655 ΔldhA::FRT ΔpflAB::FRTΔiscR::FRTΔfrdABCD::FRT ΔaceE:: FRTΔmgsA::FRTΔadhE::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 36 and 37). The new strain was named MG1655 ΔldhA::FRTΔpflAB::FRTΔiscR::FRTΔfrdABCD::FRT ΔaceE::FRTΔmgsA::FRTΔadhE::FRT.

5.1.6.: Construction of a E. coli MG1655 ΔaldA::FRT-cm-FRT Modified Strain:

The aldA gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the aldA gene:

1-AldA D f consisting of 100 bases (SEQ ID No54)
atgtcagtacccgttcaacatcctatgtatatcgatggacagtttgttac ctggcgtggagacgcatggattgatgtggtaGTGTAGGCTGGAGCTGCTT

CG

With a region (lower-case letters) homologous to the sequence (1486256-1486336) including the aldA gene initiation codon of the aldA gene (sequence 1486256 to 1487695), a reference sequence on the website http://ecocyc.org/, and a region (upper-case letters) for the amplification of the chloramphenicol resistance cassette of the pKD3 plasmid 2-aldAD r consisting of 100 bases (SEQ ID No 55):
ttaagactgtaaataaaccacctgggtctgcagatattcatgcaagccat gtttaccatctgcgccgccaataccggatttCATATGAATATCCTCCTTA

G

With a region (lower-case letters) homologous to the sequence (1487615-1487695) corresponding to the C terminal part encoding sequence of the including the stop codon aldA gene (1486256 to 1487695), a reference sequence on the website http://ecocyc.org/, and a region (upper-case letters) for the amplification of the chloramphenicol resistance cassette carried by the pKD3 plasmid. Both oligonucleotides AldADr and aldADf were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the aldA gene by the chloramphenicol cassette was checked by PCR analysis using both Ydc F C f and gapCCr oligonucleotides.

3. Ydc F C f (SEQ ID NO 56):
tgcagcggcgcacgatggcgacgttccgccg (homologous to the sequence 1485722 to 1485752)

4. gapCCr (SEQ ID NO 57):
cacgatgacgaccattcatgcctatactggc (homologous to the sequence 1488195 to 1488225)

5.1.7.: Construction of a E. coli MG1655ΔldhA::FRT, ΔpflAB::FRT, ΔiscR::FRT, ΔfrdABCD::FRT ΔaceE::FRT, ΔmgsA::FRT ΔadhE::FRTΔaldA::FRT Modified Strain:

The aldA gene was then replaced with a chloramphenicol resistance cassette into the MG1655ΔldhA::FRT ΔpflAB::FRTΔiscR::FRT ΔfrdABCD::FRTΔaceE::FRT ΔmgsA::FRT·adhE::FRT strain and the deletion was achieved by generalized P1 phage transduction from the single mutant lysate (Miller 1972).

The Cm$^R$ transductants were selected on plate and the replacement of the adhE gene by the chloramphenicol cassette into the MG1655ΔldhA::FRT ΔpflAB::FRTΔiscR:: FRT ΔfrdABCD::FRTΔaceE::FRTΔmgsA::FRTΔadhE:: FRT was checked by PCR analysis using both Ydc F C f and gapCCr oligonucleotides. Finally, i) hslJC and ldhAC2, ii) pFLAB1 and pflAB2, iii) iscr1s and iscr1rv, iv) frdABCD1s and frdABCD1rv, v) aceEs and aceErv vi) mgsAs and mgsArv and vii) ychGf and adhECr couple of primers were also used in PCR analysis to confirm the deletion of ldhA, pflAB, iscR, frdABCD, aceE, mgsA and adhE genes respectively in the strain ΔaldA::cm. The resulting strain was named MG1655 ΔldhA::FRT ΔpflAB::FRTΔiscR:: FRTΔfrdABCD::FRTΔaceE::FRTΔmgsA::FRTΔadhE:: FRTΔald A::cm.

The chloramphenicol-resistance cassette was then eliminated by using the Flp helper pCP20 plasmid (Cheperanov and and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 56 and 57). The new strain was named MG1655 ΔldhA::FRTΔpflAB::FRTΔiscR::FRTΔfrdABCD:: FRTΔaceE::FRTΔmgsA::FRTΔadhE::FRTΔaldA ::FRT 5.1.8.: Construction of a E. coli MG1655 ΔaldB::FRT-cm-FRT Modified Strain:

The aldB gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the aldB gene:

1-AldB D f consisting of 100 bases (SEQ ID No 58)
tcagaacagccccaacggtttatccgagtagctcaccagcaggcacttgg tttgctggtaatgaccagcatcatcttgtGTGTAGGCTGGAGCTGCTTCG With a region (lower-case letters) homologous to the sequence (3752996 to 3753075) of the aldB gene (sequence 3752996 á 3754534), a reference sequence on the website http://ecocyc.org/, and a region (upper-case letters) for the amplification of the chloramphenicol resistance cassette of the pKD3 plasmid 2-AldBD r consisting of 100 bases (SEQ ID No 59):
atgaccaataatccccttcagcacagattaagcccggcgagtatggttt cccctcaagttaaaagcccgctatgacaaCATATGAATATCCTCCTTAG With a region (lower-case letters) homologous to the sequence (3754455 to 3754534) of the aldB gene (sequence 3752996 á 3754534), a reference sequence on the website http://ecocyc.org/, and a region (upper-case letters) for the amplification of the chloramphenicol resistance cassette of the pKD3 plasmid.

Both oligonucleotides AldBDr and aldBDf were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the aldB gene by the chloramphenicol cassette was checked by PCR analysis using both aldBCf et YiaYCr oligonucleotides.

3-aldB C f (SEQ ID NO 60):
catatttccacaaagaatataaaaaagaacaattaacgc (homologous to the sequence 3752449 to 3752488)

4-YiaYCr (SEQ ID NO 61):
tatgttcatgcgatggcgcaccagagggcg (homologous to the sequence 3755040 to 3755070)

5.1.9.: Construction of a E. coli MG1655ΔldhA::FRT, ΔpflAB::FRT, ΔiscR::FRT, ΔfrdABCD::FRT ΔaceE::FRT ΔmgsA::FRT ΔadhE::FRTΔaldA::FRTΔaldB::FRT Modified Strain:

The aldB gene was then replaced with a chloramphenicol resistance cassette into the MG1655ΔldhA::FRT ΔpflAB::FRTΔiscR::FRT ΔfrdABCD::FRTΔaceE::FRT ΔmgsA::FRT ΔadhE::FRT ΔaldA::FRT strain and the deletion was achieved by generalized P1 phage transduction from the single mutant lysate (Miller 1972).

The Cm$^R$ transductants were selected on plate and the replacement of the adhE gene by the chloramphenicol cassette into the MG1655ΔldhA::FRT ΔpflAB::FRTΔiscR:: FRT ΔfrdABCD::FRTΔaceE::FRTΔmgsA::FRTΔadhE:: FRTΔaldA::FRT was checked by PCR analysis using both aldBCf and YiaYCr oligonucleotides. Finally, i) hslJC and ldhAC2, ii) pFLAB1 and pflAB2, iii) iscr1s and iscr1rv, iv) frdABCD1s and frdABCD1rv, v) aceEs and aceErv vi) mgsAs and mgsArv vii) ychGf and adhECr and viii)Ydc F C f and gapCCr couple of primers were also used in PCR analysis to confirm the deletion of ldhA, pflAB, iscR, frdABCD, aceE, mgsA adhE and aldA genes respectively in the strain AaldB::cm. The resulting strain was named MG1655 ΔldhA::FRT ΔpflAB::FRTΔiscR:: FRTΔfrdABCD::FRTΔaceE::FRTΔmgsA::FRTΔadhE:: FRTΔald A::FRTΔaldB::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 60 and 61). The new strain was named MG1655 ΔldhA::FRTΔpflAB::FRTΔiscR::FRTΔfrdABCD:: FRTΔaceE::FRTΔmgsA::FRTΔadhE::FRTΔ aldA ::FRTΔaldB::FRT.

5.1.6.: Construction of a MG1655 ΔglpD::FRT-cm-FRT E. coli Modified Strain:

The glpD gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the glpD gene:

1-DglpD f consisting of 100 bases (SEQ ID No 62):
atggaaaccaaagatctgattgtgatagggggcggcatcaatggtgctgg tatcgcggcagacgccgctggacgcggtttCATATGAATATCCTCCTTAG With a region (lower-case letters) homologous to the sequence (3560036-3560115) including the glpD gene initiation codon of the glpD gene (sequence 3560036 to 3561541), a reference sequence on the website http://ecocyc.org/, and a region (upper-case letters) for the amplification of the chloramphenicol resistance cassette of the pKD3 plasmid 2-DglpD r consisting of 100 bases (SEQ ID No 63):
ttacgacgccagcgataacctctgctgcgtatactccaccagccactgac tcacacgagattgttgatccgcatttagccTGTAGGCTGGAGCTGCTTCG With a region (lower-case letters) homologous to the sequence (3561462-3561541) corresponding to the C terminal part encoding sequence of the including the stop codon glpD gene (3560036 to 3561541), a reference sequence on the website http://ecocyc.org/, and a region (upper-case letters) for the amplification of the chloramphenicol resistance cassette carried by the pKD3 plasmid.

Both oligonucleotides DglpDr and DglpDf were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the glpD gene by the chloramphenicol cassette was checked by PCR analysis using both glpDCf and glpDCr oligonucleotides.

3-glpDC f (SEQ ID No 64):
cgttaatacattcgaactgatcc (homologous to the sequence 3559822 to 3559844)

4-glpDCr (SEQ ID No 65):
gcgtgggctttgcggtaattcc (homologous to the sequence 3561750 to 3561772)

5.1.7: construction of a E. coli MG1655ΔldhA::FRT, ΔpflAB::FRT, ΔiscR::FRT, ΔfrdABCD::FRTΔaceE::FRT, ΔmgsA::FRTΔadhE::FRTΔaldA::FRTΔaldB::FRTΔglpD:: FRT E. coli Modified Strain:

The glpD gene was then replaced with a chloramphenicol resistance cassette into the MG1655ΔldhA::FRT ΔpflAB:: FRTΔiscR::FRT ΔfrdABCD::FRTΔaceE::FRT ΔmgsA::FRT ΔadhE::FRT ΔaldA::FRTΔaldB::FRT strain and the deletion was achieved by generalized P1 phage transduction from the single mutant lysate (Miller 1972).

The $Cm^R$ transductants were selected on plate and the replacement of the glpD gene by the chloramphenicol cassette into the MG1655ΔldhA::FRT ΔpflAB::FRTΔiscR::FRT ΔfrdABCD::FRTΔaceE::FRTΔmgsA::FRTΔadhE::FRTΔaldA::FRTΔaldB::FRT was checked by PCR analysis using both glpDCf and glpDCr oligonucleotides. Finally, i) hslJC and ldhAC2, ii) pFLAB1 and pflAB2, iii) iscr1s and iscr1rv, iv) frdABCD1s and frdABCD1rv, v) aceEs and aceErv vi) mgsAs and mgsArv vii) ychGf and adhECr viii)Ydc F C f and gapCCr and ix) aldBCf and YiaYCr couple of primers were also used in PCR analysis to confirm the deletion of ldhA, pflAB, iscR, frdABCD, aceE, mgsA, adhE, aldA, aldB, genes respectively in the strain AglpD::cm. The resulting strain was named MG1655 ΔldhA::FRT ΔpflAB::FRTΔiscR::FRTΔfrdABCD::FRTΔaceE::FRTΔmgsA::FRTΔadhE::FRTΔald A::FRTΔaldB::FRTΔglpD::cm.

The chloramphenicol-resistance cassette was then eliminated by using the Flp helper pCP20 plasmid (Cheperanov and Wagernagel 1995). $Cm^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 64 and 65). The new strain was named MG1655 ΔldhA::FRTΔpflAB::FRTΔiscR::FRTΔfrdABCD::FRT ΔaceE::FRTΔmgsA::FRTΔadhE::FRTΔaldA::FRTΔaldB::FRTΔglpD::FRT.

5.1.8.: Construction of a E. coli MG1655 ΔglpA::FRT-cm-FRT Modified Strain:

The glpA gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the glpA gene:

```
D1
1-DglpA f consisting of 100 bases (SEQ ID No 66):
atgaaaactcgcgactcgcaatcaagtgacgtgattatcattggcggcgg cgcaacgggagccgggattgcccgcgactgCATATGAATATCCTCCTTAG
```

With a region (lower-case letters) homologous to the sequence (2350669-2350748) including the glpA gene initiation codon of the glpA gene (sequence 2350669 to 2352297), a reference sequence on the website http://ecocyc.org/, and a region (upper-case letters) for the amplification of the chloramphenicol resistance cassette of the pKD3 plasmid

```
2-DglpA r consisting of 100 bases (SEQ ID No 67):
tcaaagcgcatattctgctccttaccagaccacacaatccctgataaacc cagcgggtaaattcgctttcgcgcaGTGTAGGCTGGAGCTGCTTCG
```

With a region (lower-case letters) homologous to the sequence (2352297-2352220) corresponding to the C terminal part encoding sequence of the including the stop codon of glpA gene (2350669 to 2352297), a reference sequence on the website http://ecocyc.org/, and a region (upper-case letters) for the amplification of the chloramphenicol resistance cassette carried by the pKD3 plasmid.

Both oligonucleotides DglpAr and DglpAf were used to amplify the chloramphenicol resistance cassette from the pKD3 plasmid. The amplified PCR fragment was then introduced by electroporation into the MG1655 E. coli strain carrying the RED plasmid helper (pKD46) expressing the system α, β and exo genes encoding Gam, Bet and Exo recombinases to promote homologous recombination. The antibiotic-resistant transformants were then selected and the replacement of the glpA gene by the chloramphenicol cassette was checked by PCR analysis using both glpACf and glpACr oligonucleotides.

```
3-glpAC f (SEQ ID No 68):
ttagcctccgttgcgttcttgc (homologous to the sequence 2349038 to 2349052)

4-glpACr (SEQ ID No 69):
gccgcccataatgacagtatcaaagcgc (homologous to the sequence 2352316 to 3352289)
```

5.1.9: Construction of an E. coli MG1655ΔldhA::FRT, ΔpflAB::FRT, ΔiscR::FRT, ΔfrdABCD::FRTΔace::FRT, ΔmgsA::FRTΔadhE::FRTΔaldA::FRTΔaldB::FRTΔglpD::FRT ΔglpA::FRT Modified Strain:

The glpA gene was then replaced with a chloramphenicol resistance cassette into the MG1655ΔldhA::FRT ΔpflAB::FRTΔiscR::FRT ΔfrdABCD::FRTΔaceE::FRT ΔmgsA::FRT ΔadhE::FRT ΔaldA::FRTΔaldB::FRTΔglpD::FRT strain and the deletion was achieved by generalized P1 phage transduction from the single mutant lysate (Miller 1972).

The $Cm^R$ transductants were selected on plate and the replacement of the glpA gene by the chloramphenicol cassette into the MG1655ΔldhA::FRT ΔpflAB::FRTΔiscR::FRT ΔfrdABCD::FRTΔaceE::FRTΔmgsA::FRTΔadhE::FRTΔaldA::FRTΔaldB::FRTΔglpD::FRT was checked by PCR analysis using both glpACf and glpACr oligonucleotides. Finally, i) hslJC and ldhAC2, ii) pFLAB1 and pflAB2, iii) iscr1s and iscr1rv, iv) frdABCD1s and frdABCD1rv, v) aceEs and aceErv vi) mgsAs and mgsArv vii) ychGf and adhECr viii)Ydc F C f and gapCCr ix) aldBCf and YiaYCr and x) glpDCf and glpDCr couple of primers were also used in PCR analysis to confirm the deletion of ldhA, pflAB, iscR, frdABCD, aceE, mgsA, adhE, aldA, aldB, glpD genes respectively in the strain AglpA::cm. The resulting strain was named MG1655 ΔldhA::FRT ΔpflAB::FRTΔiscR::FRTΔfrdABCD::FRTΔaceE::FRTΔmgsA::FRTΔadhE::FRTΔald A::FRTΔaldB::FRTΔglpD::FRTΔglpA::cm.

The chloramphenicol-resistance cassette was then eliminated by using the Flp helper pCP20 plasmid (Cheperanov and Wagernagel 1995). $Cm^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 68 and 69). The new strain was named MG1655 ΔldhA::FRTΔpflAB::FRTΔiscR::FRTΔfrdABCD::FRT ΔaceE::FRTΔmgsA::FRTΔadhE::FRTΔaldA::FRTΔaldB::FRTΔglpD::FRTΔglpA::FRT.

5.2. Construction of the pSC101-pGI-cac2229-cac0764-cac0303-pntAB Expression Vector The pntAB genes were amplified from the genomic DNA of E. coli MG1655 using primers pntA-NheIf and pntB-xmaIr. The primers were designed to introduce a RBS region along with the pntA gene, as well as placing NheI and XmaI restriction sites upstream pntA and downstream pntB respectively:

```
pntAA-NheIf: (SEQ ID No 70):
AATTGCTAGCATTATATACAAGGAGGAAACAGCTatgcgaattggcatac-
caagagaacg
g pntB-xma1r: (SEQ ID No 71)
AATTCCCGGGATAATTttacagagctttcaggattgc
```

The amplified PCR fragment was then subcloned into a Zero Blunt TOPO vector (Invitrogen, Saint Aubin, France) to yield the Zero Blunt TOPO-pntAB plasmid and sequenced using universal primers T7P and T3P to assure that no mutations were introduced. The fragment containing the pntAB genes was purified on an agarose gel after digestion of the Zero Blunt TOPO-pntAB vector with NheI and XmaI. The 9.54 kb pSC101_pGI-cac2229-cac0764-cac0303 expression vector (3.2) was also digested with NheI and XmaI and ligated to the NheI-XmaI digested pntAB fragment, yielding the 12.5 kb pSC101_pGI-cac2229-cac0764-cac0303-pntAB vector.

5.3. Construction of the pSC101-pGI-cac2229-cac0764-cac0303-pntAB_pthl-dhaB1-dhaB2-yqhD Expression Vector Both dhAB1 and dhAB2 genes were amplified from the pSPD5 plasmid (Meynial-Salles et al. 2005) using primers pdhaB1 and pdhaB2. The primers were designed to introduce a RBS region along with the dhaB1 gene, as well as placing BamHI and XhoI restriction sites upstream dhAB1 and downstream dhAB2 respectively:

```
pdhaB1f: BamHI-RBS dhaB1 (SEQ ID No 72)
ggatccgtgattggaggagtaaaaatgataagtaaagg pdhaB2r:XhoI-dhaB2 (SEQ ID No 73)
CTCGAGttactcagctccaattgtgcacggtattcccat
```

The amplified PCR fragment was then subcloned into a Zero Blunt TOPO vector (Invitrogen, Saint Aubin, France) to yield the Zero Blunt TOPO—dhaB1-dhaB2 plasmid and sequenced using universal primers T7P and T3P to assure that no mutations were introduced. The fragment containing the dhaB1-dhaB2 genes was purified on an agarose gel after digestion of the Zero Blunt TOPO—dhaB1-dha2 vector with BamHI and XhoI.

The yqhD gene was amplified from genomic DNA of *E. coli* MG1655 using primers pyqhD1 and pyqhD2. The primers were designed to introduce the RBS01 region along with the yqhD gene, as well as placing XhoI and SfoI restriction sites upstream and downstream respectively:

```
pyqhD1: XhoI RBS01 yqhD (SEQ ID No 74)
CTCGAGttataacctccttaatgaacaactttaatctgcacaccccaacc cgcattct pyqhD2: SfoI-yqhDrv (SEQ ID No75)
GGCGCCttagcgggcggcttcgtatatacggcggctgacat
```

The amplified PCR fragment was then subcloned into a Zero Blunt TOPO vector (Invitrogen, Saint Aubin, France) to yield the Zero Blunt TOPO-yqhD plasmid and sequenced using universal primers T7P and T3P to assure that no mutations were introduced. The fragment containing the yqhD gene was purified on an agarose gel after digestion of the Zero Blunt TOPO-yqhD vector with XhoI and SfoI.

The 7 kb pSOS95 plasmid (Genbank accession number AY187686.1) was digested with BamHI (located downstream the thl promoter) and SfoI (located upstream the adc terminator) and ligated to both the BamHI-XhoI dhaB1 dhaB2 and XhoI-SfoI yqhD fragments to yield the pSOS95 pthl-dhaB1-dhaB2-yqhD plasmid. The pSOS95 pthl-dhaB1-dhaB2-yqhD plasmid was then digested with SalI and the operon containing fragment was purified on agarose gel before to be ligated to the pSC101_pGI-cac2229-cac0764-cac0303-pntAB plasmid pre-digested with SalI (5.2.), yielding the pSC101-pGI-cac2229-cac0764-cac0303-pntAB-pthl-dhaB1-dhaB2-yqhD plasmid.

5.4. Introduction of the pSC101-pGI-cac2229-cac0764-cac0303-pntAB_pthl-dhaB1-dhaB2-yqhD expression vector into the MG1655 ΔldhA::FRTΔpflAB::FRTΔiscR::FRTΔfrdABCD::FRT ΔaceE::FRTΔmgsA::FRTΔaceE::FRTΔmgsA::FRTΔadhE::FRTΔaldA::FRTΔaldB::FRTΔglpD:: FRTΔglpA::FRT.

The pSC101-pGI-cac2229-cac0764-cac0303-pntAB_pthl-dhaB1-dhaB2-yqhD expression vector was used to transform the MG1655 ΔldhA::FRTΔpflAB::FRTΔiscR::FRTΔfrdABCD::FRT ΔaceE::FRTΔmgsA::FRTΔaceE::FRTΔmgsA::FRTΔadhE::FRTΔaldA::FRTΔaldB::FRTΔglpD::F RTΔglpA::FRT by electroporation (Sambrook and Russel 2001).

The transformants were selected on LB agar plates supplemented with spectinomycin (70 μg/ml) at 37° C. Some transformants were then grown in LB liquid culture supplemented with spectinomycin (100 μg/ml) overnight at 37° C. to carry out a DNA plasmid extraction (GenElute HP plasmid miniprep kit, Sigma) and check for the presence of the plasmid. The pSC101-pGI-cac2229-cac0764-cac0303-pntAB_pthl-dhaB1-dhaB2-yqhD plasmid was finally controlled by restriction.

The final *E. coli* MG1655 ΔldhA::FRTΔpflAB::FRTΔackA-pta::FRTΔiscR::FRTΔfrdABCD::FRT ΔaceE::FRTΔmgsA::FRTΔadhE::FRTΔaldA::FRTΔaldB::FRTΔglpD::FRTΔglpA::FRT. pSC101-pGI-cac2229-cac0764-cac0303-pntAB_pthl-dhaB1-dhaB2-yqhD was grown in LB liquid medium supplemented with spectinomycin (100 g/ml) and kept in 20% glycerol solution at −80° C.

5.5. Physiological Characterization of the *E. coli* MG1655 ΔldhA::FRTΔpflAB::FRTΔackApta::FRTΔiscR::FRTΔfrdABCD::FRTΔaceE::FRTΔmgsA::FR T ΔadhE::FRTΔaldA::FRTΔaldB::FRTΔglpD::FRTΔglpA::FRTpSC101-pGI-cac2229-cac0764-cac0303-pntAB_pthl-dhaB1-dhaB2-yqhD modified strain.

The *E. coli* MG1655 ΔldhA::FRTΔpflAB::FRTΔackA-pta::FRTΔiscR::FRTΔfrdABCD::FRTΔaceE::FRTΔmgsA::FRTΔadhE::FRTΔaldA::FRTΔaldB::F RTΔglpD::FRTΔglpA::FRT pSC101-pGI-cac2229-cac0764-cac0303-pntAB_pthl-dhaB1-dhaB2-yqhD strain was grown anaerobically on a 20 g/L glycerol mineral medium containing minerals salts as previously described (Meynial-salles et al. 2005) supplemented with 4 g/l of yeast extract, 5 mM sodium nitrate and spectinomycin (100 μg/ml) and inoculated with 100 μl of a LB overnight culture. Cells were grown up at 37° C. during several days, and the pH was maintained by buffering the culture medium with MOPS. As a control, the *E. coli* MG1655ΔldhA::FRTΔpflAB::FRTΔackApta::FRTΔiscR::FRTΔfrdABCD::FRTΔaceE::FRTΔmgsA ::FRTΔadhE::FRTΔaldA::FRTΔaldB::FRTΔglpD::FRTΔglpA::FRT strain was grown in the same conditions.

The comparative phenotypic analysis was performed by measuring both glycerol consumption as well as the concentration of fermentation products for the culture of each strain as is shown in table 5:

| Strains | Glycerol consumption (g/l) | Concentration (g/L) | |
|---|---|---|---|
| | | 1.3 propanediol | Acetate |
| E. coli MG1655ΔldhA::FRTΔpflAB::FRTΔackApta::FRTΔiscR::FRTΔfrdABCD::FRTΔaceE::FRTΔmgsA::FRTΔadhE::FRTΔaldA::FRTΔaldB::FRTΔglpD::FRTΔglpA::FRT | 1.2 | 0 | 0.1 |
| E.coli MG1655ΔldhA::FRTΔpflAB::FRTΔackApta::FRTΔiscR::FRTΔfrdABCD::FRTΔaceE::FRTΔmgsA::FRTΔadhE::FRTΔaldA::FRTΔaldB::FRTΔglpD::FRTΔglpA::FRT pSC101-pGI-cac2229-cac0764-cac0303-pntAB pthl-dhaB1-dhaB2-yqhD | 23 | 13.8 | 3.9 |

As shown in table 5, the expression of the both CA_C2229-CA_C0764-CA_C0303-pntAB and dhaB1-dhaB2-yqhD operons into the MG1655 ΔldhA::FRTΔpflAB::FRTΔackA-pta::FRTΔiscR::FRTΔfrdABCD::FRTΔaceE::FRTΔmgsA::FRTΔadhE::FRTΔaldA::FRTΔaldB:F RTΔglpD::FRTΔglpA::FRT E.coli led to the production of 1.3 propanediol and acetate as the main fermentation products from glycerol. Moreover, the expression of both CA_C2229-CA_C0764-CA_C0303-pntAB and dhaB1-dhaB2-yqhD operons favoured the growth which was strongly hampered in the control strain.

Example 6

Heterologous Production of 1, 2 Propanediol by a New Metabolic Pathway in an *E. coli* Strain with an Enhanced Ferredoxin NADP Reductase Activity 6.1: Construction of a *E. coli* MG1655ΔldhA::FRT, ΔpflAB::FRT, ΔiscR::FRT, ΔfrdABCD::FRT ΔaceE::FRT, ΔtpiA::FRT ΔadhE::FRT, ΔaldA::FRT, ΔaldB::FRT, ΔgloA::FRT, ΔhchA::FRT Modified Strain 6.1.1. Construction of an *E. coli* MG1655ΔtpiA::cm Modified Strain:

The tpiA gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the tpiA gene:

```
DtpiAr consisting 100 bases (SEQ ID No 76):
atgcgacatcctttagtgatgggtaactggaaactgaacggcagccgcca catggttcacgagctggtttctaacctgcgtaCATATGAATATCCTCCTT
AG
```

With a region (lower-case letters) homologous to the sequence (4109530-4109449) including the tpiA gene initiation codon of the tpiA gene (sequence 4108763 to 4109530), a reference sequence on the website http://ecocyc.org/, and a region (upper-case letters) for the amplification of the chloramphenicol resistance cassette of the pKD3 plasmid

```
DtpiAf consisting of 100 bases (SEQ ID No 77):
Cttaagcctgtttagccgcttctgcagctttaacgattactgcgaaggcg tcagctttcagagaagcaccaccaaccagcTGTAGGCTGGAGCTGCTTCG
```

With a region (lower-case letters) homologous to the sequence (4108762-4108841) corresponding to the C terminal part encoding sequence of the including the stop codon tpiA gene (4108763 to 4109530), a reference sequence on the website http:ilecocyc.org/, and a region (upper-case letters) for the amplification of the chloramphenicol resistance cassette carried by the pKD3 plasmid.

Both DtpiAr and DtpiAf oligonucleotides were used to amplify the chloramphenicol resistance cassette from the pKD3 plasmid. The amplified PCR fragment was then introduced by electroporation into the MG1655 *E. coli* strain carrying the RED plasmid helper (pKD46) expressing the system α, β and exo genes encoding Gam, Bet and Exo recombinases to promote homologous recombination. The antibiotic-resistant transformants were then selected and the replacement of the tpiA gene by the chloramphenicol cassette was checked by PCR analysis using both cdh and YIIQ oligonucleotides.

```
cdh (SEQ ID No 78):
ggtgatgatagttatcgccg (homologous to the sequence 4107979 to 4107998)

YIIQ (SEQ ID No79):
cgtgccatcgacagcagtcc (homologous to the sequence 4110023 to 4110042)
```

6.1.2. Construction of a *E. coli* MG1655ΔldhA::FRT, ΔpflAB::FRT, ΔiscR::FRT, ΔfrdABCD::FRT ΔaceE::FRT, ΔtpiA::FRT Modified Strain:

The tpiA gene was then replaced with a chloramphenicol resistance cassette into the MG1655ΔldhA::FRT ΔpflAB::FRTΔiscR::FRTΔfrdABCD::FRTΔaceE::FRT strain (see 5.1.3) and the deletion was achieved by generalized P1 phage transduction from the single mutant lysate (Miller 1972) using the MG1655ΔtpiA::cm *E. coli* strain.

The Cm$^R$ transductants were selected on plate and the replacement of the tpiA gene by the chloramphenicol cassette into the MG1655ΔldhA::FRTΔpflAB::FRTΔiscR::FRTΔfrdABCD::FRTΔaceE::FRT was checked by PCR analysis using both cdh and YIIQ oligonucleotides. Finally, i) hslJC and ldhAC2, ii) pFLAB1 and pflAB2, iii) iscr1s and iscr1rviv) frdABCD1s and frdABCD1 rv and v) aceEs and aceErv couple of primers were also used in PCR analysis to confirm the deletion of ldhA, pflAB, iscR, frdABCD and aceE genes respectively in the strain ΔtpiA::cm. The resulting strain was named MG1655 ΔldhA::FRTΔpflAB::FRTΔiscR::FRTΔfrdABCD::FRTΔaceE::FRTΔtpiA::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 78 and 79). The new strain was named MG1655ΔldhA::FRTΔpflAB::FRTβiscR::FRTβfrdABCD::FRTΔaceE::FRTΔtpiA::FRT.

6.1.3. Construction of a *E. coli* MG1655ΔldhA::FRT, ΔpflAB::FRT, ΔiscR::FRT, ΔfrdABCD::FRT ΔaceE::FRT, ΔtpiA::FRTΔadhE::FRT Modified Strain:

The adhE gene was then replaced with a chloramphenicol resistance cassette into the MG1655ΔldhA::FRT ΔpflAB::FRTΔiscR::FRTΔfrdABCD::FRTΔaceE::FRTΔtpiA::FRT strain and the deletion was achieved by generalized P1 phage transduction from the single mutant lysate (Miller 1972) using the MG1655ΔadhE::cm *E. coli* strain (see 4.1.1).

The Cm$^R$ transductants were selected on plate and the replacement of the adhE gene by the chloramphenicol cassette into the MG1655ΔldhA::FRTΔpflAB::FRTΔiscR ::FRTΔfrdABCD::FRTΔaceE::FRTΔTpiA::FRT was checked by PCR analysis using both ychGf and adhECr oligonucleotides. Finally, i) hslJC and ldhAC2, ii) pFLAB1 and pflAB2, iii) iscr1s and iscr1rv iv) frdABCD1s and frdABCD1rv v) aceEs and aceErv and vi) cdh and YIIQ couple of primers were also used in PCR analysis to confirm the deletion of ldhA, pflAB, iscR, frdABCD, aceE and tpiA genes respectively in the strain ΔadhE::cm. The resulting strain was named MG1655 ΔldhA::FRTΔpflAB::FRTΔiscR::FRTΔfrdABCD::FRTΔaceE::FRTΔtpiA::FRTΔadhE::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 40 and No 41). The new strain was named MG1655ΔldhA::FRTΔpflAB::FRTΔiscR::FRTΔfrdABCD::FRTΔaceE::FRTΔtpiA::FRT ΔadhE::FRT.

6.1.4. Construction of an *E. coli* MG1655ΔldhA::FRT, ΔpflAB::FRT, ΔiscR::FRT, ΔfrdABCD::FRT ΔaceE::FRT, ΔtpiA::FRTΔadhE::FRT ΔaldA::FRT Modified Strain:

The aldA gene was then replaced with a chloramphenicol resistance cassette into the MG1655ΔldhA::FRT ΔpflAB::FRTΔiscR::FRTΔfrdABCD::FRTΔaceE::FRT ΔtpiA::FRT ΔadhE::FRT strain and the deletion was achieved by generalized P1 phage transduction from the single mutant lysate (Miller 1972) using the MG1655ΔaldA::cm *E. coli* strain (see 5.1.6).

The Cm$^R$ transductants were selected on plate and the replacement of the aldA gene by the chloramphenicol cassette into the MG1655ΔldhA::FRTΔpflAB::FRTΔiscR ::FRTΔfrdABCD::FRTΔaceE::FRTΔtpiA::FRT ΔadhE::FRT was checked by PCR analysis using both YdcFCF and gapCCr oligonucleotides. Finally, i) hslJC and ldhAC2, ii) pFLAB1 and pflAB2, iii) iscr1s and iscr1rv iv) frdABCD1s and frdABCD1 rv v) aceEs and aceErv vi) cdh and YIIQ and vii) ychGf and adhECr couple of primers were also used in PCR analysis to confirm the deletion of ldhA, pflAB, iscR, frdABCD, ace, tpiA and adhE genes respectively in the strain ΔaldA::cm. The resulting strain was named MG1655 ΔldhA::FRTΔpflAB::FRTΔiscR::FRTΔfrdABCD::FRTΔaceE::FRTΔtpiA::FRT ΔadhE::FRTΔaldA: :cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 56 and No 57). The new strain was named MG1655ΔldhA::FRTΔpflAB::FRTΔiscR::FRTΔfrdABCD::FRTΔaceE::FRTΔtpiA::FRT ΔadhE::FRTΔaldA::FRT.

6.1.5. Construction of an *E. coli* MG1655ΔldhA::FRT, ΔpflAB::FRT, ΔiscR::FRT,ΔfrdABCD::FRTΔaceE::FRT, ΔtpiA::FRTΔadhE::FRT ΔaldA::FRT ΔaldB::FRT Modified Strain:

The aldB gene was then replaced with a chloramphenicol resistance cassette into the MG1655ΔldhA::FRT ΔpflAB::FRTΔiscR::FRTΔfrdABCD::FRTΔaceE::FRTΔtpiA::FRTΔadhE::FRT ΔaldA::FRT strain and the deletion was achieved by generalized P1 phage transduction from the single mutant lysate (Miller 1972) using the MG1655ΔaldB::cm *E. coli* strain (see 5.1.8).

The Cm$^R$ transductants were selected on plate and the replacement of the aldB gene by the chloramphenicol cassette into the MG1655ΔldhA::FRTΔpflAB::FRTΔiscR ::FRTΔfrdABCD::FRTΔaceE::FRTΔtpiA::FRT ΔadhE::FRT ΔaldA::FRT was checked by PCR analysis using both aldBCf and YiaYCr oligonucleotides. Finally, i) hslJC and ldhAC2, ii) pFLAB1 and pflAB2, iii) iscr1s and iscr1rv iv) frdABCD1s and frdABCD1rv v) aceEs and aceErv vi) cdh and YIIQ, ychGf and adhECr and vii) YdcFCF and gapCCr couple of primers were also used in PCR analysis to confirm the deletion of ldhA, pflAB, iscR, frdABCD, aceE, tpiA adhE and aldA genes respectively in the strain ΔaldB::cm. The resulting strain was named MG1655 ΔldhA::FRTΔpflAB::FRTΔiscR::FRTΔfrdABCD::FRTΔaceE::FRTΔtpiA::FRT ΔadhE::FRTΔaldA: :FRTΔaldB::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 60 and No 61). The new strain was named MG1655ΔldhA::FRTΔpflAB::FRTΔiscR::FRTΔfrdABCD::FRTΔaceE::FRTΔtpiA::FRT ΔadhE::F RTΔaldA::FRTΔaldB::FRT.

6.1.6 Construction of an *E. coli* MG1655ΔgloA::FRT-cm-FRT Modified Strain:

The gloA gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

```
Two oligonucleotides were designed and used to
replacethe gloA gene:
GLOAD f consisting of 100 bases (SEQ ID No 80):
atgcgtcttcttcataccatgctgcgcgttggcgatttgcaacgctccat cgatttttataccaaagtgctgggcatgaaGTGTAGGCTGGAGCTGCTTC

G
```

With a region (lower-case letters) homologous to the sequence (1725861-1725940) including the gloA gene initiation codon of the gloA gene (sequence 1725861 to 1726026), a reference sequence on the website http://ecocyc.org/, and a region (upper-case letters) for the amplification of the chloramphenicol resistance cassette of the pKD3 plasmid GLOA D R consisting of 100 bases (SEQ ID No 81)
ttagttgcccagaccgcgaccggcgtctttctcttcgattaactcaattt tgtaaccgtccggatcttccacaaacgcgaCATATGAATATCCTCCTTAG With a region (lower-case letters) homologous to the sequence (1726189-1726268) corresponding to the C terminal part encoding sequence of the including the stop codon gloA gene (1725861 to 1726268), a reference sequence on the website http://ecocyc.org/, and a region (upper-case letters) for the amplification of the chloramphenicol resistance cassette carried by the pKD3 plasmid.

Both GLOADr and GLOADf oligonucleotides were used to amplify the chloramphenicol resistance cassette from the pKD3 plasmid. The amplified PCR fragment was then introduced by electroporation into the MG1655 *E. coli* strain carrying the RED plasmid helper (pKD46) expressing the system α, β and exo genes encoding Gam, Bet and Exo recombinases to promote homologous recombination. The antibiotic-resistant transformants were then selected and the replacement of the gloA gene by the chloramphenicol cassette was checked by PCR analysis using both NemACd and RntCr oligonucleotides.

NemACd (SEQ ID No 82):
gaagtggtcgatgccgggattgaagaatggg (homologous to the sequence 1725331 to 1725361)

Rnt Cr (SEQ ID No 83):
gggttacgtttcagtgaggcgcgttctgcgg (homologous to the sequence 1726765 to 1726795)

6.1.7 Construction of an *E. coli* MG1655ΔldhA::FRT, ΔpflAB::FRT, ΔiscR::FRT,ΔfrdABCD::FRTΔaceE::FRT, ΔtpiA::FRTΔadhE::FRT ΔaldA::FRT ΔaldB::FRT ΔgloA::FRT Modified Strain:

The gloA gene was then replaced with a chloramphenicol resistance cassette into the MG1655ΔldhA::FRT ΔpflAB::FRTΔiscR::FRTΔfrdABCD::FRTΔaceE::FRTΔtpiA::FRT ΔadhE::FRT ΔaldA::FRT ΔaldB::FRT strain and the deletion was achieved by generalized P1 phage transduction from the single mutant lysate (Miller 1972) using the MG1655ΔgloA::cm *E. coli* strain.

The Cm$^R$ transductants were selected on plate and the replacement of the gloA gene by the chloramphenicol cassette into the MG1655ΔldhA::FRTΔpflAB::FRTΔiscR::FRTΔfrdABCD::FRTΔaceE::FRTΔtpiA::FRT ΔadhE::FRT ΔaldA::FRT ΔaldB::FRT was checked by PCR analysis using both NemACd and RntCr oligonucleotides. Finally, i) hslJC and ldhAC2, ii) pFLAB1 and pflAB2, iii) iscr1s and iscr1rv iv) frdABCD1s and frdABCD1rv v) aceEs and aceErv vi) cdh and YIIQ, ychGf and adhECr vii) YdcFCF and gapCCr cand viii) aldBCf and YiaYCr couple of primers were also used in PCR analysis to confirm the deletion of ldhA, pflAB, iscR, frdABCD, aceE, tpiA, adhE, aldA and aldB genes respectively in the strain AgloA::cm. The resulting strain was named MG1655 ΔldhA::FRTΔpflAB::FRTΔiscR::FRTΔfrdABCD::FRTΔaceE::FRTΔtpiA::FRT ΔadhE::FRTΔaldA: :FRTΔaldB::FRTΔgloA::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 82 and No 83). The new strain was named MG1655ΔldhA::FRTΔpflAB::FRTΔiscR::FRTΔfrdABCD::FRTΔaceE::FRTΔtpiA::FRT ΔadhE::F RTΔaldA:: FRTΔaldB::FRTΔgloA::FRT.

6.1.8 Construction of an *E. coli* MG1655ΔgloB::FRT-cm-FRT Modified Strain:

The gloB gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the gloB gene:

GLOBD f consisting of 100 bases (SEQ ID No 84):
acaatcaggcagcgacctgcttcatcattcaaaacccagatgtaattgtc atcaaaggcgggaatactgttaagattcatGTGTAGGCTGGAGCTGCTTC

G

With a region (lower-case letters) homologous to the sequence (234703-234782) including the gloB gene initiation codon of the gloB gene (sequence 234027 to 234782), a reference sequence on the website http://ecocyc.org/, and a region (upper-case letters) for the amplification of the chloramphenicol resistance cassette of the pKD3 plasmid GLOB D R consisting of 100 bases (SEQ ID No 85)
taatgtaattaatgaagaaacattattgcaacaacctgaagagcgttttg catggttaaggtcaaagaaagataggttctgaCATATGAATATCCTCCTT

AG

With a region (lower-case letters) homologous to the sequence (234027-234108) corresponding to the C terminal part encoding sequence of the including the stop codon gloB gene (234027 to 234782), a reference sequence on the website http://ecocyc.org/, and a region (upper-case letters) for the amplification of the chloramphenicol resistance cassette carried by the pKD3 plasmid.

Both GLOBDr and GLOBDf oligonucleotides were used to amplify the chloramphenicol resistance cassette from the pKD3 plasmid. The amplified PCR fragment was then introduced by electroporation into the MG1655 *E. coli* strain carrying the RED plasmid helper (pKD46) expressing the system α, β and exo genes encoding Gam, Bet and Exo recombinases to promote homologous recombination. The antibiotic-resistant transformants were then selected and the replacement of the gloB gene by the chloramphenicol cassette was checked by PCR analysis using both MltDCfd and YafS Cr oligonucleotides.

MltDCfd (SEQ ID No 86):
ggcgagtaatatcgcttttgcc (homologous to the sequence 233929 to 233950)

YafS Cr (SEQ ID No 87):
gacagtttgagggactcttgccgg (homologous to the sequence 234822 to 234845)

6.1.9. Construction of an *E. coli* MG1655ΔldhA::FRT, ΔpflAB::FRT, ΔiscR::FRT,ΔfrdABCD::FRTΔaceE::FRT, ΔtpiA::FRTΔadhE::FRT ΔaldA::FRT ΔaldB:: FRT ΔgloA:: FRT ΔgloB::FRT Modified Strain:

The gloB gene was then replaced with a chloramphenicol resistance cassette into the MG1655ΔldhA::FRT ΔpflAB::FRTΔiscR::FRTΔfrdABCD::FRTΔaceE::FRTΔtpiA::FRT ΔadhE::FRT ΔaldA::FRT ΔaldB::FRT ΔgloA::FRT strain and the deletion was achieved by generalized P1 phage transduction from the single mutant lysate (Miller 1972) using the MG1655ΔgloB::cm *E. coli* strain.

The Cm$^R$ transductants were selected on plate and the replacement of the gloB gene by the chloramphenicol cassette into the MG1655ΔldhA::FRTΔpflAB::FRTΔiscR::FRTΔfrdABCD::FRTΔaceE::FRTΔtpiA::FRT ΔadhE::FRT ΔaldA::FRT ΔaldB::FRT ΔgloA::FRT was checked by PCR analysis using both MltDCfd and YafS Cr oligonucleotides. Finally, i) hslJC and ldhAC2, ii) pFLAB1 and pflAB2, iii) iscr1s and iscr1rv iv) frdABCD1s and frdABCD1 rv v) aceEs and aceErv vi) cdh and YIIQ, ychGf and adhECr vii) YdcFCF and gapCCr cand viii) aldBCf and YiaYCr and NemACd and RntCr couple of primers were also used in PCR analysis to confirm the deletion of ldhA, pflAB, iscR, frdABCD, aceE, tpiA, adhE, aldA, aldB and gloA genes respectively in the strain AgloB::cm. The resulting strain was named MG1655 ΔldhA::FRTΔpflAB::FRTΔiscR::FRTΔfrdABCD::FRTΔaceE::FRTΔtpiA::FRT ΔadhE::FRTΔaldA: :FRTΔaldB::FRTΔgloA::FRTΔgloB::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 86 and No 87). The new strain was named MG1655ΔldhA::FRTΔApflAB::FRTΔiscR::FRTΔfrdABCD::FRTΔaceE::FRTΔtpiA::FRT ΔadhE::FRTΔaldA::FRTΔaldB::FRTΔgloA::FRTΔgloB::FRT.

6.1.10. Construction of an *E. coli* MG1655ΔhchA::FRT-cm-FRT Modified Strain:

The hchA gene was replaced with a chloramphenicol antibiotic resistance cassette flanked by Flp recognition target (FRT) that is generated by PCR by using primers with 80-nt homology extensions deleting most of the concerned gene. The used technique was described by Datsenko and Wanner in 2000.

Two oligonucleotides were designed and used to replace the hchA gene:

```
HchAD f consisting of 100 bases (SEQ ID No 88):
atgactgttcaaacaagtaaaaatccgcaggtcgatattgctgaagataa tgcattcttcccttcagaatattcgcttagCCTTCAGAATATTCGCTTAG

GTGTAGGCTGGAGCTGCTTCG
```

With a region (lower-case letters) homologous to the sequence (2033859-2033938) including the hchA gene initiation codon of the hchA gene (sequence 2033859 to 2034710), a reference sequence on the website http://ecocyc.org/, and a region (upper-case letters) for the amplification of the chloramphenicol resistance cassette of the pKD3 plasmid

```
HchA D R consisting of 100 bases (SEQ ID No 89)
ttaacccgcgtaagctgccagcatttcctgcgccgccagtttacccaacg cattcgctgcaaaaggactgtcgccggtgaCATATGAATATCCTCCTTAG
```

With a region (lower-case letters) homologous to the sequence (2034631-2034710) corresponding to the C terminal part encoding sequence of the including the stop codon hchA gene (2033859 to 2034710), a reference sequence on the website http://ecocyc.org/, and a region (upper-case letters) for the amplification of the chloramphenicol resistance cassette carried by the pKD3 plasmid.

Both HchADr and HchADf oligonucleotides were used to amplify the chloramphenicol resistance cassette from the pKD3 plasmid. The amplified PCR fragment was then introduced by electroporation into the MG1655 *E. coli* strain carrying the RED plasmid helper (pKD46) expressing the system α, β and exo genes encoding Gam, Bet and Exo recombinases to promote homologous recombination. The antibiotic-resistant transformants were then selected and the replacement of the hchA gene by the chloramphenicol cassette was checked by PCR analysis using both YedS_3Cf and YedvCr oligonucleotides.

```
YedS_3Cf (SEQ ID No 90):
tgtgggcttagtctaccagttc (homologous to the sequence 2033243-2033264)

Yedv Cr (SEQ ID No 91):
cgttaccgcaaagaaattaa (homologous to the sequence 2034818 to 2034837)
```

6.1.11. Construction of an *E. coli* MG1655ΔldhA::FRT, ΔpflAB::FRT, ΔiscR::FRT,ΔfrdABCD::FRTΔaceE::FRT, ΔtpiA::FRTΔadhE::FRT ΔaldA::FRTΔaldB::FRTΔgloA::FRTΔgloB::FRTΔhchA::FRT Modified Strain:

The hchA gene was then replaced with a chloramphenicol resistance cassette into the MG1655ΔldhA::FRT ΔpflAB::FRTΔiscR::FRTΔfrdABCD::FRTΔaceE::FRTΔtpiA::FRT ΔadhE::FRT ΔaldA::FRT ΔaldB::FRT ΔgloA::FRT ΔgloB::FRT strain and the deletion was achieved by generalized P1 phage transduction from the single mutant lysate (Miller 1972) using the MG1655ΔhchA::cm *E. coli* strain.

The Cm$^R$ transductants were selected on plate and the replacement of the hchA gene by the chloramphenicol cassette into the MG1655ΔldhA::FRTΔpflAB::FRTΔiscR::FRTΔfrdABCD::FRTΔaceE::FRTΔtpiA::FRT ΔadhE::FRT ΔaldA::FRT ΔaldB::FRT ΔgloA::FRT ΔgloB::FRT was checked by PCR analysis using both YedS_3Cf and YedvCr oligonucleotides. Finally, i) hslJC and ldhAC2, ii) pFLAB1 and pflAB2, iii) iscr1s and iscr1rv iv) frdABCD1s and frdABCD1 rv v) aceEs and aceErv vi) cdh and YIIQ, ychGf and adhECr vii) YdcFCF and gapCCr cand viii) aldBCf and YiaYCr, NemACd and RntCr and MltDCfd and YafS Cr couple of primers were also used in PCR analysis to confirm the deletion of ldhA, pflAB, iscR, frdABCD, aceE, tpiA, adhE, aldA, aldB, gloA and gloB genes respectively in the strain ΔhchA::cm. The resulting strain was named MG1655 ΔldhA::FRTΔpflAB::FRTΔiscR::FRTΔfrdABCD::FRTΔaceE::FRTΔtpiA::FRT ΔadhE::FRTΔaldA: :FRTΔaldB::FRTΔgloA::FRTΔgloB::FRTΔhchA::cm.

The chloramphenicol-resistance cassette was then eliminated by using the Flp helper pCP20 plasmid (Cheperanov and Wagernagel 1995). Cm$^R$ mutants were transformed with pCP20, and ampicillin-resistant transformants were selected at 30° C., after which a few were colony purified at 42° C. and then tested for loss of the antibiotic resistance by PCR analysis using oligonucleotides previously described (SEQ ID No 90 and No 919). The new strain was named MG1655ΔldhA::FRTΔpflAB::FRTΔiscR::FRΔfrdABCD::

FRTΔaceE::FRTΔtpiA::FRTΔadhE::FRT ΔaldA::FRTΔaldB::FRTΔgloA::FRTΔgloB::FRTΔhchA::FRT.

6.2 Construction of the pSC101-pGI-cac2229-cac0764-cac0303pthl gldA-yqhD Expression Vector The gldA gene was amplified from genomic DNA of *E. coli* MG1655 using primers pgldA1f and pgldA2r. The primers were designed to introduce the RBS01 region along with the gldA gene, as well as placing BamHI and XhoI restriction sites upstream and downstream respectively:

```
pgldA1f: BamHI-RBS gldA (SEQ ID No 92)
GGATCCttataacctccttaatggaccgcattattcaatcaccggg pgldAr: XhoI-gldA (SEQ ID No 93)
CTCGAGttattcccactcttgcaggaaacgc
```

The amplified PCR fragment was then subcloned into a Zero Blunt TOPO vector (Invitrogen, Saint Aubin, France) to yield the Zero Blunt TOPO-gldA plasmid and sequenced using universal primers T7P and T3P to assure that no mutations were introduced. The fragment containing the dhaB1-dhaB2 genes was purified on an agarose gel after digestion of the Zero Blunt TOPO-gldA vector with BamHI and XhoI.

The pSOS95 pthl-dhaB1-dhaB2-yqhD plasmid (see 5.3) was digested with BamHI and XhoI and ligated to the BamHI-XhoI gldA fragment to yield the pSOS95 pthl-gldA-yqhD plasmid. The pSOS95 pthl-gldA-yqhD plasmid was then digested with SalI and the operon containing fragment was purified on agarose gel before to be ligated to the pSC101_pGI-cac2229-cac0764-cac0303 plasmid pre-digested with SalI (3.2.), yielding the pSC101-pGI-cac2229-cac0764-cac0303_pthl-gldA-yqhD plasmid.

6.3 Construction of the pSC101-pGI-cac2229-cac0764-cac0303-pntAB_pthl sadh$_{beij}$-yqhD Expression Vector The sadh gene from *C. beijerinckii* was amplified from the pSOS952 plasmid (Dusséaux et al. 2013) using primers psadh1 and psadh2r. The primers were designed to amplify the RBS region along with the sadh gene, as well as placing BamHI and XhoI restriction sites upstream and downstream sadh respectively:

```
psadh1f: BamHI-RBSsadh (SEQ ID No 94)
GGATCCtatatttaaggaggaacatattttatgaaaggttttgcaatgc psadh2r: XhoI-sadh (SEQ ID No 95)
CTCGAGttataatataactactgctttaattaagtcttttggc
```

The amplified PCR fragment was then subcloned into a Zero Blunt TOPO vector (Invitrogen, Saint Aubin, France) to yield the Zero Blunt TOPO-sadh plasmid and sequenced using universal primers T7P and T3P to assure that no mutations were introduced. The fragment containing the sadh gene was purified on an agarose gel after digestion of the Zero Blunt TOPO-sadh vector with BamHI and XhoI.

The pSOS95 pthl-dhaB1-dhaB2-yqhD plasmid (see 5.3) was digested with BamHI and XhoI and ligated to the BamHI-XhoI sadh fragment to yield the pSOS95 pthl-sadh-yqhD plasmid. The pSOS95 pthl-sadh-yqhD plasmid was then digested with SalI and the operon containing fragment was purified on agarose gel before to be ligated to the pSC101_pGI-cac2229-cac0764-cac0303-pntAB plasmid pre-digested with SalI (5.2.), yielding the pSC101-pGI-cac2229-cac0764-cac0303-pntAB_pthl-sadh-yqhD plasmid.

6.4. Introduction of the pSC101-pGI-cac2229-cac0764-cac0303-pntAB_pthl gldA-yqhD expression vector into the MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT *E. coli* strain:.

The pSC101-pGI-cac2229-cac0764-cac0303-pntAB_pthl gldA-yqhD expression vector was used to transform MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT *E. coli* strain by electroporation (Sambrook and Russel 2001).

The transformants were selected on LB agar plates supplemented with spectinomycin (70 µg/ml) at 37° C. Some transformants were then grown in LB liquid culture supplemented with spectinomycin (100 µg/ml) overnight at 37° C. to carry out a DNA plasmid extraction (GenElute HP plasmid miniprep kit, Sigma) and check for the presence of the plasmid. The pSC101-pGI-cac2229-cac0764-cac0303-pthlgldA-yqhD plasmid was finally controlled by restriction profile.

The final MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT pSC101-pGI-cac2229-cac0764-cac0303-pthlgldA-yqhD *E. coli* strain was grown in LB liquid medium supplemented with spectinomycin (100 µg/ml) and kept in 20% glycerol solution at −80° C.

6.5. Introduction of the pSC101-pGI-cac2229-cac0764-cac0303-pntAB_pthl sadh$_{beij}$-yqhD expression vector into the MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT *E. coli* strain:.

The pSC101-pGI-cac2229-cac0764-cac0303-pntAB_pthl sadh$_{beij}$-yqhD expression vector was used to transform MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT *E. coli* strain by electroporation (Sambrook and Russel 2001).

The transformants were selected on LB agar plates supplemented with spectinomycin (70 µg/ml) at 37° C. Some transformants were then grown in LB liquid culture supplemented with spectinomycin (100 µg/ml) overnight at 37° C. to carry out a DNA plasmid extraction (GenElute HP plasmid miniprep kit, Sigma) and check for the presence of the plasmid. The pSC101-pGI-cac2229-cac0764-cac0303-pntAB pthl-sadh$_{beij}$-yqhD plasmid was finally controlled by restriction profile.

The final MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRΔAgloA::FRTΔgloB::FRTΔhchA::FRT pSC101-pGI-cac2229-cac0764-cac0303-pntAB_pthl-sadh$_{beij}$-yqhD *E. coli* strain was grown in LB liquid medium supplemented with spectinomycin (100 µg/ml) and kept in 20% glycerol solution at −80° C.

6.6 Physiological Characterization of the *E. coli* MG1655ΔldhA::FRTΔpflAB::FRTΔiscR::FRΔfrdABCD::FRTΔaceE::FRTΔtpiA::FRTΔadhE:: FRTΔaldA::FRTΔaldB::FRTΔgloA::FRTΔgloB::FRTΔhchA::FRT pSC101-pGI-cac2229-cac0764-cac0303-pntAB_pthl-sadh$_{beij}$-yqhD and MG1655ΔldhA::FRTΔpflAB::FRTΔiscR::FRΔfrdABCD::FRTΔaceE::FRTΔtpiA:: FRTΔadhE:: FRTΔaldA::FRTΔaldB::FRTΔgloA::FRTΔgloB::FRTΔhchA::FRT pSC101-pGI-cac2229-cac0764-cac0303-pthlgldA-yqhD modified strains.

Both *E. coli* MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT (pSC101-pGI-cac2229-cac0764-cac0303-pntAB_pthl-sadh$_{beij}$-yqhD) and MG1655ΔldhA::FRTβpflAB::FRTβiscR::FR4frdABCD::FRTΔaceE::FRTΔtpiA::FRTΔadhE::FRT ΔaldA::FRTΔaldB::FRTΔgloA::FRTΔgloB::FRTΔhchA::FRT (pSC101-pGI-cac2229-cac0764-cac0303 pthlgldA-yqhD) strains were grown anaerobically on a 20 g/L glucose mineral medium containing minerals salts as previously described (Meynial-salles et al. 2005) supplemented with 4 g/l of yeast extract, 5 mM sodium nitrate and spectinomycin (100 µg/ml) and inoculated with 100 µl of a LB overnight culture. Cells were grown up at 37° C. during several days, and the pH was maintained by buffering the culture medium with MOPS. As a control, the E. coli MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT strain was grown in the same conditions.

The comparative phenotypic analysis was performed by measuring both glucose consumption as well as the concentration of fermentation products for the culture of each strain as is shown in table 6:

| Strains | Glucose consumption g/l | Concentration (g/L) | |
|---|---|---|---|
| | | 1.2 propanediol | Acetate |
| MG1655ΔldhA::FRTΔpflAB::FRTΔiscR::FRΔfrdABCD::FRTΔaceE::FRTΔtpiA::FRTΔadhE::FRTΔaldA::FRTΔaldB::FRTΔgloA::FRTΔgloB::FRTΔhchA::FRT | 2.3 | 0.2 | 0.05 |
| MG1655ΔldhA::FRTΔpflAB::FRTΔiscR::FRΔfrdABCD::FRTΔaceE::FRTΔtpiA::FRTΔadhE::FRTΔaldA::FRTΔaldB::FRTΔgloA::FRTΔgloB::FRTΔhchA::FRT pSC101-pGI-cac2229-cac0764-cac0303-pthl-sadh$_{beij}$-yqhD | 16.4 | 6.3 | 5.2 |
| MG1655ΔldhA::FRTΔpflAB::FRTΔiscR::FRΔfrdABCD::FRTΔaceE::FRTΔtpiA::FRTΔadhE::FRTΔaldA::FRTΔaldB::FRTΔgloA::FRTΔgloB::FRTΔhchA::FRT pSC101-pGI-cac2229-cac0764-cac0303_pthl-gldA-yqhD | 19.8 | 7.2 | 6.3 |

As shown in table 6, the expression of the both CA_C2229-CA_C0764-CA_C0303 and gldA-yqhD operons or both CA_C2229-CA_C0764-CA_C0303 and sadh$_{beij}$-yqhD operons into the MG1655ΔldhA::FRTΔpflAB::FRTΔiscR::FRΔfrdABCD::FRTΔaceE::FRTΔtpiA::FRTΔadhE::FRT ΔaldA::FRTΔaldB::FRTΔgloA::FRTΔgloB::FRTΔhchA::FRT E. coli strain led to the production of 1.2 propanediol and acetate as the main fermentation products from glucose. Moreover, the expression of operons, whaterever the combination is, favoured the growth which was strongly hampered in the control strain.

REFERENCES

Almeida J R, Fávaro LC, Quirino BF 2012 Biodiesel biorefinery: opportunities and challenges for microbial production of fuels and chemicals from glycerol waste. Biotechnology for biofuels, 5.48.

Altaras N E, Cameron D C 2000. Enhanced production of (R)-1,2-propanediol by metabolically engineered Escherichia coli. Biotechnol. Prog. 16: 940-946

Anderson E H 1946. Growth Requirements of Virus-Resistant Mutants of Escherichia Coli Strain "B". Proc. Natl. Acad. Sci. USA 32:120-128

Atsumi S, Cann A F, Connor M R, Shen C R, Smith K M, Brvnildsen M P, Chou K J, Hanai T, Liao J C. 2007. Metabolic engineering of Escherichia coli for 1-butanol production: Metab Eng., 10, 305-311.

Baldomà L, Aguilar J. 1988 Metabolism of L-fucose and L-rhamnose in Escherichia coli: aerobic-anaerobic regulation of L-lactaldehyde dissimilation. J Bacteriol, 170, 416-21

Bennett G N, San K Y. 2001 Microbial formation, biotechnological production and applications of 1,2-propanediol. Appl Microbiol Biotechnol., 55, 1-9.

Berezina O V, Zakharova N V, Brandt A, Yarotsky S V, Schwarz W H, Zverlov V Y. 2010. Reconstructing the clostridial n-butanol metabolic pathway in Lactobacillus brevis. Appl. Microb. Biotechnol. 87:6365-646.

Bernardi A, Bernardi F 1984. Complete sequence of pSC101. Nucleic Acids Res. 12, 9415-26.

Bond-Watts B B, Bellerose R J, Chang M C, 2011. Enzyme mechanism as a kinetic control element for designing synthetic biofuel pathways. Nat. Chem. Biol. 7: 222-227.

Bradford M M 1976. A rapid and sensitive method for the quantification of microgram quantities of protein utilizing the principle of protein-dye binding. Anal. Biochem. 72: 248-264

Cherepanov P. P., Wackernagel W. 1995. Gene disruption in Escherichia coli: Tc$^R$ and Km$^R$ cassettes with the option of Flp-catalyzed excision of the antibiotic-resistance determinant. Gene 158(1):9-14.

Cintesoli A, Clomburg J M, Rigou V., Zygourakis K., Gonzalez R. 2012 Quantitative analysis of the fermentative metabolism of glycerol in Escherichia coli, Biotech. Bioeng., 109, 187-198.

Clomburg J M, Gonzalez R 2011 Metabolic engineering of Escherichia coli for the production of 1,2-propanediol from glycerol., Biotech. Bioeng., 108, 867-879.

Cornillot E, Nair R V, Papoutsakis, Soucaille P. 1997. The genes for butanol and acetone formation in Clostridium acetobutylicum ATCC 824 reside on a large plasmid whose loss leads to degeneration of the strain. J. Bacteriol. 179:5442-7.

Datsenko K. A., Wanner B. L. 2000. One-step inactivation of chromosomal genes in Escherichia coli K-12 using PCR products. Proc Natl Acad Sci USA 97(12):6640.

Dellomonaco C, Clomburg J M, Miller E N, Gonzalez R. 2011 Engineered reversal of the β-oxidation cycle for the synthesis of fuels and chemicals, Nature. 2011 355-9.

Demuez M, Cournac L, Guerrini O, Soucaille P, Girbal L. 2007, Complete activity profile of Clostridium acetobutylicum [FeFe]-hydrogenase and kinetic parameters for endogenous redox partners: FEMS Microbiol Lett. 275, 113-21.

Dusséaux S, Croux C, Soucaille P, Meynial-Salles I. 2013. Metabolic engineering of Clostridium acetobutylicum ATCC 824 for the high-yield production of a biofuel composed of an isopropanol/butanol/ethanol mixture. Metab Eng., 18,1-8

Fontaine L, Meynial-Salles I, Yang X, Croux C and P Soucaille. 2002. Molecular characterisation and transcriptional analysis of adhE2, the gene encoding the NADH dependent aldehyde/alcohol dehydrogenase responsible for butanol production in alcohologenic cultures of *Clostridium acetobutylicum* ATCC 824. J. Bacteriol. 184: 821-830.

Garza E, Zhao J, Wang Y, Wang J, Iverson A, Manow R, Finan C, Zhou S. 2012. Engineering a homobutanol fermentation pathway in *Escherichia coli* EG03. J Ind Microbiol Biotechnol., 39:1101-1107.

Girbal L., and Soucaille P. 1998. Regulation of solvent production in *Clostridium acetobutylicum*. Trends. Biotechnol. 16, 11-16.

Girbal L., Von Abendroth G., Winkler M., Benton P. M. C., Meynial-Salles I., Croux C., Peters J., Happe T. and Soucaille P. 2005. Homologous/heterologous over-expression in *Clostridium acetobutylicum* and characterization of purified clostridial and algal Fe-only hydrogenases with high specific activity: *Appl. Environ. Microbiol.* 71, 2777-2781.

Girio, F. M., C. Fonseca, F. Carvalheiro, L. C. Duarte, S. Marques, and R. Bogel-Lukasik. 2010. Hemicelluloses for fuel ethanol: A review. Bioresour Technol 101:4775-800.

Heap J T, Pennington O J, Cartman S T, Carter G P, Minton N P 2007. The ClosTron: a universal gene knock-out system for the genus *Clostridium*. J Microbiol Methods. 70:452-64

Meynial-Salles I.*, Gonzalez-Pajuelo M.*, Mendes P., Andrade J. C., Vasconcelos I. and Soucaille P. 2005. Metabolic engineering of *Clostridium acetobutylicum* for the industrial production of 1.3 propanediol from glycerol: Met. Eng., 7, 329-336: * equivalent contribution.

Harrington K. J., Laughlin R. B. and Liang S. 2001. Balanced branching in transcription termination. Proc Natl Acad Sci USA. 98(9):5019-24. Ingram L. and Beall D. 1992. Ethanol production by recombinant hosts: WO9216615.

Inui M, Suda M, Kimura S, Yasuda K, Suzuki H, Toda H, Yamamoto S, Okino S, Suzuki N, Yukawa H. 2008. Expression of *Clostridium acetobutylicum* butanol synthetic genes in *Escherichia coli*: Appl Microbiol Biotechnol. 77: 1305-16.

Jang Y S, Lee J Y, Lee J, Park J H, Im J A, Eom M H, Lee J, Lee S H, Song H, Cho J H, Seung do Y, Lee S Y. 2012. Enhanced butanol production obtained by reinforcing the direct butanol-forming route in *Clostridium* acetobutylicum. mBio, 3, 1-5.

Jarboe L. R., Grabar T. B., Yomano L. P., Shanmugan K. T. and Ingram L. O. 2007. Development of ethanologenic bacteria, Adv. Biochem. Engin. Biotechnol., 108:237-61.

Jiang Y, Xu C, Dong F, Yang Y, Jiang W, Yang S. 2009. Disruption of the acetoacetate decarboxylase gene in solvent-producing *Clostridium acetobutylicum* increases the butanol ratio. Met. Eng. 11:284-291.

Keseler I M, Collado-Vides J, Gama-Castro S, Ingraham J, Paley S, Paulsen I T, Peralta-Gil M, Karp P D. 2005. EcoCyc: a comprehensive database resource for *Escherichia coli*, Nucleic Acids Res. 1; 33 (Database issue): D334-7.

Kim Y., Ingram L. O. and Shanmugan K. T. 2007. Construction of an *Escherichia coli* K12 mutant for homoethanologenic fermentation of glucose or xylose without foreign genes: Appl Environ Microb 73: 1766-71.

Lau M W, Gunawan C., Balan V. and Dale B. E. 2010 Comparing the fermentation performance of *Escherichia coli*K011, *Saccharomyces cerevisiae*424(LNH-ST) and *Zymomonas mobilis* AX101 for cellulosic ethanol production. Biotechnol. Biofuels, 3, 11.

Li F, Hinderberger J, Seedorf H, Zhang J, Buckel W, Thauer R K. 2008. Coupled ferredoxin and crotonyl coenzyme A (CoA) reduction with NADH catalyzed by the butyryl-CoA dehydrogenase/Etf complex from *Clostridium kluyveri*: J Bacteriol. 190. 843-50.

Matsuoka K, Kimura K. 1986. Glutamate synthase from *Bacillus subtilis* PCI 219. J Biochem. 99(4):1087-100

Mermelstein, L. D., Welker, N. E., Bennett, G. G., Papoutsakis, E. T., 1992. Expression of cloned homologous fermentative genes in *Clostridium acetobutylicum* ATCC 824. Biotechnology. 10, 190-195.

Miller J, H. 1972. Experiments in molecular genetics. Cold Spring Harbor Laboratory Press, Cold Spring Harbor N. Y.

Meynial-Salles I., Cervin M. A. and Soucaille P. 2005. New tool for metabolic pathway engineering in *E. coli*: one step method to modulate the expression of chromosomal genes: Appl. Environ. Microbiol. 71, 2140-2144

Meynial-Salles I., Gonzalez B. and Soucaille P. 2005 Microorganismes évolués pour la production de 1.2 propanediol: PCT/FRO5/00070.

Meynial-Salles I.*, Gonzalez-Pajuelo M.*, Mendes P., Andrade J. C., Vasconcelos I. and Soucaille P. 2005. Metabolic engineering of *Clostridium acetobutylicum* for the industrial production of 1.3 propanediol from glycerol: Met. Eng., 7, 329-336: * equivalent contribution.

Nöilling J, Breton G, Omelchenko M V, Makarova K S, Zeng Q, Gibson R, Lee H M, Dubois J, Qiu D, Hitti J, Wolf Y I, Tatusov R L, Sabathe F, Doucette-Stamm L, Soucaille P, Daly M J, Bennett G N, Koonin E V, Smith D R. 2001. Genome sequence and comparative analysis of the solvent-producing bacterium *Clostridium acetobutylicum*, J Bacteriol. 183(16):4823-38

Norrander, J., T. Kempe, and J. Messing. 1983. Construction of improved M13 vectors using oligodeoxynucleotide-directed mutagenesis. Gene 26:101-106.

Nielsen D. R., Leonard E, Yoon S H, Tseng H C, Yuan C, Prather K L 2009. Engineering alternative butanol production platforms in heterologous bacteria. Met. Eng. 11: 262-273.

Papoutsakis E T. 2008. Engineering solventogenic *clostridia*. Curr Opin Biotechnol., 19:420-9.

Perutka J, Wang W, Goerlitz D, Lambowitz A M 2004, Use of computer-designed group II introns to disrupt *Escherichia coli* DExH/D-box protein and DNA helicase genes. J Mol Biol. 336:421-39.

Saint-Amans S, Girbal L, Andrade J, Ahrens K, Soucaille P. 2001 Regulation of carbon and electron flow in *Clostridium* butyricum VPI 3266 grown on glucose-glycerol mixtures, J. bacteriol., 183:1748-54.

Sambrook J, Russell D W 2001. Molecular Cloning: A Laboratory Manual. Cold Spring Harbor Laboratory Press, Cold Spring Harbor, New York Sanchez-Rivera F, Cameron D C, and Cooney D C 2001. Influence of environmental factors in the production of 1.2 propanediol by *Clostridium* thermosaccharolyticum, Biotechnol. Lett. 9, 449-454.

Sarçabal P. Croux C. Soucaille P. 1999. PCT no FR00/ 01981, Procédé de préparation du 1,3-Propanediol par un micro-organisme recombinant en l'absence de coenzyme B12 ou de l'un de ses précurseurs Saxena R K, Anand P, Saran S, Isar J. 2009 Microbial production of 1,3-propanediol: Recent developments and emerging opportunities. Biotechnol Adv., 27, 895-9.

Saxena R K, Anand P, Saran S, Isar J, Agarwal L. 2010 Microbial production and applications of 1,2-propanediol. Indian J Microbiol, 50, 2-11.

Schaefer U, Boos W, Takors R, Weuster-Botz D 1999. Automated sampling device for monitoring intracellular metabolite dynamics *Anal. Biochem.* 270: 88-96

Shen C. R., Lan E. I., Dekishima Y., Baez A., Cho K. M., Liao J. C. 2011. Driving forces Enable High-Titer Anaerobic 1-Butanol Synthesis in *Escherichia coli*. Appl. Environ. Microbiol. 77: 2905-15.

Singhal R K, Krishnan I S, Dua R D. 1989 Stabilization, purification, and characterization of glutamate synthase from *Clostridium* pasteurianum, Biochemistry. 28(19): 7928-35

Soucaille P., Cervin M., Valle F. 2012. Method of Creating a Library of Bacterial Clones with Varying Levels of Gene Expression US2012015849.

Soucaille, P., Figge, R.,Croux, C., 2006. Process for Chromosomal Integration and DNA Sequence Replacement in Clostridia. Patent WO2006EP66997 20061003.

Soucaille, P., 2007. Process for the biological production of n-butanol with high yield. Patent EP20070821988 20071029.

Steen E J., Chan R, Prasad N, Myers S, Petzold C J, Redding A, Ouellet M, Keasling J D. 2008 Metabolic engineering of *Saccharomyces cerevisiae* for the production of n-butanol. Microb. Cell Factories 7: 1-8.

Tang X, Tan Y, Zhu H, Zhao K, Shen W. 2009 Microbial conversion of glycerol to 1,3-propanediol by an engineered strain of *Escherichia coli*. Appl. Environ. Microbiol., 1628-1634.

Tracy B. 2012. Improving butanol fermentation to enter the advanced biofuel market. MBio. 3: 1-3.

Tran Din K. and Gottschalk G. 1985 Formation of D(-)-1, 2-propanediol and D(-)-lactate from glucose by *Clostridium sphenoides* under phosphate limitation: Arch. Microbiol. 142, 87-92.

Trinh C T, Huffer S, Clark M E, Blanch H W, Clark D S 2010 Elucidating mechanisms of solvent toxicity in ethanologenic *Escherichia coli*. Biotechnol Bioeng. 106:721-30

Vanoni M A, Curti B. 1999 Glutamate synthase: a complex iron-sulfur flavoprotein. Cell Mol Life Sci. 55(4):617-38. Review Vasconcelos, I., Girbal, L., Soucaille, P., 1994. Regulation of carbon and electron flow in *Clostridium acetobutylicum* grown in chemostat culture at neutral pH on mixtures of glucose and glycerol. J. Bacteriol. 176, 1443-1450.

Xu Y Z[1], Guo N N, Zheng Z M, Ou X J, Liu H J, Liu D H. 2009. Metabolism in 1,3-propanediol fed-batch fermentation by a D-lactate deficient mutant of Klebsiella pneumoniae. Biotechnol Bioeng, 104, 965-972.

Yu M, Du Y, Jiang W, Chang W L, Yang S T, Tang I C. 2012 Effects of different replicons in conjugative plasmids on transformation efficiency, plasmid stability, gene expression and n-butanol biosynthesis in *Clostridium tyrobutyricum*. Appl. Microbiol. Biotechnol. 881-9.

---

SEQUENCE LISTING

```
<160> NUMBER OF SEQ ID NOS: 95

<210> SEQ ID NO 1
<211> LENGTH: 411
<212> TYPE: PRT
<213> ORGANISM: C. acetobutylicum

<400> SEQUENCE: 1

Met Asp Asn Pro Asn Leu Leu Ser Glu Glu Ala Asn Arg Cys Leu Leu
1               5                   10                  15

Cys Lys Asn Pro Arg Cys Lys Ala Asn Cys Pro Ile Asn Thr Pro Ile
            20                  25                  30

Pro Glu Ile Ile Ser Leu Tyr Lys Glu Gly Lys Ile Met Glu Ala Gly
        35                  40                  45

Glu Ile Leu Phe Asn Asn Asn Pro Leu Ser Val Ile Cys Ser Leu Val
    50                  55                  60

Cys Ile His Glu Asp Gln Cys Lys Gly Asn Cys Val Arg Gly Ile Lys
65                  70                  75                  80

Ser Glu Pro Ile Lys Phe His Glu Ile Glu Glu Glu Ile Ser Glu Lys
                85                  90                  95

Tyr Leu Lys Glu Ala Lys Leu Lys Asn Val Gln Lys Asp Lys Asp Arg
            100                 105                 110

Ile Ala Ile Val Gly Gly Gly Pro Ala Gly Ile Thr Val Ala Phe Val
        115                 120                 125

Leu Ala Asn Lys Gly Tyr Asn Val Thr Ile Phe Glu Ala His Asp Lys
    130                 135                 140

Ile Gly Gly Val Leu Arg Tyr Gly Ile Pro Glu Tyr Arg Leu Thr Lys
145                 150                 155                 160

Lys Leu Val Asp Lys Leu Glu Glu Arg Leu Ile Glu Val Gly Val Lys
                165                 170                 175

Ile Arg Pro Asn Thr Val Ile Gly Pro Val Ile Ser Leu Asp Arg Leu
            180                 185                 190
```

Leu Glu Asp Ser Tyr Lys Ala Val Phe Ile Gly Thr Gly Val Trp Asn
         195                 200                 205

Pro Lys Thr Leu Asp Val Lys Gly Glu Thr Leu Gly Asn Val His Phe
        210                 215                 220

Ala Ile Asp Tyr Leu Lys Ser Pro Glu Ser Tyr Arg Leu Gly Lys Lys
225                 230                 235                 240

Val Ala Val Ile Gly Ala Gly Asn Val Ala Met Asp Ala Ala Arg Thr
                245                 250                 255

Ala Lys Arg Asn Gly Ala Glu Val Thr Ile Leu Tyr Arg Lys Ser Phe
            260                 265                 270

Asn Glu Met Pro Ala Ser Lys Gln Glu Ile Arg Glu Thr Lys Glu Asp
        275                 280                 285

Gly Val Glu Phe Lys Leu Phe Arg Ala Pro Ile Glu Ile Thr Glu Glu
        290                 295                 300

Gly Ile Lys Val Ala Phe Thr Glu Asn Val Thr Asp Ala Glu Gly Lys
305                 310                 315                 320

Ile Arg Thr Lys Ile Ile Glu Gly Lys Glu Glu Phe Phe Glu Cys Asp
                325                 330                 335

Ser Val Val Ala Val Ser Gln Ala Pro Lys Asp Asn Ile Val Ser
            340                 345                 350

Asn Thr Thr Gly Leu Asp Thr Lys Trp Gly Leu Ile Val Thr Asp Glu
        355                 360                 365

Lys Gly Asn Thr Thr Lys Lys Gly Thr Phe Ala Cys Gly Asp Val Val
        370                 375                 380

Thr Gly Ala Lys Thr Val Val Glu Ala Ala Ala Gln Ala Lys Val Val
385                 390                 395                 400

Ala Glu Thr Ile Asp Glu Tyr Cys Lys Asn Asn
                405                 410

<210> SEQ ID NO 2
<211> LENGTH: 1236
<212> TYPE: DNA
<213> ORGANISM: C. acetobutylicum

<400> SEQUENCE: 2
atggataacc ctaatttatt gtcagaagag gcaaacagat gcctactatg caaaaaccct     60
agatgtaaag caaattgccc tattaataca cccataccag aaattataag cctttataaa    120
gaaggaaaaa ttatggaagc aggagaaatt ttatttaata caatcctctt ttcagtaata    180
tgctcattgg tctgtattca tgaggatcaa tgtaagggaa attgtgtaag aggaataaaa    240
agcgagccaa taaaatttca cgagatagaa gaagagatat cagagaagta cttaaaagag    300
gccaagctta agaatgttca gaggacaag gatagaattg caatagttgg aggaggtcca    360
gcaggaatca cagttgcatt tgtacttgct aataaaggct ataatgttac cattttgag    420 gctcacgata aaataggagg agtacttaga tatggtattc cagagtatag attgactaag    480
aaattagtgg ataagcttga agaaagactt atagaggttg gagtgaaaat tagacctaat    540
actgttattg gaccagttat ttctttggac aggttacttg aagattcata taaggcagta    600
tttattggaa ctggagtatg gaatccaaaa accttagatg taaagggaga actttagga    660 aatgttcatt ttgctattga ttatttaaaa tctcctgaaa gctatagatt aggaaaaaaa    720
gtagctgtaa taggagcagg taatgttgcc atggatgctg caagaactgc taagagaaat    780
ggtgctgagg taacaatact ttatagaaaa agctttaatg agatgccagc atcaaaacaa    840

```
gaaataagag aaactaaaga agatggagta gagtttaaat tatttagagc accaattgaa    900
ataacagaag agggtattaa agtagcattt acagaaaatg ttacagatgc agaaggaaaa    960
ataagaacta aaattattga aggaaaagaa gagttttttg agtgtgattc agtagttgtt   1020
gccgtaagtc aagcacctaa ggataatata gtatctaata caacaggctt agatactaaa   1080
tggggattaa tagtaacaga tgaaaaaggc aatacaacta aaaaggaac  ctttgcatgt   1140 ggagatgtag ttacaggagc aaaaactgta gttgaagctg cagcacaagc aaaagtagtt   1200
gcagaaacta ttgatgagta ttgcaagaat aattaa                             1236
```

<210> SEQ ID NO 3
<211> LENGTH: 53
<212> TYPE: DNA
<213> ORGANISM: artificial
<220> FEATURE:
<223> OTHER INFORMATION: primer : 408/409s-IBS consisting of 53 bases

<400> SEQUENCE: 3

```
aaaaaagctt ataattatcc ttaggctaca atgttgtgcg cccagatagg gtg            53
```

<210> SEQ ID NO 4
<211> LENGTH: 60
<212> TYPE: DNA
<213> ORGANISM: artificial
<220> FEATURE:
<223> OTHER INFORMATION: primer:408/409s-EBS1d consisting of 60 bases

<400> SEQUENCE: 4

```
cagattgtac aaatgtggtg ataacagata agtcaatgtt actaacttac ctttctttgt    60
```

<210> SEQ ID NO 5
<211> LENGTH: 49
<212> TYPE: DNA
<213> ORGANISM: artificial
<220> FEATURE:
<223> OTHER INFORMATION: primer:408/409s-EBS2 consisting of 49 bases

<400> SEQUENCE: 5

```
tgaacgcaag tttctaattt cgatttagcc tcgatagagg aaagtgtct                 49
```

<210> SEQ ID NO 6
<211> LENGTH: 25
<212> TYPE: DNA
<213> ORGANISM: artificial
<220> FEATURE:
<223> OTHER INFORMATION: primer: homologous to the E. coli sequence
      886263 to 886287

<400> SEQUENCE: 6

```
cgagccaata aaatttcacg agata                                           25
```

<210> SEQ ID NO 7
<211> LENGTH: 30
<212> TYPE: DNA
<213> ORGANISM: artificial
<220> FEATURE:
<223> OTHER INFORMATION: primer: homologous to the E. coli sequence
      886512 to 886541

<400> SEQUENCE: 7

```
ccaacctcta taagtctttc ttcaagctta                                      30
```

<210> SEQ ID NO 8
<211> LENGTH: 30

-continued

```
<212> TYPE: DNA
<213> ORGANISM: artificial
<220> FEATURE:
<223> OTHER INFORMATION: primer: Ocac0764f

<400> SEQUENCE: 8
aggatccatc aaaatttagg aggttagtta                                    30

<210> SEQ ID NO 9
<211> LENGTH: 39
<212> TYPE: DNA
<213> ORGANISM: artificial
<220> FEATURE:
<223> OTHER INFORMATION: primer: Ocac0764r

<400> SEQUENCE: 9
ggcgccttaa ttattcttgc aatactcatc aatagtttc                          39

<210> SEQ ID NO 10
<211> LENGTH: 101
<212> TYPE: DNA
<213> ORGANISM: artificial
<220> FEATURE:
<223> OTHER INFORMATION: primer: a region homologous to the sequence
      (1439878-1439958) of the ldhA gene (sequence  1439878 to 1440867),
      and a region for the amplification of the chloramphenicol
      resistance cassette of the pKD3 plasmid

<400> SEQUENCE: 10
ttaaaccagt tcgttcgggc aggtttcgcc ttttccaga ttgcttaagt tttgcagcgt    60
agtctgagaa atactggtca gcatatgaat atcctcctta g                      101

<210> SEQ ID NO 11
<211> LENGTH: 100
<212> TYPE: DNA
<213> ORGANISM: artificial
<220> FEATURE:
<223> OTHER INFORMATION: primer: a region homologous to the sequence
      (1440786-1440865) of the ldhA gene (sequence 1439878 to 1440867),
      and a region for the amplification of the chloramphenicol
      resistance cassette carried by the pKD3 plasmid.

<400> SEQUENCE: 11
gaaactcgcc gtttatagca caaaacagta cgacaagaag tacctgcaac aggtgaacga    60
gtcctttggc tttgagctgg tgtaggctgg agctgcttcg                         100

<210> SEQ ID NO 12
<211> LENGTH: 20
<212> TYPE: DNA
<213> ORGANISM: artificial
<220> FEATURE:
<223> OTHER INFORMATION: primer: homologous to the E. coli  sequence
      1439724 to 1439743

<400> SEQUENCE: 12
gccatcagca ggcttagcgc                                               20

<210> SEQ ID NO 13
<211> LENGTH: 23
<212> TYPE: DNA
<213> ORGANISM: artificial
<220> FEATURE:
<223> OTHER INFORMATION: primer: homologous to the E. coli sequence
      1441007 to 1441029

<400> SEQUENCE: 13
```

```
gggtattgtg gcatgtttaa ccg                                             23

<210> SEQ ID NO 14
<211> LENGTH: 100
<212> TYPE: DNA
<213> ORGANISM: artificial
<220> FEATURE:
<223> OTHER INFORMATION: primer: a region homologous to the sequence
      (952236 -952315) of the pflB gene (sequence 950495-952777), and a
      region (upper-case letters) for the amplification of the
      chloramphenicol resistance cassette of the pKD3 plasmid

<400> SEQUENCE: 14
ccggacatcc tgcgttgccg taaatctggt gttctgaccg gtctgccaga tgcatatggc       60
cgtggccgta tcatcggtga catatgaata tcctccttag                           100

<210> SEQ ID NO 15
<211> LENGTH: 100
<212> TYPE: DNA
<213> ORGANISM: artificial
<220> FEATURE:
<223> OTHER INFORMATION: primer: a region homologous to the sequence
      (949470-949549) located upstream the pflA gene (sequence 949563-
      950303), and a region for the amplification of the chloramphenicol
      resistance cassette carried by the pKD3 plasmid.

<400> SEQUENCE: 15
gatgcactat aagatgtgtt aaaaacgctg tagcagaatg aagcgcggaa taaaaaagcg       60
gcaactcaat aaagttgccg tgtaggctgg agctgcttcg                           100

<210> SEQ ID NO 16
<211> LENGTH: 30
<212> TYPE: DNA
<213> ORGANISM: artificial
<220> FEATURE:
<223> OTHER INFORMATION: primer : homologous to the E. coli the sequence
      948462 to 948491

<400> SEQUENCE: 16
agacattaaa aatatacgtg cagctacccg                                       30

<210> SEQ ID NO 17
<211> LENGTH: 30
<212> TYPE: DNA
<213> ORGANISM: artificial
<220> FEATURE:
<223> OTHER INFORMATION: primer : homologous to the E. coli sequence
      953660 to 953689

<400> SEQUENCE: 17
gtgaaagctg acaaccctt tgatctttta                                        30

<210> SEQ ID NO 18
<211> LENGTH: 100
<212> TYPE: DNA
<213> ORGANISM: artificial
<220> FEATURE:
<223> OTHER INFORMATION: primer: a region homologous to the sequence
      (2411494-2411573) of the ackA gene (sequence  2411492 to 2412694),
      and a region for the amplification of the chloramphenicol
      resistance cassette of the pKD3 plasmid

<400> SEQUENCE: 18
gtcgagtaag ttagtactgg ttctgaactg cggtagttct tcactgaaat ttgccatcat       60
cgatgcagta aatggtgaag tgtaggctgg agctgcttcg                           100
```

<210> SEQ ID NO 19
<211> LENGTH: 97
<212> TYPE: DNA
<213> ORGANISM: artificial
<220> FEATURE:
<223> OTHER INFORMATION: primer: a region homologous to the sequence
    (2414906-2414830) of the pta gene (sequence 2412769 to 2414913),
    and a region for the amplification of the chloramphenicol
    resistance cassette carried by the pKD3 plasmid.

<400> SEQUENCE: 19
tgctgtgcag actgaatcgc agtcagcgcg atggtgtaga cgatatcgtc aaccagtgcg      60
ccacgggaca ggtcgttcat atgaatatcc tccttag                              97

<210> SEQ ID NO 20
<211> LENGTH: 20
<212> TYPE: DNA
<213> ORGANISM: artificial
<220> FEATURE:
<223> OTHER INFORMATION: primer : homologous to the E. coli sequence
    2410902 to 2410921

<400> SEQUENCE: 20
gcatgggtaa acttaaggcg                                                 20

<210> SEQ ID NO 21
<211> LENGTH: 20
<212> TYPE: DNA
<213> ORGANISM: artificial
<220> FEATURE:
<223> OTHER INFORMATION: primer : homologous to the E. coli sequence
    2415147 to 2415166

<400> SEQUENCE: 21
taatcaccaa cgtatcgggc                                                 20

<210> SEQ ID NO 22
<211> LENGTH: 70
<212> TYPE: DNA
<213> ORGANISM: artificial
<220> FEATURE:
<223> OTHER INFORMATION: primer: a region homologous to the seq
    (2660151-2660200) corresponding to the upstream chromosomal seq of
    the iscR gene (seq 2659665 to 2660153), and a region for the
    amplification of the kanamycin resistance cassette carried by the
    pKD13 plasmid

<400> SEQUENCE: 22
tacaataaaa aacccccgggc aggggcgagt ttgaggtgaa gtaagacatg attccgggga     60
tccgtcgacc                                                            70

<210> SEQ ID NO 23
<211> LENGTH: 70
<212> TYPE: DNA
<213> ORGANISM: artificial
<220> FEATURE:
<223> OTHER INFORMATION: primer: a region homologous to the sequence
    (2659636-2659685) corresponding to the downstream chromosomal
    sequence of the iscR gene (sequence 2659665 to 2660153), and a
    region for the amplification of the kanamycin resistance cassette
    of the pKD13

<400> SEQUENCE: 23
cactccggcc tgattctgaa ttcttttat taagcgcgta acttaacgtc tgtaggctgg       60
agctgcttcg                                                            70

<210> SEQ ID NO 24
<211> LENGTH: 19
<212> TYPE: DNA
<213> ORGANISM: artificial
<220> FEATURE:
<223> OTHER INFORMATION: primer: homologous to the E. coli sequence 2660325 to 2660343

<400> SEQUENCE: 24
cgccgcatcc gacaacagg                                                19

<210> SEQ ID NO 25
<211> LENGTH: 23
<212> TYPE: DNA
<213> ORGANISM: artificial
<220> FEATURE:
<223> OTHER INFORMATION: primer: homologous to the E; coli sequence 2659253 to 2659275

<400> SEQUENCE: 25
tgctggtgat gatgtgcttg cct                                           23

<210> SEQ ID NO 26
<211> LENGTH: 70
<212> TYPE: DNA
<213> ORGANISM: artificial
<220> FEATURE:
<223> OTHER INFORMATION: primer : a region homologous to the seq (4380339-4380388) corresponding to the upstream chromosomal seq of the frdA gene (seq 4378533 to 4380341), and a region for the amplification of the chloramphenicol resistance cassette of the plasmid pKD3

<400> SEQUENCE: 26
accctgaagt acgtggctgt gggataaaaa caatctggag gaatgtcgtg tgtaggctgg   60
agctgcttcg                                                          70

<210> SEQ ID NO 27
<211> LENGTH: 70
<212> TYPE: DNA
<213> ORGANISM: artificial
<220> FEATURE:
<223> OTHER INFORMATION: primer: a region homologous to the seq (4377001-4377050) corresponding to the downstream chromosomal seq of the frdD gene (seq 4377030 to 4377389), and a region for the amplification of the chloramphenicol resistance cassette carried by pKD3

<400> SEQUENCE: 27
aggcgggccg gatttacatt ggcgatgcgt tagattgtaa cgacaccaat catatgaata   60
tcctccttag                                                          70

<210> SEQ ID NO 28
<211> LENGTH: 22
<212> TYPE: DNA
<213> ORGANISM: artificial
<220> FEATURE:
<223> OTHER INFORMATION: primer: homologous to the E. coli sequence 4380779 to 4380800

<400> SEQUENCE: 28
ctggctcata caaggcgtct cc                                            22

<210> SEQ ID NO 29
<211> LENGTH: 23
<212> TYPE: DNA

```
<213> ORGANISM: artificial
<220> FEATURE:
<223> OTHER INFORMATION: primer: homologous to the E coli sequence
      4376610 to 4376632

<400> SEQUENCE: 29
tcccattcca ctgtttagcg gta                                           23

<210> SEQ ID NO 30
<211> LENGTH: 70
<212> TYPE: DNA
<213> ORGANISM: artificial
<220> FEATURE:
<223> OTHER INFORMATION: primer: a region homologous to the seq
      (122970-123019) corresponding to the upstream chromosomal seq of
      the aceE gene (seq 123017 to 125680), and a region for the
      amplification of the kanamycin resistance cassette carried by the
      pKD13 plasmid

<400> SEQUENCE: 30
acaggttcca gaaaactcaa cgttattaga tagataagga ataacccatg attccgggga   60
tccgtcgacc                                                         70

<210> SEQ ID NO 31
<211> LENGTH: 70
<212> TYPE: DNA
<213> ORGANISM: artificial
<220> FEATURE:
<223> OTHER INFORMATION: primer: a region homologous to the seq
      (125660-125709) corresponding to the downstream chromosomal seq of
      the aceE gene (seq 123017 to 125680), and a region for the
      amplification of the kanamycin resistance cassette of the pKD13
      plasmid

<400> SEQUENCE: 31
gatttcgata gccattattc ttttacctct tacgccagac gcgggttaac tgtaggctgg   60
agctgcttcg                                                         70

<210> SEQ ID NO 32
<211> LENGTH: 20
<212> TYPE: DNA
<213> ORGANISM: artificial
<220> FEATURE:
<223> OTHER INFORMATION: primer: homologous to the E. coli sequence
      122806 to 122825

<400> SEQUENCE: 32
gagagccgcc gtgagcgttc                                               20

<210> SEQ ID NO 33
<211> LENGTH: 20
<212> TYPE: DNA
<213> ORGANISM: artificial
<220> FEATURE:
<223> OTHER INFORMATION: primer: homologous to the E. coli sequence
      125916 to 125935

<400> SEQUENCE: 33
ctgcaccgtc ggcggaatcg                                               20

<210> SEQ ID NO 34
<211> LENGTH: 70
<212> TYPE: DNA
<213> ORGANISM: artificial
<220> FEATURE:
<223> OTHER INFORMATION: primer: a region homologous to the seq
      (1026236-1026285) corresponding to the upstream chromosomal seq of
``` the mgsA gene (seq 1025780 to 1026238), and a region for the
amplification of the chloramphenicol resistance cassette of the
pKD3 plasmid

<400> SEQUENCE: 34
taagtgctta cagtaatctg taggaaagtt aactacggat gtacattatg tgtaggctgg    60
agctgcttcg    70

<210> SEQ ID NO 35
<211> LENGTH: 70
<212> TYPE: DNA
<213> ORGANISM: artificial
<220> FEATURE:
<223> OTHER INFORMATION: primer: a region homologous to the seq
      (1025751-1025800) corresponding to the downstream chromosomal seq
      of the mgsA gene (seq 1025780 to 1026238), and a region for the
      amplification of the chloramphenicol resistance cassette carried
      by pKD3

<400> SEQUENCE: 35
aacaggtggc gtttgccacc tgtgcaatat tacttcagac ggtccgcgag catatgaata    60
tcctccttag    70

<210> SEQ ID NO 36
<211> LENGTH: 20
<212> TYPE: DNA
<213> ORGANISM: artificial
<220> FEATURE:
<223> OTHER INFORMATION: primer: homologous to the E. coli sequence
      1026715 to 1026734

<400> SEQUENCE: 36
cccagctcat caaccaggtc    20

<210> SEQ ID NO 37
<211> LENGTH: 22
<212> TYPE: DNA
<213> ORGANISM: artificial
<220> FEATURE:
<223> OTHER INFORMATION: primer: homologous to the E. coli sequence
      1025559 to 1025580

<400> SEQUENCE: 37
ggagtcgatt atggaagagg cg    22

<210> SEQ ID NO 38
<211> LENGTH: 101
<212> TYPE: DNA
<213> ORGANISM: artificial
<220> FEATURE:
<223> OTHER INFORMATION: primer: a region homologous to the sequence
      (1297264 -1297344) including the adhE gene initiation codon of the
      adhE gene (sequence 1294669 to 1297344), and a region for the
      amplification of the chloramphenicol resistance cassette of the
      pKD3 plasmid

<400> SEQUENCE: 38
atggctgtta ctaatgtcgc tgaacttaac gcactcgtag agcgtgtaaa aaaagcccag    60
cgtgaatatg ccagtttcac tcatatgaat atcctcctta g    101

<210> SEQ ID NO 39
<211> LENGTH: 100
<212> TYPE: DNA
<213> ORGANISM: artificial
<220> FEATURE:
<223> OTHER INFORMATION: primer: a region homologous to the seq -continued (1294693-1294748) corresponding to the downstream chromosomal seq
of the adhE gene (sequence1294669 to 1297344), and a region for
the amplification of the chloramphenicol resistance cassette
carried by pKD3

<400> SEQUENCE: 39
ttaagcggat tttttcgctt ttttctcagc tttagccgga gcagcttctt tcttcgctgc    60
agtttcacct tctacataat tgtaggctgg agctgcttcg                         100

<210> SEQ ID NO 40
<211> LENGTH: 22
<212> TYPE: DNA
<213> ORGANISM: artificial
<220> FEATURE:
<223> OTHER INFORMATION: primer : homologous to the E. coli sequence
      1294357 to 1294378

<400> SEQUENCE: 40
ggctcattgc accaccatcc ag                                             22

<210> SEQ ID NO 41
<211> LENGTH: 24
<212> TYPE: DNA
<213> ORGANISM: artificial
<220> FEATURE:
<223> OTHER INFORMATION: primer : homologous to the E. coli sequence
      1297749 to 1297772

<400> SEQUENCE: 41
gaaaagacgc gctgacaata cgcc                                           24

<210> SEQ ID NO 42
<211> LENGTH: 22
<212> TYPE: DNA
<213> ORGANISM: artificial
<220> FEATURE:
<223> OTHER INFORMATION: primer Ome1847

<400> SEQUENCE: 42
ttcgtcacgg aatcgtcaga ac                                             22

<210> SEQ ID NO 43
<211> LENGTH: 23
<212> TYPE: DNA
<213> ORGANISM: artificial
<220> FEATURE:
<223> OTHER INFORMATION: primer Ome1850

<400> SEQUENCE: 43
cctgatttat accggcattt cgg                                            23

<210> SEQ ID NO 44
<211> LENGTH: 20
<212> TYPE: DNA
<213> ORGANISM: artificial
<220> FEATURE:
<223> OTHER INFORMATION: primer: homologous to the E. coli sequence from
      4340168 to 4340187

<400> SEQUENCE: 44
gccgattttg tcgtggtggc                                                20

<210> SEQ ID NO 45
<211> LENGTH: 22
<212> TYPE: DNA
<213> ORGANISM: artificial

```
<220> FEATURE:
<223> OTHER INFORMATION: primer: homologous to the E. coli sequence
      from 4344065 to 4344044

<400> SEQUENCE: 45
gccggttatc catcaggttc ac                                              22

<210> SEQ ID NO 46
<211> LENGTH: 20
<212> TYPE: DNA
<213> ORGANISM: artificial
<220> FEATURE:
<223> OTHER INFORMATION: primer: Homologous to a region for the
      amplification of the chloramphenicol resistance cassette of the
      pKD3 plasmid

<400> SEQUENCE: 46
tgtaggctgg agctgcttcg                                                 20

<210> SEQ ID NO 47
<211> LENGTH: 94
<212> TYPE: DNA
<213> ORGANISM: artificial
<220> FEATURE:
<223> OTHER INFORMATION: primer:a region homologous to the seq 2324141-
      2324131 of the atoB gene, a region homologous to the RBS01*2
      consensus seq, a region containing the artificial ptrc30 promoter,
      a region for the amplification of the chloramphenicol resistance
      cassette of pKD3

<400> SEQUENCE: 47
caatttttca tttataacct ccttattcca cacagtatac gagccggatg attaatcgtc     60
aacagctcca tggtccatat gaatatcctc ctta                                 94

<210> SEQ ID NO 48
<211> LENGTH: 137
<212> TYPE: DNA
<213> ORGANISM: artificial
<220> FEATURE:
<223> OTHER INFORMATION: Primer: a region homologous to the seq 2324042-
      2324130 upstream of the atoB gene, a region corresponding to the
      transcriptional terminator T7T of the T7 phage and a region for
      the amplification of the chloramphenicol resistance cassette of
      the pKD3 plasmid

<400> SEQUENCE: 48
gcatcactgc cctgctcttc tccggtgtca ttttcgtcat tggtttaacg ctgttctgac     60 ggcacccta caaacagaag gaatataaac tggctcacct tcgggtgggc ctttctgctg    120
taggctggag ctgcttc                                                   137

<210> SEQ ID NO 49
<211> LENGTH: 114
<212> TYPE: DNA
<213> ORGANISM: artificial
<220> FEATURE:
<223> OTHER INFORMATION: primer: a region homologous to the sequence
      2324230-2324131 of the atoB gene (sequence 2324131 to 2325315) and
      a region homologous to the RBS01*2 consensus sequence containing
      the PsiI restriction site

<400> SEQUENCE: 49
ttactgtcgc ccccaggtcg atggcgctgg tggaagcgag tgaaccgtta aaactaccga     60
tagcagtacg taccgcactg acgatgacac aatttttcat ttataacctc ctta          114

<210> SEQ ID NO 50
```

```
<211> LENGTH: 19
<212> TYPE: DNA
<213> ORGANISM: artificial
<220> FEATURE:
<223> OTHER INFORMATION: primer: homologous to the E. coli sequence
      2323667 to 2323685

<400> SEQUENCE: 50
gcgcggcagc acgcagtac                                              19

<210> SEQ ID NO 51
<211> LENGTH: 20
<212> TYPE: DNA
<213> ORGANISM: artificial
<220> FEATURE:
<223> OTHER INFORMATION: primer: homologous to the E. coli sequence
      2324584 to 2324565

<400> SEQUENCE: 51
cgcacatcag gccatcgcgc                                             20

<210> SEQ ID NO 52
<211> LENGTH: 59
<212> TYPE: DNA
<213> ORGANISM: artificial
<220> FEATURE:
<223> OTHER INFORMATION: primer udhA-NheIf

<400> SEQUENCE: 52
aattgctagc attatataca aggaggaaac agctatgcca cattcctacg attacgatg   59

<210> SEQ ID NO 53
<211> LENGTH: 44
<212> TYPE: DNA
<213> ORGANISM: artificial
<220> FEATURE:
<223> OTHER INFORMATION: primer udhA-xma1r

<400> SEQUENCE: 53
aattcccggg ataattttaa aacaggcggt ttaaaccgtt taac                  44

<210> SEQ ID NO 54
<211> LENGTH: 102
<212> TYPE: DNA
<213> ORGANISM: artificial
<220> FEATURE:
<223> OTHER INFORMATION: primer: a region homologous to the sequence
      (1486256-1486336) of the aldA gene (sequence 1486256 to 1487695),
      and a region (upper-case letters) for the amplification of the
      chloramphenicol resistance cassette of the pKD3 plasmid

<400> SEQUENCE: 54
atgtcagtac ccgttcaaca tcctatgtat atcgatggac agtttgttac ctggcgtgga  60
gacgcatgga ttgatgtggt agtgtaggct ggagctgctt cg                   102

<210> SEQ ID NO 55
<211> LENGTH: 101
<212> TYPE: DNA
<213> ORGANISM: artificial
<220> FEATURE:
<223> OTHER INFORMATION: primer: a region homologous to the seq
      (1487615-1487695) corresponding to the C terminal part encoding
      seq of the aldA gene (1486256 to 1487695), and a region for the
      amplification of the chloramphenicol resistance cassette of the
      pKD3 plasmid

<400> SEQUENCE: 55
```

```
ttaagactgt aaataaacca cctgggtctg cagatattca tgcaagccat gtttaccatc    60
tgcgccgcca ataccggatt tcatatgaat atcctcctta g                        101
```

<210> SEQ ID NO 56
<211> LENGTH: 31
<212> TYPE: DNA
<213> ORGANISM: artificial
<220> FEATURE:
<223> OTHER INFORMATION: primer: homologous to the E. coli sequence
      1485722 to 1485752

<400> SEQUENCE: 56

```
tgcagcggcg cacgatggcg acgttccgcc g                                   31
```

<210> SEQ ID NO 57
<211> LENGTH: 31
<212> TYPE: DNA
<213> ORGANISM: artificial
<220> FEATURE:
<223> OTHER INFORMATION: primer: homologous to the E. coli sequence
      1488195 to 1488225

<400> SEQUENCE: 57

```
cacgatgacg accattcatg cctatactgg c                                   31
```

<210> SEQ ID NO 58
<211> LENGTH: 101
<212> TYPE: DNA
<213> ORGANISM: artificial
<220> FEATURE:
<223> OTHER INFORMATION: primer: a region homologous to the sequence
      (3752996 to 3753075) of the aldB gene (sequence 3752996 to
      3754534), and a region for the amplification of the
      chloramphenicol resistance cassette of the pKD3 plasmid

<400> SEQUENCE: 58

```
tcagaacagc cccaacggtt tatccgagta gctcaccagc aggcacttgg tttgctggta    60
atgctccagc atcatcttgt gtgtaggctg gagctgcttc g                        101
```

<210> SEQ ID NO 59
<211> LENGTH: 100
<212> TYPE: DNA
<213> ORGANISM: artificial
<220> FEATURE:
<223> OTHER INFORMATION: primer: a region homologous to the sequence
      (3754455 to 3754534) of the aldB gene (sequence 3752996 to
      3754534), and a region (upper-case letters) for the amplification
      of the chloramphenicol resistance cassette of the pKD3 plasmid

<400> SEQUENCE: 59

```
atgaccaata atccccttc agcacagatt aagcccggcg agtatggttt ccccctcaag     60
ttaaaagccc gctatgacaa catatgaata tcctccttag                          100
```

<210> SEQ ID NO 60
<211> LENGTH: 40
<212> TYPE: DNA
<213> ORGANISM: artificial
<220> FEATURE:
<223> OTHER INFORMATION: primer: homologous to the E. coli sequence
      3752449 to 3752488

<400> SEQUENCE: 60

```
catatttccc tcaaagaata taaaaagaa caattaacgc                           40
```

<210> SEQ ID NO 61

```
<211> LENGTH: 31
<212> TYPE: DNA
<213> ORGANISM: artificial
<220> FEATURE:
<223> OTHER INFORMATION: primer: homologous to the E. coli 3755040 to
      3755070

<400> SEQUENCE: 61
tatgttcatg cgatggcgca ccagctgggc g                               31

<210> SEQ ID NO 62
<211> LENGTH: 100
<212> TYPE: DNA
<213> ORGANISM: artificial
<220> FEATURE:
<223> OTHER INFORMATION: primer: a region homologous to the sequence
      (3560036-3560115) of the glpD gene (sequence 3560036 to 3561541),
      and a region (upper-case letters) for the amplification of the
      chloramphenicol resistance cassette of the pKD3 plasmid

<400> SEQUENCE: 62
atggaaacca aagatctgat tgtgataggg ggcggcatca atggtgctgg tatcgcggca    60
gacgccgctg acgcggttt catatgaata tcctccttag                          100

<210> SEQ ID NO 63
<211> LENGTH: 100
<212> TYPE: DNA
<213> ORGANISM: artificial
<220> FEATURE:
<223> OTHER INFORMATION: primer : a region homologous to the seq
      (3561462-3561541) corresponding to the C terminal part encoding
      seq of the glpD gene (3560036 to 3561541), and a region for the
      amplification of the chloramphenicol resistance cassette of the
      pKD3 plasmid

<400> SEQUENCE: 63
ttacgacgcc agcgataacc tctgctgcgt atactccacc agccactgac tcacacgaga    60
ttgttgatcc gcatttagcc tgtaggctgg agctgcttcg                         100

<210> SEQ ID NO 64
<211> LENGTH: 23
<212> TYPE: DNA
<213> ORGANISM: artificial
<220> FEATURE:
<223> OTHER INFORMATION: primer: homologous to the E. coli sequence
      3559822 to 3559844

<400> SEQUENCE: 64
cgttaataca ttcgaactga tcc                                           23

<210> SEQ ID NO 65
<211> LENGTH: 23
<212> TYPE: DNA
<213> ORGANISM: artificial
<220> FEATURE:
<223> OTHER INFORMATION: primer : homologous to the E. coli sequence
      3561750 to 3561772

<400> SEQUENCE: 65
gcgtgggctt tgcggtaatt ccc                                           23

<210> SEQ ID NO 66
<211> LENGTH: 100
<212> TYPE: DNA
<213> ORGANISM: artificial
<220> FEATURE:
<223> OTHER INFORMATION: primer : a region homologous to the sequence
```

(2350669-2350748) of the glpA gene (sequence 2350669 to 2352297), and a region for the amplification of the chloramphenicol resistance cassette of the pKD3 plasmid

<400> SEQUENCE: 66
atgaaaactc gcgactcgca atcaagtgac gtgattatca ttggcggcgg cgcaacggga   60
gccgggattg cccgcgactg catatgaata tcctccttag                         100

<210> SEQ ID NO 67
<211> LENGTH: 98
<212> TYPE: DNA
<213> ORGANISM: artificial
<220> FEATURE:
<223> OTHER INFORMATION: primer : a region homologous to the seq
      (2352297-2352220) corresponding to the C terminal part encoding
      seq of the glpA gene (2350669 to 2352297), and a region for the
      amplification of the chloramphenicol resistance cassette of the
      pKD3 plasmid

<400> SEQUENCE: 67
tcaaagcgca tctttctgct ccttctccag accacacaat ccctgataaa cccagcgggt   60
aaattcgctt tcgcgcagtg taggctggag ctgcttcg                           98

<210> SEQ ID NO 68
<211> LENGTH: 22
<212> TYPE: DNA
<213> ORGANISM: artificial
<220> FEATURE:
<223> OTHER INFORMATION: primer : homologous to the E. coli sequence
      2349038 to 2349052

<400> SEQUENCE: 68
ttagcctccg ttgcgttctt gc                                            22

<210> SEQ ID NO 69
<211> LENGTH: 28
<212> TYPE: DNA
<213> ORGANISM: artificial
<220> FEATURE:
<223> OTHER INFORMATION: primer: homologous to the E. coli sequence
      2352316 to 3352289

<400> SEQUENCE: 69
gccgcccata atgacagtat caaagcgc                                      28

<210> SEQ ID NO 70
<211> LENGTH: 61
<212> TYPE: DNA
<213> ORGANISM: artificial
<220> FEATURE:
<223> OTHER INFORMATION: primer pntAA-NheIf

<400> SEQUENCE: 70
aattgctagc attatataca aggaggaaac agctatgcga attggcatac caagagaacg   60
g                                                                   61

<210> SEQ ID NO 71
<211> LENGTH: 37
<212> TYPE: DNA
<213> ORGANISM: artificial
<220> FEATURE:
<223> OTHER INFORMATION: primer pntB-xma1r

<400> SEQUENCE: 71
aattcccggg ataattttac agagctttca ggattgc                            37

<210> SEQ ID NO 72
<211> LENGTH: 38
<212> TYPE: DNA
<213> ORGANISM: artificial
<220> FEATURE:
<223> OTHER INFORMATION: primer pdhaB1f: BamHI-RBS dhaB1

<400> SEQUENCE: 72
ggatccgtga ttggaggagt aaaaatgata agtaaagg                          38

<210> SEQ ID NO 73
<211> LENGTH: 39
<212> TYPE: DNA
<213> ORGANISM: artificial
<220> FEATURE:
<223> OTHER INFORMATION: primer pdhaB2r:XhoI-dhaB2

<400> SEQUENCE: 73
ctcgagttac tcagctccaa ttgtgcacgg tattcccat                         39

<210> SEQ ID NO 74
<211> LENGTH: 58
<212> TYPE: DNA
<213> ORGANISM: artificial
<220> FEATURE:
<223> OTHER INFORMATION: primer pyqhD1: XhoI RBS01 yqhD

<400> SEQUENCE: 74
ctcgagttat aacctcctta atgaacaact ttaatctgca caccccaacc cgcattct    58

<210> SEQ ID NO 75
<211> LENGTH: 41
<212> TYPE: DNA
<213> ORGANISM: artificial
<220> FEATURE:
<223> OTHER INFORMATION: primer pyqhD2 : SfoI ?yqhDrv

<400> SEQUENCE: 75
ggcgccttag cgggcggctt cgtatatacg gcggctgaca t                      41

<210> SEQ ID NO 76
<211> LENGTH: 102
<212> TYPE: DNA
<213> ORGANISM: artificial
<220> FEATURE:
<223> OTHER INFORMATION: primer: a region homologous to the sequence
    (4109530-4109449) of the tpiA gene (sequence 4108763 to 4109530),
    and a region for the amplification of the chloramphenicol
    resistance cassette of the pKD3 plasmid

<400> SEQUENCE: 76
atgcgacatc ctttagtgat gggtaactgg aaactgaacg gcagccgcca catggttcac    60
gagctggttt ctaacctgcg tacatatgaa tatcctcctt ag                      102

<210> SEQ ID NO 77
<211> LENGTH: 100
<212> TYPE: DNA
<213> ORGANISM: artificial
<220> FEATURE:
<223> OTHER INFORMATION: primer:a region homologous to the seq (4108762-
    4108841) corresponding to the C terminal part encoding seq of the
    tpiA gene (4108763 to 4109530), and a region for the amplification
    of the chloramphenicol resistance cassette of the pKD3 plasmid

<400> SEQUENCE: 77

```
cttaagcctg tttagccgct tctgcagctt taacgattac tgcgaaggcg tcagctttca      60
gagaagcacc accaaccagc tgtaggctgg agctgcttcg                            100
```

<210> SEQ ID NO 78
<211> LENGTH: 20
<212> TYPE: DNA
<213> ORGANISM: artificial
<220> FEATURE:
<223> OTHER INFORMATION: primer: homologous to the E. coli sequence
      4107979 to 4107998

<400> SEQUENCE: 78

```
ggtgatgata gttatcgccg                                                  20
```

<210> SEQ ID NO 79
<211> LENGTH: 20
<212> TYPE: DNA
<213> ORGANISM: artificial
<220> FEATURE:
<223> OTHER INFORMATION: primer: homologous to the E. coli sequence
      4110023 to 4110042

<400> SEQUENCE: 79

```
cgtgccatcg acagcagtcc                                                  20
```

<210> SEQ ID NO 80
<211> LENGTH: 101
<212> TYPE: DNA
<213> ORGANISM: artificial
<220> FEATURE:
<223> OTHER INFORMATION: primer: a region homologous to the sequence
      (1725861-1725940) of the gloA gene (sequence 1725861 to 1726268),
      and a region for the amplification of the chloramphenicol
      resistance cassette of the pKD3 plasmid

<400> SEQUENCE: 80

```
atgcgtcttc ttcataccat gctgcgcgtt ggcgatttgc aacgctccat cgatttttat      60
accaaagtgc tgggcatgaa gtgtaggctg gagctgcttc g                          101
```

<210> SEQ ID NO 81
<211> LENGTH: 100
<212> TYPE: DNA
<213> ORGANISM: artificial
<220> FEATURE:
<223> OTHER INFORMATION: primer:a region homologous to the seq
      (1726189?1726268) corresponding to the C terminal part encoding
      seq of the gloA gene (1725861 to 1726268), and a region for the
      amplification of the chloramphenicol resistance cassette of the
      pKD3 plasmid

<400> SEQUENCE: 81

```
ttagttgccc agaccgcgac cggcgtcttt ctcttcgatt aactcaattt tgtaaccgtc      60
cggatcttcc acaaacgcga catatgaata tcctccttag                            100
```

<210> SEQ ID NO 82
<211> LENGTH: 31
<212> TYPE: DNA
<213> ORGANISM: artificial
<220> FEATURE:
<223> OTHER INFORMATION: primer: homologous to the E. coli  sequence
      1725331 to 1725361

<400> SEQUENCE: 82

```
gaagtggtcg atgccgggat tgaagaatgg g                                     31
```

```
<210> SEQ ID NO 83
<211> LENGTH: 31
<212> TYPE: DNA
<213> ORGANISM: artificial
<220> FEATURE:
<223> OTHER INFORMATION: primer: homologous to the E. coli sequence
      1726765 to 1726795

<400> SEQUENCE: 83
gggttacgtt tcagtgaggc gcgttctgcg g                                 31

<210> SEQ ID NO 84
<211> LENGTH: 101
<212> TYPE: DNA
<213> ORGANISM: artificial
<220> FEATURE:
<223> OTHER INFORMATION: primer: a region homologous to the sequence
      (234703-234782) of the gloB gene (sequence 234027 to 234782), and
      a region for the amplification of the chloramphenicol resistance
      cassette of the pKD3 plasmid

<400> SEQUENCE: 84
acaatcaggc agcgacctgc ttcatcattc aaaacccaga tgtaattgtc atcaaaggcg    60
ggaatactgt taagattcat gtgtaggctg gagctgcttc g                      101

<210> SEQ ID NO 85
<211> LENGTH: 102
<212> TYPE: DNA
<213> ORGANISM: artificial
<220> FEATURE:
<223> OTHER INFORMATION: primer: a region homologous to the seq (234027-
      234108) corresponding to the C terminal part encoding seq of the
      gloB gene (234027 to 234782), and a region for the amplification
      of the chloramphenicol resistance cassette carried by the pKD3

<400> SEQUENCE: 85
taatgtaatt aatgaagaaa cattattgca acaacctgaa gagcgttttg catggttaag    60
gtcaaagaaa gataggttct gacatatgaa tatcctcctt ag                     102

<210> SEQ ID NO 86
<211> LENGTH: 22
<212> TYPE: DNA
<213> ORGANISM: artificial
<220> FEATURE:
<223> OTHER INFORMATION: primer : homologous to the E. coli sequence
      233929 to 233950

<400> SEQUENCE: 86
ggcgagtaat atcgcttttg cc                                           22

<210> SEQ ID NO 87
<211> LENGTH: 24
<212> TYPE: DNA
<213> ORGANISM: artificial
<220> FEATURE:
<223> OTHER INFORMATION: primer: homologous to the E. coli sequence
      234822 to 234845

<400> SEQUENCE: 87
gacagtttga gggactcttg ccgg                                         24

<210> SEQ ID NO 88
<211> LENGTH: 121
<212> TYPE: DNA
<213> ORGANISM: artificial
<220> FEATURE:
<223> OTHER INFORMATION: primer: a region homologous to the sequence
```

(2033859-2033938) of the hchA gene (sequence 2033859 to 2034710), and a region for the amplification of the chloramphenicol resistance cassette of the pKD3 plasmid

<400> SEQUENCE: 88
atgactgttc aaacaagtaa aaatccgcag gtcgatattg ctgaagataa tgcattcttc    60
ccttcagaat attcgcttag ccttcagaat attcgcttag gtgtaggctg gagctgcttc   120
g                                                                  121

<210> SEQ ID NO 89
<211> LENGTH: 100
<212> TYPE: DNA
<213> ORGANISM: artificial
<220> FEATURE:
<223> OTHER INFORMATION: primer: a region homologous to the seq
      (2034631-2034710) corresponding to the C terminal part encoding
      seq of the hchA gene (2033859 to 2034710), and a region for the
      amplification of the chloramphenicol resistance cassette of the
      pKD3 plasmid

<400> SEQUENCE: 89
ttaacccgcg taagctgcca gcatttcctg cgccgccagt ttacccaacg cattcgctgc    60
aaaaggactg tcgccggtga catatgaata tcctccttag                        100

<210> SEQ ID NO 90
<211> LENGTH: 22
<212> TYPE: DNA
<213> ORGANISM: artificial
<220> FEATURE:
<223> OTHER INFORMATION: primer: homologous to the E. coli sequence
      2033243-2033264

<400> SEQUENCE: 90
tgtgggctta gtctaccagt tc                                            22

<210> SEQ ID NO 91
<211> LENGTH: 20
<212> TYPE: DNA
<213> ORGANISM: artificial
<220> FEATURE:
<223> OTHER INFORMATION: primer: homologous to the E. coli sequence
      2034818 to 2034837

<400> SEQUENCE: 91
cgttaccgca aagaaattaa                                               20

<210> SEQ ID NO 92
<211> LENGTH: 46
<212> TYPE: DNA
<213> ORGANISM: artificial
<220> FEATURE:
<223> OTHER INFORMATION: primer pgldA1f: BamHI-RBS gldA

<400> SEQUENCE: 92
ggatccttat aacctcctta atggaccgca ttattcaatc accggg                  46

<210> SEQ ID NO 93
<211> LENGTH: 31
<212> TYPE: DNA
<213> ORGANISM: artificial
<220> FEATURE:
<223> OTHER INFORMATION: primer pgldAr:XhoI-gldA

<400> SEQUENCE: 93
ctcgagttat tcccactctt gcaggaaacg c                                  31

```
<210> SEQ ID NO 94
<211> LENGTH: 49
<212> TYPE: DNA
<213> ORGANISM: artificial
<220> FEATURE:
<223> OTHER INFORMATION: primer psadh1f : BamHI-RBSsadh

<400> SEQUENCE: 94
ggatcctatc tttaaggagg aacatatttt atgaaaggtt ttgcaatgc                49

<210> SEQ ID NO 95
<211> LENGTH: 43
<212> TYPE: DNA
<213> ORGANISM: artificial
<220> FEATURE:
<223> OTHER INFORMATION: primer psadh2r:XhoI-sadh

<400> SEQUENCE: 95
ctcgagttat aataacta ctgctttaat taagtctttt ggc                        43
```

The invention claimed is:

1. A modified microorganism having Ferredoxin NADP+ reductase enzymatic activity, wherein a polynucleotide coding for the polypeptide having at least 85% identity with the sequence of SEQ ID NO: 1 is overexpressed and having Ferredoxin NADP+ reductase activity as expressed,
wherein the modified microorganism contains at least one modification selected in the group consisting of:
a modification to produce ethanol,
a modification to produce n-butanol,
a modification to produce 1,3-propanediol, and
a modification to produce 1,2-propanediol,
wherein, when the modified microorganism contains at least one modification to produce ethanol, the at least one modification to produce ethanol comprises:
enhancement of the expression of at least one of the following genes: pfor, fdx and udhA,
and
attenuation of the expression of at least one of the following genes: aceE, aceF, lpd, pflA, pflB, frd-ABCD, ldhA, mgsA, ackA, pta, poxB and iscR,
wherein, when the modified microorganism contains at least one modification to produce n-butanol, the at least one modification to produce n-butanol comprises:
enhancement of the expression of atoB, crt, adhE2 and hbd genes and of at least one of the following genes: pfor, fdx, bcd, etfA, etfB and udhA,
and
attenuation of the expression of at least one of the following genes: aceE, aceF, lpd, pflA, pflB, frd-ABCD, adhE, ldhA, mgsA, ackA, pta, poxB and iscR,
wherein, when the modified microorganism contains at least one modification to produce 1,3-propanediol, the at least one modification to produce 1,3-propanediol comprises:
enhancement of the expression of pntAB, dhaB1, dhaB2 and yqhD genes and of at least one of the following genes: pfor and,
and
attenuation of the expression of at least one of the following genes: aceE, aceF, lpd, aldA, aldB, ldhA, pflA, pflB, adhE, iscR, glpA, poxB and glpD,
wherein, when the modified microorganism contains at least one modification to produce 1,2-propanediol, the at least one modification to produce 1,2-propanediol comprises:
attenuation of the expression of at least one of the following genes: ptsG, ptsH, ptsI, crr, edd, eda, gloA, aceE, aceF, lpd, aldA, aldB, ldhA, pflA, pflB, adhE, tpiA, gapA, pykA, pykF, ackA, pta, poxB, arcA and ndh,
and
enhancement of the expression of pntAB, gldA and yqhD genes and at least one of the following genes: pfor, fdx, gapN, galP, glk, ppsA, mgsA yafB, ydhF, ycdW, yqhE, yeaE, yghZ, yajO, tas, ydjG, ydbC, and fucO.

2. A method for preparing ethanol comprising culturing a microorganism having a modification to produce ethanol according to claim 1 in culture medium that includes a source of carbon and recovering the ethanol.

3. A method for preparing n-butanol comprising culturing a microorganism having a modification to produce n-butanol according to claim 1 in culture medium that includes a source of carbon and recovering the n-butanol.

4. A method for preparing 1,3-propanediol comprising culturing a microorganism having a modification to produce 1,3-propanediol according to claim 1 in a culture medium that includes a source of carbon and recovering the 1,3-propanediol.

5. A method for preparing 1,2-propanediol comprising culturing a microorganism having a modification to produce 1,2-propanediol according to claim 1 in culture medium that includes a source of carbon and recovering the 1,2-propanediol.

* * * * *